(12) United States Patent
Mitchell et al.

(10) Patent No.: US 8,598,194 B2
(45) Date of Patent: Dec. 3, 2013

(54) POLYCYCLIC AGENTS FOR THE TREATMENT OF RESPIRATORY SYNCYTIAL VIRUS INFECTIONS

(75) Inventors: **

(56) References Cited

OTHER PUBLICATIONS

Van Den Hoogen et al., "Clinical impact and diagnosis of human metapneumovirus infection," *Pediatr. Infect. Dis. J.* 2004, vol. 23(1 Suppl), pp. S25-S32.
Van Den Hoogen et al., "Analysis of the genomic sequence of a human metapneumovirus," *Antivir. Ther.* 1998, vol. 295, pp. 119-132.
Hall et al., "Aerosolized ribavirin treatment of infants with respiratory syncytial viral infection. A randomized double-blind study," *N. Engl. J. Med.* 1983, vol. 308, pp. 1443-1447.
Hall et al., "Ribavirin treatment of respiratory syncytial viral infection in infants with underlying cardiopulmonary disease," *JAMA* 1985, vol. 254, pp. 3047-3051.
Guion et al., "The Preparation of 2-(2-Oxo-2-Phenylethyl) Benzoic Acids from Dilithiated *Ortho*-Toluic Acid.," *Synth. Comm.* 1996, vol. 26, pp. 1753-1762.
Epsztajn et al., "Application of Organolithium and Related Reagents in Synthesis. Part 11. Metallation of 2-Methyl- and 4-Methylnicotinic Acids. A Useful Method for Preparation of AZA-Isocoumarins,".*Synth. Comm.* 1992, vol. 22, pp. 1239-1247.
Bruggink et al., "A study of the copper-catalysed direct arylation of β-dicarbonyl compounds with 2-bromobenzoic acids," *Tetrahedron* 1975, vol. 31, pp. 2607-2619.
Ames et al., "Heterocyclic synthesis from *o*-halogeno-acids. Part III. Synthesis of 2-methylindole-4-carboxylic acid and related compounds and of some derivatives of 3-phenylisoquinolin-1(2*H*)-one," *J. Chem. Soc. Perkin Trans. 1* 1976, pp. 1073-1078.
Prasad et al., "18-Crown-6 as a catalyst in the dialkylation of o-nitrophenacyl derivatives," *J. Org. Chem.* 1991, vol. 56, pp. 7188-7190.
Kruse et al., "Some benzyl-substituted imidazoles, triazoles, tetrazoles, pyridinethiones, and structural relatives as multisubstrate inhibitors of dopamine .beta.-hydroxylase. 4. Structure-activity relationships at the copper binding site," *J. Med. Chem.* 1990, vol. 33, pp. 781-789.
Sulkowski et al., "2,5-Benzodiazocines and intermediates," *J. Org. Chem.* 1967, vol. 32, pp. 2180-2184.
Aeberli et al., "5-Aryl-2,3-dihydro-5H-imidazo[2,1-a]isoindol-5-ols. Novel class of anorectic agents," *J. Med. Chem.* 1975, vol. 18, pp. 177-182.
Aeberli et al., "Anorectic agents. 2. Structural analogs of 5-(p-chlorophenyl)-2,3-dihydro-5H-imidazo[2,1-a]isoindol-5-ol," *J. Med. Chem.* 1975, vol. 18, pp. 182-185.
Aeberli et al., "Lithium aluminum hydride reduction products from heterocycles containing an isoindolone nucleus," *J. Org. Chem.* 1969, vol. 34, pp. 1720-1726.
Katritzky et al., "Convenient syntheses of dihydropyrrolo[2',1':3,4]pyrazino- and dihydropyrrolo[2',1':3,4][1,4]diazepino-[2,1-a]isoind olones," *Tretrahedron Let.* 2002, vol. 43, pp. 2831-2833.
Katritzky et al., "Stereoselective syntheses of chiral (3S,9bS)-1,2,3,9b-tetrahydro-5*H*-imidazo[2,1-*a*]isoindol-5-ones," *Tretrahedron Asymmetry* 2002, vol. 13, pp. 933-938.
Watanabe et al., "MTT colorimetric assay system for the screening of anti-orthomyxo- and anti-paramyxoviral agents," *J. Virological Methods* 1994, vol. 48, pp. 257-265.
Morton et al., "Structural characterization of respiratory syncytial virus fusion inhibitor escape mutants: homology model of the F protein and a syncytium formation assay," *Virology* 2003, vol. 311, pp. 275-288.
Wyde et al., "Short duration aerosols of JNJ 2408068 (R170591) administered prophylactically or therapeutically protect cotton rats from experimental respiratory syncytial virus infection," *Antiviral Res.* 2003, vol. 60, pp. 221-231.
Cianci et al., "Orally Active Fusion Inhibitor of Respiratory Syncytial Virus," *Antimicrob. Agents Chemother.* 2004, vol. 48, pp. 413-422.
Yamaguchi et al., "Novel antiasthmatic agents with dual activities of thromboxane $A_2$ synthetase inhibition and bronchodilation. 1, 2-[2-(1-Imidazolyl)alkyl]-1(2H)-phthalazinones," *J. Med. Chem.* 1993, vol. 36, pp. 4052-4060.

Natsugari et al., "Novel, potent, and orally active substance P antagonists: synthesis and antagonist activity of N-benzylcarboxamide derivatives of pyrido[3,4-b]pyridine," *J. Med. Chem.* 1995, vol. 38, pp. 3106-3120.
Metlesics et al., "Structure of the reaction product of o-benzoylbenzoic acid with ethylenediamine," *J. Org. Chem.* 1967, vol. 32, pp. 2185-2187.
CA abstract 67:43744 and RN 13449-92-8.
CA abstract 67:43799 and RNs 5810-68-4, 5983-39-1, 5983-45-9, 13450-15-2.
CA abstract 71:38862 and RNs 5983-38-0, 5983-39-1.
CA abstract 137:337826 and RN 473998-86-6.
Combrink et al., "Respiratory syncytial virus fusion inhibitors. Part 6: An examination of the effect of structural variation of the benzimidazol-2-one heterocycle moiety," *Bioorganic & Medicinal Chemistry Letters* 17:4784-4790, 2007.
McMurry, "Organic Chemistry," $3^{rd}$ ed., Brooks/Cole Publishing Co., USA, sections 4.9-4.16, 1992.
van den Hoogen et al., "Analysis of the genomic sequence of a human metapneumovrius" *Virology* 295:119-132, 2002.
Non-Final Office Action from corresponding U.S. Appl. No. 10/585,230, dated Dec. 9, 2009.
Non-Final Office Action from corresponding U.S. Appl. No. 10/585,230, dated May 26, 2010.
Final Office Action from corresponding U.S. Appl. No. 10/585,230, dated Dec. 8, 2010.
CAS Registry 327979-63-5, Entered STN Mar. 19, 2001.
CAS Registry 477867-90-6, Entered STN Dec. 31, 2002.
CAS Registry 477886-49-0, Entered STN Dec. 31, 2002.
Metlesics et al., "The structure of the reaction product of O-benzoylbezoic acid with ethylenediamine," *J Org. Chem.*, 32(7):2185-2187, 1967.
Stephenson, "New HIV prevention strategies urged," *JAMA* 292(10):1163-1164, 2004.
*The Chemical Society of Japan*, Separation of Enantiomers, Quarterly Journal, Chemical Review, 6:5, 1989.
CAS Registry 1018992-94-3, Entered STN Feb. 5, 2008.
CAS Registry 1018993-09-3, Entered STN Feb. 5, 2008.
CAS Registry 1018993-12-8, Entered STN Feb. 5, 2008.
CAS Registry 1018993-14-0, Entered STN Feb. 5, 2008.
CAS Registry 1018993-19-5, Entered STN Feb. 5, 2008.
CAS Registry 1018993-20-8, Entered STN Feb. 5, 2008.
CAS Registry 1018997-73-3, Entered STN Feb. 5, 2008.
CAS Registry 1018997-85-7, Entered STN Feb. 5, 2008.
CAS Registry 1018997-90-4, Entered STN Feb. 5, 2008.
CAS Registry 1018998-06-5, Entered STN Feb. 5, 2008.
CAS Registry 1018998-11-2, Entered STN Feb. 5, 2008.
CAS Registry 1018998-14-5, Entered STN Feb. 5, 2008.
CAS Registry 1018998-54-3, Entered STN Feb. 5, 2008.
CAS Registry 1019001-78-5, Entered STN Feb. 5, 2008.
CAS Registry 1019001-81-0, Entered STN Feb. 5, 2008.
CAS Registry 1019001-85-4, Entered STN Feb. 5, 2008.
CAS Registry 1019001-88-7, Entered STN Feb. 5, 2008.
CAS Registry 1019006-25-7, Entered STN Feb. 5, 2008.
CAS Registry 1019006-29-1, Entered STN Feb. 5, 2008.
CAS Registry 1019006-52-0, Entered STN Feb. 5, 2008.
CAS Registry 1019006-57-5, Entered STN Feb. 5, 2008.
CAS Registry 1019006-62-2, Entered STN Feb. 5, 2008.
CAS Registry 1019006-75-7, Entered STN Feb. 5, 2008.
CAS Registry 1019006-78-0, Entered STN Feb. 5, 2008.
CAS Registry 1019006-82-6, Entered STN Feb. 5, 2008.
CAS Registry 1019006-92-8, Entered STN Feb. 5, 2008.
CAS Registry 717817-82-8, Entered STN Jul. 27, 2004.
CAS Registry 903154-09-6, Entered STN Aug. 22, 2006.
CAS Registry 104024-49-9, Entered STN Aug. 30, 1986.
Non-Final Office Action from corresponding U.S. Appl. No. 13/023,473 dated Oct. 30, 2012.

* cited by examiner

POLYCYCLIC AGENTS FOR THE TREATMENT OF RESPIRATORY SYNCYTIAL VIRUS INFECTIONS

FIELD OF THE INVENTION

The present invention relates to antiviral compounds, methods for their preparation and compositions containing them, and the use of the compounds and composition in the treatment of viral infections. In particular, the invention relates to the use of compounds of formula I for the prevention and/or treatment of respiratory syncytial virus infection and disease.

BACKGROUND ART

Respiratory syncytial virus (RSV) is the leading cause of acute upper and lower respiratory tract infection in adults, young children and infants. Serological evidence indicates that in the western world approximately 95% of all children have been infected with RSV by the age of two and 100% of children have been exposed by the time they reach adulthood (see Black, C. P., 2003, Resp. Care 48:209-31 for a recent review of the biology and management of RSV). In most cases the RSV infections will only cause minor upper respiratory illness with symptoms resembling that of the common cold. However, severe infection with the virus may result in bronchiolitis or pneumonia which may result in hospitalization or death. In a given year, around 91,000 infants are hospitalized with RSV infection in the United States. Infants who have been born prematurely or have a pre-existing lung disease are a high risk of severe infection and complications. These infections are responsible for 40 to 50% of hospitalizations for pediatric bronchiolitis and 25% of hospitalizations for pediatric pneumonia. Since the immune response to RSV infection is not protective, RSV infections reoccur throughout adulthood. In adults and older children, RSV infection has been associated with upper respiratory infection, tracheobronchitis, and otitis media. However, RSV in the institutionalized elderly can be more serious and is characterized by severe pneumonia and mortality rates of up to 20 and 78%, respectively. Adults with a previous history of heart or lung conditions are at a high risk for RSV infection. The infection has been linked to exacerbation of patients with chronic obstructive pulmonary disease. Significant mortality has been observed in immunocompromised patients, particularly those undergoing bone marrow transplantation. (Evans, A. S., eds., 1989, Viral Infections of Humans. Epidemiology and Control, 3$^{rd}$ ed., Plenum Medical Book, New York at pages 525-544; Falsey, A. R., 1991, Infect. Control Hosp. Epidemiol. 12:602-608; and Garvie et al., 1980, Br. Med. J. 281:1253-1254; Hertz et al., 1989, Medicine 68:269-281).

RSV is a member of the order Mononegavirales, which consists of the non-segmented negative strand RNA viruses in the Families Paramyxoviridae, Rhabdoviridae and Filoviridae. RSV of humans (often also termed RSV or HRSV) is a member of the Pneumovirus genus of the sub-family Pneumovirinae within the Family Paramyxoviridae. Based on genetic and antigenic variations in the structural proteins, RSV is classified into two subgroups, A and B (Mufson, M. et al., J. Gen. Virol. 66:2111-2124). Other members of the Pneumovirus genus include viruses such as bovine RSV (BRSV), ovine RSV (ORSV) and pneumonia virus of mice (PVM) amongst others. The sub-family Pneumovirinae also includes the genus Metapneumovirus which contains the recently identified and important human pathogen human metapneumovirus (hMPV).

hMPV causes respiratory illness ranging from mild upper respiratory symptoms to severe lower respiratory disease such as bronchiolitis and pneumonia (van den Hoogen, B et al., 2001, Nat. Med. 7:719-724). Depending on the patient population sampled, between 5 and 15% of respiratory infections in young children may be attributable to hMPV infection (van den Hoogen, B. et al., 2003, J. Infect. Dis. 188:1571-1577). hMPV is also associated with 12 to 50% of otitis media in children (van den Hoogen, et al., 2004, Pediatr. Infect. Dis. J. 23:S25-S32). In the Netherlands, 55% of tested individuals were seropositive for hMPV by age 2, and almost all individuals 5 years and older were seropositive (van den Hoogen, et al., Virology 295:119-132).

In addition to the genome features described above, Family characteristics include a lipid envelope containing one or more glycoprotein species considered to be associated with attachment and entry of the host cell. Entry is considered to require a process by which the viral envelope fuses with the membrane of the host cell. Fusion of infected cells with, for example, their neighbours, can also result in the formation of fused multinucleate cells known as syncytia in some cases. The fusion process is believed to be glycoprotein mediated and is a feature shared with diverse enveloped viruses in other taxonomic groups. In the case of the Paramyxoviridae viruses of all genera characteristically express a fusion glycoprotein (F) which mediates membrane fusion.

While a RSV licensed vaccine is not yet available, some success has been achieved in the area of prevention for infants at high risk of serious lower respiratory tract disease caused by RSV, as well as a reduction of LRI. In particular, there are two immunoglobulin-based therapies approved to protect high-risk infants from serious LRI: RSV-IGIV (RSV-immunoglobulin intravenous, also known as RespiGam™) and palivizumab (SYNAGIS®). RSV-IGIV (RespiGam, Massachusetts Public Health Biological Laboratories and MedImmuneo Inc, Gaithersburg, Md.) was licensed by the Food and Drug Administration in January 1996 for prevention of severe RSV lower respiratory tract disease in infants and children younger than 24 months with CLD or a history of preterm birth (≤35 weeks' gestation). In June 1998, the Food and Drug Administration licensed palivizumab (MedImmune, Gaithersburg, Md.) for administration as a monthly intramuscular injection for the prevention of serious respiratory disease caused by RSV in infants and children with a history of preterm birth (≤35 weeks' gestation) or CLD.

The only drug currently approved for the treatment of severe RSV is the antiviral medication, Virazole, also known as Ribavirin currently licensed for therapy of RSV pneumonia and bronchiolitis (Hall et al, 1983, N. Engl. J. Med., 308: 1443; Hall et al., 1985, JAMA, 254:3047. This agent has a broad spectrum antiviral with virustatic effects, and acts by inhibiting RSV replication. Unfortunately, the agent is toxic so that administration of the agent is confined to a hospital setting (Black, C. P., 2003, Resp. Care 48(3):209-31). Its administration is further complicated by the need to follow a strict procedural process when administering the agent in order to minimise the likelihood of certain adverse affects. The agent has a number of adverse effects including sudden deterioration of respiratory function (bronchiospasm). The efficacy of Virazole has remained controversial and thus there is a real need to find an alternative agent for the treatment of RSV infection.

SUMMARY OF THE INVENTION

This invention provides compounds useful for the prevention and/or treatment of RSV infection and disease, of formula I and salts thereof Formula I

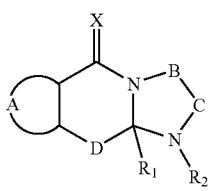

wherein:

R$_1$ is selected from C$_{1-12}$ alkyl, C$_{2-12}$ alkenyl, C$_{2-12}$ alkynyl, —(CH$_2$)$_n$C$_{3-7}$ cycloalkyl, —(CH$_2$)$_n$C$_{4-7}$ cycloalkenyl, —(CH$_2$)$_n$ aryl, —(CH$_2$)$_n$ arylC$_{1-12}$ alkyl, —(CH$_2$)$_n$ arylC$_{2-12}$ alkenyl, —(CH$_2$)$_n$arylC$_{2-12}$ alkynyl, and —(CH$_2$)$_n$ heterocyclyl; n is 0-6 and said alkyl, alkenyl, alkynyl, cycloalkyl, cycloalkenyl, aryl and heterocyclyl groups are optionally substituted;

R$_2$ is selected from H, O, —CH$_2$R$_3$, —C(=Y)R$_3$, —C(=Y)OR$_3$, —C(=Y)N(R$_4$)R$_3$, —C(=Y)CH$_2$N(R$_4$)R$_3$, —C(=Y)CH$_2$SR$_3$ and —S(O)$_w$R$_5$, where R$_3$ is selected from hydrogen, C$_{1-12}$ alkyl, C$_{2-12}$ alkenyl, C$_{2-12}$ alkynyl, —(CH$_2$)$_m$C$_{3-7}$ cycloalkyl, —(CH$_2$)$_m$C$_{4-7}$ cycloalkenyl, —(CH$_2$)$_m$ aryl, —(CH$_2$)$_m$ arylC$_{1-12}$ alkyl, —(CH$_2$)$_m$ aryl C$_{2-12}$ alkenyl, —(CH$_2$)$_m$ arylC$_{2-12}$ alkynyl and —(CH$_2$)$_m$ heterocyclyl; and when R$_2$ is —CH$_2$R$_3$, or —C(=Y)R$_3$, R$_3$ may also be selected from —S—R$_5$ and —O—R$_5$; m is 0-6; R$_4$ is hydrogen or C$_{1-6}$ alkyl; R$_5$ is C$_{1-6}$ alkyl, C$_{2-6}$ alkenyl, C$_{2-6}$ alkynyl, C$_{3-7}$ cycloalkyl, C$_{4-7}$ cycloalkenyl, benzyl, aryl or heterocyclyl; w is 0, 1 or 2, and the alkyl, alkenyl, alkynyl, cycloalkyl, cycloalkenyl, aryl and heterocyclyl groups are optionally substituted;

X and Y are independently selected from O, S and NR$_6$, where R$_6$ is independently selected from hydrogen, lower alkyl, hydroxy and lower alkoxy;

A together with the atoms to which it is attached, forms an optionally substituted aromatic ring;

B—C together with the atoms to which they are attached, forms an optionally substituted heterocyclic ring having from 5 to 8 ring atoms;

D represents a bivalent linking group of from one to three atoms in length, and provided that when A together with the atoms to which it is attached forms an unsubstituted phenyl ring, X is O, D is —CH$_2$—, B—C represents —CH$_2$CH$_2$—, and R$_1$ is unsubstituted phenyl, then R$_2$ is not H.

The invention also provides the use of compounds, and their salts, in the manufacture of medicaments for the prevention and/or treatment of RSV infections.

Although the invention has been described with reference to treating RSV, and in particularly human RSV, it will be appreciated that the invention may also be useful in the treatment of other viruses of the sub-family Pneumovirinae, more particularly, the genera Pneumovirus and Metapneumovirus, more particularly animal and human strains of RSV and metapneumovirus.

Accordingly, the invention also provides the use of compounds of formula Ia and salts thereof Formula Ia

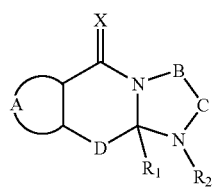

wherein:

R$_1$ is selected from C$_{1-12}$ alkyl, C$_{2-12}$ alkenyl, C$_{2-12}$ alkynyl, —(CH$_2$)$_n$C$_{3-7}$ cycloalkyl, —(CH$_2$)$_n$C$_{4-7}$ cycloalkenyl, —(CH$_2$)$_n$ aryl, —(CH$_2$)$_n$ arylC$_{1-12}$ alkyl, —(CH$_2$)$_n$ arylC$_{2-12}$ alkenyl, —(CH$_2$)$_n$arylC$_{2-12}$ alkynyl, and —(CH$_2$)$_n$ heterocyclyl; n is 0-6 and said alkyl, alkenyl, alkynyl, cycloalkyl, cycloalkenyl, aryl and heterocyclyl groups are optionally substituted;

R$_2$ is selected from H, O, —CH$_2$R$_3$, —C(=Y)R$_3$, —C(=Y)OR$_3$, —C(=Y)N(R$_4$)R$_3$, —C(=Y)CH$_2$N(R$_4$)R$_3$, —C(=Y)CH$_2$SR$_3$ and —S(O)$_w$R$_5$, where R$_3$ is selected from hydrogen, C$_{1-12}$ alkyl, C$_{2-12}$ alkenyl, C$_{2-12}$ alkynyl, —(CH$_2$)$_m$C$_{3-7}$ cycloalkyl, —(CH$_2$)$_m$C$_{4-7}$ cycloalkenyl, —(CH$_2$)$_m$ aryl, —(CH$_2$)$_m$ arylC$_{1-12}$ alkyl, —(CH$_2$)$_m$ aryl C$_{2-12}$ alkenyl, —(CH$_2$)$_m$ arylC$_{2-12}$ alkynyl and —(CH$_2$)$_m$ heterocyclyl; and when R$_2$ is —CH$_2$R$_3$, or —C(=Y)R$_3$, R$_3$ may also be selected from —S—R$_5$ and —O—R$_5$; m is 0-6; R$_4$ is hydrogen or C$_{1-6}$ alkyl; R$_5$ is C$_{1-6}$ alkyl, C$_{2-6}$ alkenyl, C$_{2-6}$ alkynyl, C$_{3-7}$ cycloalkyl, C$_{4-7}$ cycloalkenyl, benzyl, aryl or heterocyclyl; w is 0, 1 or 2, and the alkyl, alkenyl, alkynyl, cycloalkyl, cycloalkenyl, aryl and heterocyclyl groups are optionally substituted;

X and Y are independently selected from O, S and NR$_6$, where R$_6$ is independently selected from hydrogen, lower alkyl, hydroxy and lower alkoxy;

A together with the atoms to which it is attached, forms an optionally substituted aromatic ring;

B—C together with the atoms to which they are attached, forms an optionally substituted heterocyclic ring having from 5 to 8 ring atoms;

D represents a bivalent linking group of from one to three atoms in length, in the manufacture of a medicament for the prevention and/or treatment of RSV infections.

The invention also provides a method of treating a RSV infection in a subject in need thereof, including the step of administering a compound of formula Ia or a pharmaceutically acceptable salt thereof to said subject.

DESCRIPTION OF PREFERRED EMBODIMENTS

As used herein the term "aromatic" refers to aryl rings or ring systems and aromatic heterocyclic rings or ring systems, as known as heteroaryl or heteroaromatic rings.

As used herein the term "aryl" refers to carbocyclic (non-heterocyclic) aromatic rings or ring systems. The aromatic rings may be mono-, bi-cyclic or tri-cyclic ring systems. The aromatic rings or ring systems are generally composed of 5 to 10 carbon atoms. Examples of suitable aryl groups include but are not limited to phenyl, biphenyl, naphthyl, tetrahydronaphthyl, and the like.

Preferred aryl groups include phenyl, naphthyl, indenyl, azulenyl, fluorenyl or anthracenyl.

The term "heterocyclic" or "heterocyclyl" as used herein refers to mono or bicyclic rings or ring systems that include one or more heteroatoms selected from N, S and O. The rings or ring systems generally include 1 to 9 carbon atoms in addition to the heteroatom(s) and may be saturated, unsaturated or aromatic (including pseudoaromatic). The term "pseudoaromatic" refers to a ring system which is not strictly aromatic, but which is stabilized by means of delocalization of electrons and behaves in a similar manner to aromatic rings. Aromatic includes pseudoaromatic ring systems, such as furyl, thienyl and pyrrolyl rings.

Examples of 5-membered monocyclic heterocycles include furyl, thienyl, pyrrolyl, H-pyrrolyl, pyrrolinyl, pyrrolidinyl, oxazolyl, oxadiazolyl, (including 1,2,3 and 1,2,4 oxadiazolyls) thiazolyl, isoxazolyl, furazanyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls). Examples of 6-membered monocyclic heterocycles include pyridyl, pyrimidinyl, pyridazinyl, pyranyl, pyrazinyl, piperidinyl, 1,4-dioxanyl, morpholinyl, 1,4-dithianyl, thiomorpholinyl, piperazinyl, 1,3,5-trithianyl and triazinyl. The heterocycles may be optionally substituted with a broad range of substituents, and preferably with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino.

The heterocycle may be fused to a carbocyclic ring such as phenyl, naphthyl, indenyl, azulenyl, fluorenyl, and anthracenyl.

Examples of 8, 9 and 10-membered bicyclic heterocycles include 1H thieno[2,3-c]pyrazolyl, thieno[2,3-b]furyl, indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, uridinyl, purinyl, cinnolinyl, phthalazinyl, quinazolinyl, quinoxalinyl, benzotriazinyl, naphthyridinyl, pteridinyl and the like. These heterocycles may be optionally substituted, for example with $C_{1-6}$alkyl, $C_{1-6}$alkoxy, $C_{2-6}$alkenyl, $C_{2-6}$alkynyl, halo, hydroxy, mercapto, trifluoromethyl, amino, cyano or mono or di($C_{1-6}$alkyl)amino.

In an embodiment the heterocyclic radicals include (optionally substituted) isoxazoles, isothiazoles, 1,3,4-oxadiazoles, 1,3,4-thiadiazoles, 1,2,4-oxadiazoles, 1,2,4-thiadiazoles, oxazoles, thiazoles, pyridines, pyridazines, pyrimidines, pyrazines, 1,2,4-triazines, 1,3,5-triazines, benzoxazoles, benzothiazoles, benzisoxazoles, benzisothiazoles, quinolines and quinoxalines. These heterocycles can be optionally substituted with, by example, $C_{1-6}$alkyl, $C_{1-6}$alkoxy, $C_{2-6}$alkenyl, $C_{2-6}$alkynyl, halo, hydroxy, mercapto, trifluoromethyl, amino, cyano or mono or di($C_{1-6}$alkyl)amino.

In a further embodiment the heterocyclic radicals include furyl, thienyl, pyridyl, oxazolyl, thiazolyl, pyrazolyl, furazanyl, isoxazolyl, isothiazolyl, 1,2,3-triazolyl, 1,3,4-triazolyl, 1,2,3-thiadiazolyl, 1,3,4-thiadiazolyl, pyridazinyl, pyrimidinyl, benzo[b]furanyl, benzo[b]thiophenyl and benzoisoxazolyl.

Examples of unsaturated 5-membered heterocyclic rings include oxazole, thiazole, imidazole, 1,2,3-triazole, isoxazole, isothiazole, pyrazole, furan, thiophene and pyrrole. Examples of unsaturated 6-membered heterocyclic rings include pyridine, pyrimidine, pyrazine, pyridazine and 1,2,4-triazine.

In an embodiment the heterocyclic ring is an aromatic ring. Heteroaryl and heteroaromatic are used herein to refer to this subset of heterocyclic rings. Heteroaryl rings include furyl, thienyl, pyridyl, pyrrolyl, oxazolyl, thiazolyl, imidazolyl, pyrazolyl, isoxazolyl, isothiazolyl, 1,2,3-oxadiazolyl, 1,2,4-oxadiazolyl, 1,2,4-oxadiazol-5-one, 1,2,3-triazolyl, 1,3,4-thiadiazolyl, pyridazinyl, pyrimidinyl, pyrazinyl, 1,3,5-triazinyl, 1H thieno[2,3-c]pyrazolyl, thieno[2,3-b]furyl, indolizinyl, indolyl, isoindolyl, 3H-indolyl, indolinyl, benzo[b]furanyl, benzo[b]thiophenyl, 1H-indazolyl, benzimidazolyl, tetrazolyl, uridinyl, and cytosinyl.

In a further embodiment the heteroaryl or heteroaromatic is selected from isoxazolyl, oxazolyl, imidazolyl, thiazolyl, thiadiazolyl, isothiazolyl, furazanyl, triazolyl, pyridyl, pyrimidinyl, furyl, pyrazolyl, pyridazinyl, thienyl and aryl fused heteroaromatic rings such as benzfuranyl, benzothiophenyl and benzoisoxazolyl.

In another embodiment, the heterocyclic ring is a non-aromatic ring selected from the group consisting of pyrrolidine, imidazoline, 2-imidazolidone, 2-pyrrolidone, pyrrolin-2-one, tetrahydrofuran, 1,3-dioxolane, piperidine, tetrahydropyran, oxazoline, 1,3-dioxane, 1,4-piperazine, morpholine and thiomorpholine.

The heterocyclic ring containing the linker group B—C may be selected from the above described heterocyclic rings provided the ring meets the requirement of containing at least two nitrogen atoms and excludes aromatic ring systems.

Unless otherwise defined, the term "optionally substituted" as used herein means that a group may include one or more substituents that do not reduce the binding activity of the compound of formulae I and Ia. In some instances the substituent may be selected to improve binding or alter other properties of the molecule. The group may be substituted with one or more substituents selected from halogens, $C_{1-6}$ alkyl, $C_{2-6}$ alkenyl, $C_{2-6}$ alkynyl, —$(CH_2)_pC_{3-7}$ cycloalkyl, —$(CH_2)_p C_{4-7}$ cycloalkenyl, —$(CH_2)_p$ aryl, —$(CH_2)_p$ heterocyclyl, —$C_6H_4S(O)_tC_{1-6}$ alkyl, —$C(Ph)_3$, —$(CH_2)_pZ$, —COZ, —CN, —OR, —O—$(CH_2)_{1-6}$—R, —O—$(CH_2)_{1-6}$—OR, —OCOR, —COR, —COOR, —OCONR'R", —C(O)NR'R", —NR'R", —NRCOR', —NRCONR'R", —NRC(=S)NR'R", —NRSO$_2$R', —NRCOOR', —C(=NR)NR'R", —CRNOR', —C(=NOH)NR'R", —CONR'R", —C(=NCN)—NR'R", —C(=NR)NR'R", —C(=NR')SR", —NR'C(=NCN)SR", —CONRSO$_2$R', —C(=S)NR'R", —S(O)$_t$R, —SO$_2$NR'R", —SO$_2$NRCOR', —OS(O)$_2$R', —PO(OR)$_2$ and —NO$_2$; where p is 0-6, t is 0-2, Z is an N-linked amino acid selected from the group consisting of alanine, asparagine, aspartic acid, glutamic acid, glutamine, glycine, pipecolic acid, α-amino-butyric acid, α-amino-propanoic acid, and iminodiacetic acid, Z being linked through a nitrogen atom of said N-linked amino acid to the carbon atom, and each R', R" and R'" is independently selected from H, $C_{1-6}$ alkyl, $C_{2-6}$ alkenyl, $C_{2-6}$ alkynyl, $C_{3-7}$ cycloalkyl, $C_{4-7}$ cycloalkenyl, aryl, heterocyclyl, $C_{1-6}$ alkylaryl and $C_{1-6}$ alkylheterocyclyl, wherein the alkyl, alkenyl, alkynyl, cycloalkyl, cycloalkenyl, aryl, heterocyclyl, $C_{1-6}$ alkylaryl or $C_{1-6}$ alkylheterocyclyl, may be optionally substituted with one to six of same or different selected from halogen, hydroxy, lower alkyl, lower alkoxy, —CO$_2$H, CF$_3$, CN, phenyl, NH$_2$ and —NO$_2$; or when R' and R" are attached to the same nitrogen atom, they may, together with the atom to which they are attached, form a 5 to 7 membered nitrogen containing heterocyclic ring.

When the optional substituent is or contains an alkyl, alkenyl, alkynyl, cycloalkyl, cycloalkenyl, aryl or heterocyclyl group, the group may itself be optionally substituted with one to six of the same or different halogen atoms, hydroxy, lower alkyl, lower alkoxy, halo-$C_{1-6}$ alkyl (including —CF$_3$), phenyl, benzyl, —CN, —C(=O)—$C_{1-6}$ alkyl, mercapto, —NH$_2$, mono or di(lower alkyl)amino or —NO$_2$.

In relation to nitrogen containing heterocyclic rings, unless otherwise defined optionally substituted includes pyridinium salts and the N-oxide form of suitable ring nitrogens.

In relation to non-aromatic carbocyclic or heterocyclic compounds, unless otherwise defined such compounds may also be optionally substituted with one or two =O groups, instead of or in addition to the above described optional substituents.

Examples of optional substituents include halogens, $C_{1-4}$ alkyl, $C_{2-4}$ alkenyl, $C_{2-4}$ alkynyl, $C_{1-4}$ alkoxy, $C_{1-4}$ haloalkyl, —$CF_3$, —OH, phenyl, —$NH_2$, —$NHC_{1-4}$ alkyl, —$N(C_{1-4})_2$, —CN, mercapto, $C_{1-4}$ alkylcarbonyl and $C_{1-4}$ alkoxycarbonyl.

As used herein the term "$C_{1-12}$ alkyl" refers to straight chain or branched saturated hydrocarbon group having from 1 to 12 carbon atoms. Examples of such alkyl groups include methyl, ethyl, n-propyl, isopropyl, n-butyl, isobutyl, sec-butyl or tert-butyl. Similarly "$C_{1-6}$ alkyl" or "lower alkyl" refers to such groups having from 1 to 6 carbon atoms.

As used herein the term "$C_{3-7}$ cycloalkyl" refers to non-aromatic, saturated cyclic groups having from 3 to 7 carbon atoms. Examples include cyclopentyl and cyclohexyl.

As used herein the term "alkoxy" refers to a straight or branched alkyl group covalently bound via an O linkage and the terms "$C_{1-6}$ alkoxy" and "lower alkoxy" refer to such groups containing from one to six carbon atoms, such as methoxy, ethoxy, propoxy, isopropoxy, butoxy, t-butoxy and the like.

As used herein the term "$C_{2-12}$ alkenyl" refers to groups formed from $C_{2-12}$ straight chain or branched non-cyclic hydrocarbon containing one or more double bonds. Examples of $C_{2-12}$ alkenyl include allyl, 1-methylvinyl, butenyl, isobutenyl, 1,3-butadienyl, 3-methyl-2-butenyl, 1,3-butadienyl, 1,4-pentadienyl, 1-pentenyl, 1-hexenyl, 3-hexenyl, 1,3-hexadienyl, 1,4-hexadienyl and 1,3,5-hexatrienyl.

As used herein the term "$C_{4-7}$ cycloalkenyl" refers to non aromatic carbocycles having 4 to 7 carbon atoms and having one or more double carbon bonds. Examples include cyclopentenyl, 1-methyl-cyclopentenyl, cyclohexenyl, 1,3-cyclopentadienyl, 1,3-cyclohexadienyl and 1,4-cyclohexadienyl.

As used herein the term "$C_{2-12}$ alkynyl" refers to $C_{2-12}$ straight or branched non-cyclic hydrocarbon containing one or more triple bonds, for instance, one or two triple bonds. Examples include 2-propynyl and 2- or 3-butynyl.

The term "aryl $C_{1-12}$ alkyl" refers to carbocyclic aromatic rings or ring systems as previously described and substituted by a $C_{1-12}$ alkyl group, also as previously described. Likewise the terms "aryl $C_{2-12}$ alkenyl" and "aryl $C_{2-12}$ alkynyl" refer to carbocyclic aromatic rings or ring systems as previously described and substituted by a $C_{2-12}$ alkenyl or $C_{2-12}$ alkynyl group, as previously described.

The aryl group and the alkyl, alkenyl or alkynyl group may be optionally substituted. In an embodiment the aryl group is not optionally substituted.

In another embodiment the alkyl, alkenyl or alkynyl group is optionally substituted. In a further embodiment the substituent is selected from halogen, —CN, —NR'R", —COR, —COOR, or —CONR'R". R, R' and R" may be independently selected from hydrogen or lower alkyl.

As used herein the term "halo" or "halogen" refers to fluoro, chloro, bromo and iodo groups.

As used herein a "halo alkyl" group has one or more of the hydrogen atoms on an alkyl group replaced with halogens. An example includes —$CF_3$.

In an embodiment compounds of the invention include those compounds where A is a bivalent link of 3 or 4 atoms selected from C, N, O and S. In that arrangement A and the atoms to which they are attached together form an aromatic ring having five or six ring atoms. When the linking atoms are all carbon, the ring formed is a carbocyclic aromatic ring or ring system. When the linking atoms include one or more of N, O or S then the ring formed is an aromatic heterocyclic ring. Examples include where the substructure

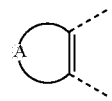

is:—

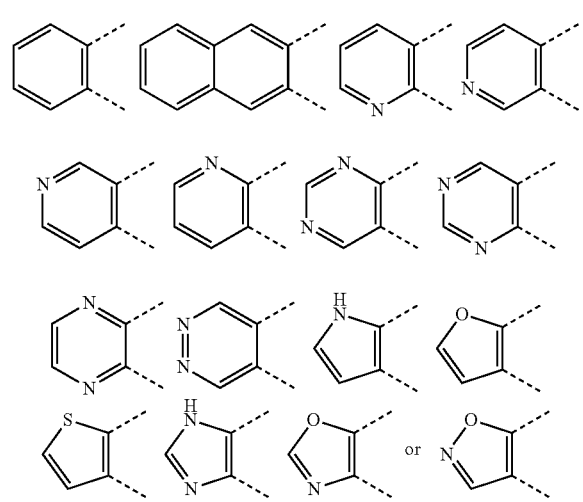

In another embodiment ring A is an optionally substituted aryl or heteroaryl ring, such as a phenyl, pyridyl, pyridazinyl, pyrimidinyl or pyrazinyl ring, and in a further embodiment selected from a phenyl or pyridyl ring. The optionally substituents include N-oxides of the ring nitrogen atoms.

The aromatic rings may be optionally substituted, for instance, by no more than 3 substituents. In an embodiment the aromatic rings may have 1 to 3 substituents selected from halo, lower alkyl, halogenated forms of lower alkyl, hydroxy, lower alkoxy, nitro, amino, loweralkylamino, carboxy, carboxamido, phenyl and benzyl. N-oxide forms of the nitrogen atoms of nitrogen containing rings are also contemplated. When A is a pyridyl ring, the ring nitrogen may be in an N-oxide form, or the ring may be in the form of a pyridinium salt.

In an embodiment ring A is an unsubstituted phenyl ring.

In another embodiment ring A is an unsubstituted pyridyl ring.

In respect of the heterocyclic ring formed by B—C, it will be understood that this ring can not be selected from all of the heterocyclic rings discussed earlier in relation to the meaning of the term due to the atoms to which B—C are attached. This ring is limited to monocyclic, non-aromatic heterocyclic rings that include at least two nitrogen atoms. The ring may include additional hetero atoms and may be partially unsaturated.

In another embodiment B—C represents a bivalent link of 1 to 3 atoms. The link B—C together with the atoms to which it is attached forms a non-aromatic heterocyclic ring. Examples include where the substructure:—

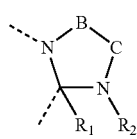

is:

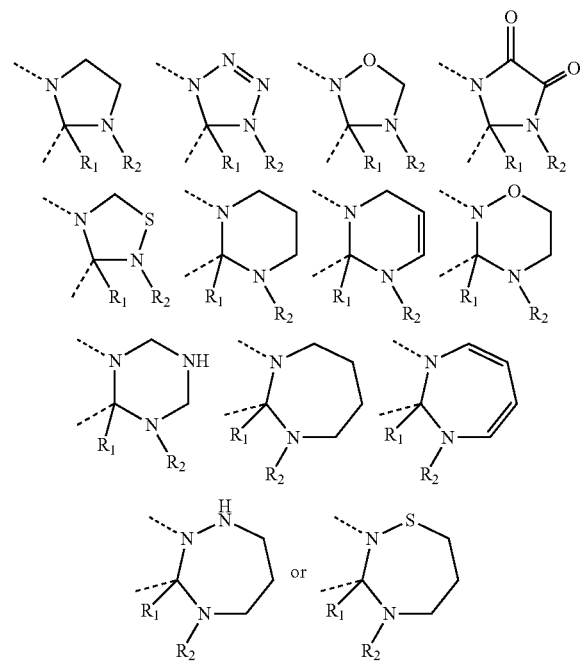

In a further embodiment, B—C represents —CH$_2$—(CH$_2$)$_z$—, where z is 1-4, such as 1, 2 or 3. In yet a further embodiment z is 1 or 2.

The atoms forming the link B—C may be optionally substituted, for instance, by no more than 3 substituents. A broad range of substituents are possible and include halo, lower alkyl, hydroxy, lower alkoxy, phenyl and benzyl.

In another embodiment B—C represents —CH$_2$CH$_2$—.

In an embodiment fused ring A and the ring containing the bivalent link B—C are optionally substituted with one or two substituents independently selected from halogen and C$_{1-6}$ alkyl. In a further embodiment fused ring A and the ring containing the bivalent link B—C are not substituted.

The bivalent linking D group together with the atoms to which it is attached can form a 6, 7, or 8 membered non-aromatic heterocyclic ring with a —C(=X)—N< moiety as represented by the following substructure:

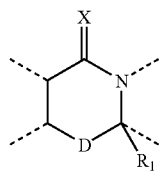

Examples include:

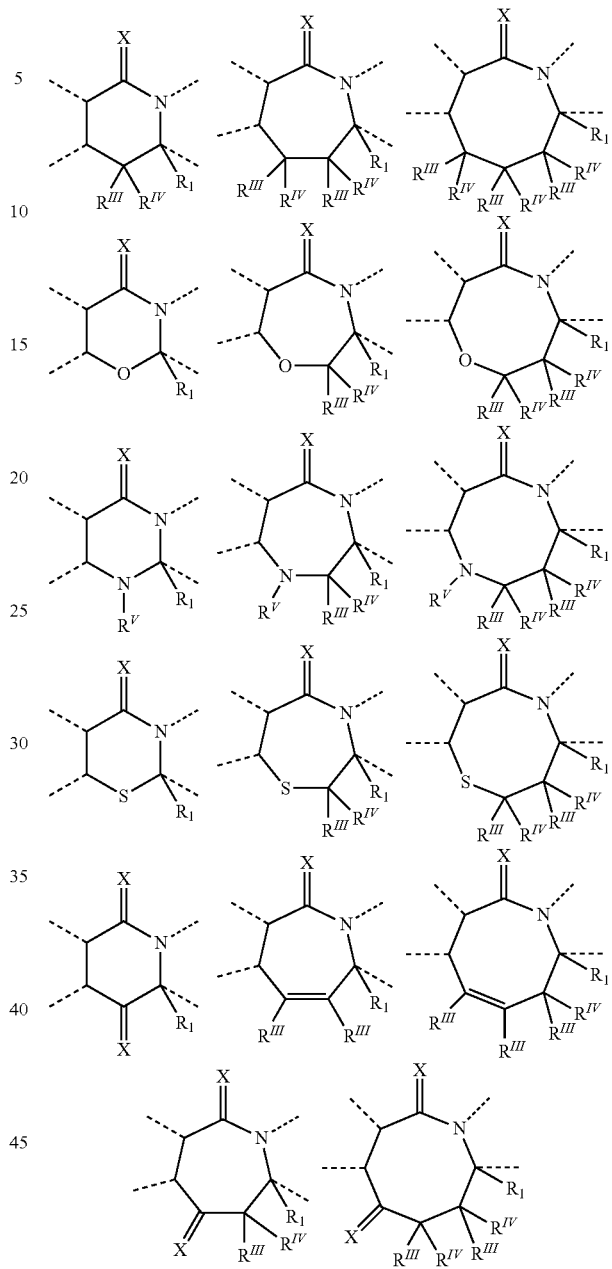

Accordingly, possible D groups include —CR$^{III}$R$^{IV}$—, —O—, —NR$^V$—, —S—, —C(=X)—, —CR$^{III}$R$^{IV}$CR$^{III}$R$^{IV}$—, —O—CR$^{III}$R$^{IV}$—, —NR$^V$—CR$^{III}$R$^{IV}$—, —S—CR$^{III}$R$^{IV}$—, —CR$^{III}$=CR$^{III}$—, —C(=X)—CR$^{III}$R$^{IV}$—, —CR$^{III}$R$^{IV}$—CR$^{III}$R$^{IV}$—CR$^{III}$R$^{IV}$—, —O—CR$^{III}$R$^{IV}$—CR$^{III}$R$^{IV}$—, —NR$^V$—CR$^{III}$R$^{IV}$—CR$^{III}$R$^{IV}$—, —S—CR$^{III}$R$^{IV}$—CR$^{III}$R$^{IV}$—, —CR$^{III}$=CR$^{III}$—CR$^{III}$R$^{IV}$—, and —C(=X)—CR$^{III}$R$^{IV}$—CR$^{III}$R$^{IV}$—;

wherein each R$^{III}$ and R$^{IV}$ are independently selected from hydrogen, halogen, hydroxyl, C$_{1-12}$ alkyl, C$_{2-12}$ alkenyl, C$_{2-12}$ alkynyl, —(CH$_2$)$_n$C$_{3-7}$ cycloalkyl, —(CH$_2$)$_n$C$_{4-7}$ cycloalkenyl, —(CH$_2$)$_n$ aryl, —(CH$_2$)$_n$ arylC$_{1-12}$ alkyl, —(CH$_2$)$_n$ arylC$_{2-12}$ alkenyl, —(CH$_2$)$_n$arylC$_{2-12}$ alkynyl, and —(CH$_2$)$_n$ heterocyclyl, or R$^{III}$ and R$^{IV}$ together with the atom to which they are attached represent a 3 to 7 membered cycloalkyl or heterocyclic ring; n is 0-6 and said alkyl, alkenyl, alkynyl, cycloalkyl, cycloalkenyl, aryl and heterocyclyl groups are optionally substituted;

$R^V$ is selected from O, —$CH_2R_3$, —$C(=Y)R_3$, —$C(=Y)OR_3$, —$C(=Y)N(R_4)R_3$, —$C(=Y)CH_2N(R_4)R_3$, —$C(=Y)CH_2SR_3$ and —$S(O)_wR_5$, where $R_3$ is selected from hydrogen, $C_{1-12}$ alkyl, $C_{2-12}$ alkenyl, $C_{2-12}$ alkynyl, —$(CH_2)_mC_{3-7}$ cycloalkyl, —$(CH_2)_mC_{4-7}$ cycloalkenyl, —$(CH_2)_m$ aryl, —$(CH_2)_m$ aryl$C_{1-12}$ alkyl, —$(CH_2)_m$ aryl$C_{2-12}$alkenyl, —$(CH_2)_m$ aryl$C_{2-12}$ alkynyl and —$(CH_2)_m$ heterocyclyl; and when $R^V$ is —$CH_2R_3$, or —$C(=Y)R_3$, $R_3$ may also be selected from —S—$R_5$ and —O—$R_5$; m is 0-6; $R_4$ is hydrogen or $C_{1-6}$ alkyl; $R_5$ is $C_{1-6}$ alkyl, $C_{2-6}$ alkenyl, $C_{2-6}$ alkynyl, $C_{3-7}$ cycloalkyl, $C_{4-7}$ cycloalkenyl, benzyl, aryl or heterocyclyl; w is 0, 1 or 2, and the alkyl, alkenyl, alkynyl, cycloalkyl, cycloalkenyl, aryl and heterocyclyl groups are optionally substituted; and X and Y are independently selected from O, S and $NR_6$, where $R_6$ is independently selected from hydrogen, lower alkyl, hydroxy, and lower alkoxy.

It will be appreciated that where D represents, for example, the bivalent linking group —O—$CR^{III}R^{IV}$— both of the following substructures are contemplated:

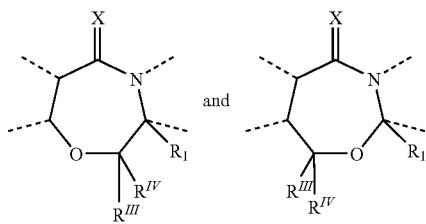

In an embodiment, the bivalent linking D group together with the atoms to which it is attached form a 6 membered non-aromatic heterocyclic ring.

In a further embodiment D represents —$CR^{III}R^{IV}$—, —O—, —$NR^V$—, —S—, or —C(=X)—.

In yet a further embodiment D represents —$CR^{III}R^{IV}$—, wherein:
(i) at least one of $R^{III}$ and $R^{IV}$ represents hydrogen and the other may be selected from halogen, hydroxyl, optionally substituted $C_{1-12}$ alkyl, and optionally substituted aryl;
(ii) $R^{III}$ and $R^{IV}$ are the same and represent $C_{1-3}$ alkyl; or
(iii) $R^{III}$ and $R^{IV}$ together with the atom to which they are attached represent a 3, 4, 5, 6 or 7 membered cycloalkyl or heterocyclyl ring.

In another embodiment D represents —$CR^{III}R^{IV}$—, wherein:
(i) $R^{III}$ and $R^{IV}$ are both H;
(ii) $R^{III}$ and $R^{IV}$ are both $CH_3$; or
(iii) $R^{III}$ and $R^{IV}$ together with the atom to which they are attached represent a 3-membered cycloalkyl ring or a symmetrical 6-membered heterocyclic ring.

In another embodiment X in the compounds of formula I and Ia is O.

In a further embodiment of the invention fused ring A, the ring containing the bivalent link B—C and the bivalent linking group D are all unsubstituted groups.

$R_1$ may be an optionally substituted aryl, alkyl or heterocyclyl. In an embodiment $R_1$ is an optionally substituted aryl or heterocyclyl group, such as a phenyl, thienyl, pyrrolyl or pyridyl ring. $R_1$ may also be a —$C_{1-6}$ alkylphenyl group. The rings of $R_1$ may be optional substituted with halo, hydroxy, nitro, —NR'R" (where R' and R" are independently selected from hydrogen, lower alkyl and —C(O)R, where R is $C_{1-6}$ alkyl, phenyl or heterocyclyl), $C_{1-12}$alkyl, phenyl and —O—$R_a$, where $R_a$ is —$C_{1-12}$alkyl, —$C_{3-7}$cycloalkyl, —$C_{1-12}$alkyl$C_{3-7}$cycloalkyl, phenyl or —$C_{1-12}$alkylphenyl; and the $C_{1-12}$alkyl, phenyl or $R_a$ group may be optionally substituted with halo, —CN, —NR'R", —$CO_2R$ or —CONR'R", where R, R' and R" are independently selected from hydrogen or lower alkyl. In a further embodiment, the ring is phenyl and is optionally substituted in the para or 4-position.

$R_1$ may be -phenyl substituted with $C_{1-10}$ alkyl chain, where the alkyl chain is substituted with halo, —CN, —NR'R", —$CO_2R$ or —CONR'R", where R, R' and R" are independently selected from hydrogen or lower alkyl. In an embodiment the alkyl chain is in the 4-position of the phenyl ring, and substituents are attached to the carbon at the free end of the alkyl group.

$R_1$ may be phenyl optionally substituted with a substituent selected from halo, —$C_{1-6}$alkyl, —$C_{1-6}$alkylhalo, —$C_{1-6}$alkylCN, —$OC_{1-6}$alkyl, —$OC_{1-6}$alkylhalo, —$OC_{1-6}$alkyl$CO_2NH_2$, —$OC_{1-6}$alkylCN, —$OC_{1-6}$alkyl$C_{3-7}$cycloalkyl, —$OC_{1-6}$alkyl$C_6H_5$, —$OC_{1-6}$alkyl$OCH_3$, —$OC_6H_5$, —$OC_6H_4$halo, —$CF_3$, —$OCF_3$, —NR'R" (where R' and R" are independently selected from hydrogen, —C(O)$C_{1-6}$alkyl, —C(O)$C_6H_5$, —C(O)CH=CHCO$_2$H, —C(O)$C_{1-6}$ alkyl$CO_2H$, —C(O)$C_{1-6}$alkyl$CO_2CH_3$, —C(O)$C_{1-6}$alkyl$C_6H_5$, —C(O)$C_{1-6}$alkyl$C_6H_4$—$CH_3$, —C(O)$C_{1-6}$alkyl$C_6H_4OCH_3$ and —C(O)$C_{1-6}$alkyl$C_6H_4$halo), —$CO_2H$, —$CO_2C_{1-6}$alkyl, —$NO_2$, —OH, —$C_6H_5$, —$C_6H_4C_{1-6}$alkyl, —$C_6H_4$halo and —OC(O)$C_{1-6}$alkyl.

In a further embodiment $R_1$ is optionally substituted phenyl where the substituents are each independently selected from halo, hydroxy or alkoxy; cycloalkyl; or optionally substituted pyridyl or an N-oxide thereof where the substituents are each independently selected from halo.

In a further embodiment $R_1$ is optionally substituted phenyl where the substituents are each independently selected from chloro, hydroxy or methoxy; lower cycloalkyl; or optionally substituted pyridyl or an N-oxide thereof where the substituents are each independently selected from chloro.

In yet a further embodiment $R_1$ is phenyl, 4-chlorophenyl, 4-methoxyphenyl, 4-hydroxyphenyl, 5-chloro-2-pyridyl, 4-pyridyl or 4-pyridyl N-oxide.

In another embodiment $R_1$ is unsubstituted phenyl or halophenyl. In a further embodiment $R_1$ is 4-chlorophenyl.

In a further embodiment $R_2$ is not hydrogen.

In yet a further embodiment the compounds are represented by formula Ia.

In another embodiment, when $R_2$ is —$CH_2$—$R_3$, $R_3$ is —$(CH_2)_m$ aryl or —$(CH_2)_m$ heterocyclyl, where m is 0 to 3. $R_3$ may be benzyl (m=1). The ring atoms may by optionally substituted with a broad range of substituents. Preferred substituents are selected from halo, lower alkyl, hydroxy, lower alkoxy and phenyl.

In another embodiment, when $R_2$ is —C(=Y)$CH_2N(R_4)R_3$ or —C(=Y)$CH_2SR_3$, $R_3$ is —$(CH_2)_m$ aryl or —$(CH_2)_m$ heterocyclyl where m is 0 to 3. The heterocycyl may itself be substituted with an oxo group, hydroxy or lower alkyl.

In yet another embodiment, when $R_2$ is —CON($R_4$)$R_3$, $R_4$ is hydrogen and $R_3$ is —$(CH_2)_m$ aryl or —$(CH_2)_m$ heteroaryl. In another embodiment m is 0 to 2, and preferably 0 or 1. The aryl and heteroaryl ring atoms may be optionally substituted with a broad range of substituents. In the above embodiment the substituents may include halo, lower alkyl, hydroxy, lower alkoxy and phenyl.

In another embodiment $R_2$ is —C(=Y)—$R_3$, when Y is O. In another embodiment $R_3$ is —$(CH_2)_m$ aryl or —$(CH_2)_m$ heteroaryl, when m is 0 to 3. In another embodiment $R_3$ is an optionally substituted aryl or optionally substituted heterocycle (m=0), and more preferably an optionally substituted 5 or 6 membered monocyclic heterocycle or an optionally substituted 9 or 10 membered bicyclic heterocycle or an optionally substituted aryl group.

In the above embodiments $R_3$ may be phenyl, naphthyl, furyl, thienyl, pyrrolyl, H-pyrrolyl, pyrrolinyl, pyrrolidinyl, oxazolyl, oxadiazolyl, (including 1,2,3 and 1,2,4 oxadiazolyls) thiazolyl, isoxazolyl, furazanyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), pyridyl, pyrimidinyl, pyridazinyl, pyranyl, pyrazinyl, piperidinyl, 1,4-dioxanyl, morpholinyl, 1,4-dithianyl, thiomorpholinyl, piperazinyl, 1,3,5-trithianyl, triazinyl, 1H thieno[2,3-c]pyrazolyl, thieno[2,3-b]furyl, indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, uridinyl, purinyl, cinnolinyl, phthalazinyl, quinazolinyl, quinoxalinyl, benzotriazinyl, naphthyridinyl or pteridinyl.

The heterocyclic ring may be fused to a carbocyclic ring such as phenyl, naphthyl, indenyl, azulenyl, fluorenyl, and anthracenyl.

The aryl or heterocyclic may be optionally substituted with a broad range of substituents, and preferably with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, nitro, cyano and mono or di($C_{1-6}$alkyl)amino. The substituents also include phenyl, benzyl and heterocyclyl.

In an embodiment $R_3$ is selected from phenyl, furyl, thienyl, pyridyl, oxazolyl, thiazolyl, pyrazolyl, furazanyl, isoxazolyl, isothiazolyl, 1,2,3-triazolyl, 1,3,4-triazolyl, 1,2,3-thiadiazolyl, 1,3,4-thiadiazolyl, pyridazinyl, pyrimidinyl, benzo[b]furanyl, benzo[b]thiophenyl and benzoisoxazolyl (which may be optionally substituted).

In an embodiment $R_2$ is —$CH_2R_3$, —$C(\!\!=\!\!O)R_3$, —$C(\!\!=\!\!O)N(R_4)R_5$ or —$SO_2R_6$; where
 a. $R_3$ is optionally substituted alkyl where the substituents are independently selected from —COOH, —$SCH_2CONHaryl$, —$NHSO_2aryl$, heteroaryl and aryl, each optionally independently substituted with halo or alkoxy; optionally substituted phenyl where the substituents are independently selected from halo; optionally substituted 5- or 6-membered heteroaryl where the substituents are independently selected from halo, alkyl, haloalkyl, cycloalkyl, aryl, heteroaryloxy, and heteroaryl optionally substituted with alkyl or haloalkyl; or optionally substituted alkenyl where the substituents are independently selected from heteroaryl;
 b. $R_4$ is H;
 c. $R_5$ is cycloalkyl, heteroaralkyl, alkyl or aralkyl; and
 d. $R_6$ is heteroaryl.

In a further embodiment $R_2$ is —$CH_2R_3$, —$C(\!\!=\!\!O)R_3$, —$C(\!\!=\!\!O)N(R_4)R_5$ or —$SO_2R_6$; where
 a. $R_3$ is optionally substituted methyl, ethyl, or propyl, where the substituents are independently selected from —COOH, —$SCH_2CONH$-3,4-dimethoxyphenyl, —$NHSO_2$-4-fluorophenyl, pyridyloxy, benzisoxazolyl, pyridyl, furyl, 4-fluorophenyl, or 4-methoxyphenyl; optionally substituted phenyl where the substituents are independently selected from methoxy, F and Cl; optionally substituted thiazolyl, pyridyl, furyl, thienyl, isoxazolyl, isothiazolyl, 1,2,3-thiadiazolyl, or pyrazolyl where the substituents are independently selected from pyridyloxy, cyclopropyl, Me, $CF_3$, phenyl, thienyl, pyridyl, F, Cl, Br, 5-$CF_3$-3-methyl-1-pyrazolyl; or 2-furylethen-1-yl;
 b. $R_4$ is H;
 c. $R_5$ is 2-pheneth-1-yl, benzyl, cyclohexyl, 2-furylmethyl, methyl, or 4-methylbenzyl; and
 d. $R_6$ is pyridyl.

In another embodiment of the invention $R_2$ is —$COR_3$, fused ring A is an optionally substituted phenyl or optionally substituted pyridyl ring (including N-oxides and pyridinium salts thereof), and D is —$CR^{III}R^{IV}$—.

In yet another embodiment, when the invention relates to compounds of formula I or formula Ia per se, $R_1$ is an optionally substituted phenyl, X is O, A together with the atoms to which it is attached forms an optionally substituted phenyl or optionally substituted pyridyl ring (including N-oxides and pyridinium salts thereof), B—C is —$CH_2CH_2$—, D is —$CH_2$— and $R_2$ is —$C(O)$ optionally substituted aryl or —$C(O)$ optionally substituted heterocyclyl.

It will be appreciated that compounds of formulae I and Ia and some derivatives thereof may have at least one asymmetric centre, and therefore are capable of existing in more than one stereoisomeric form. The invention extends to each of these forms individually and to mixtures thereof, including racemates. The isomers may be separated by conventional chromatographic methods or using a resolving agent. Alternatively the individual isomers may be prepared by asymmetric synthesis using chiral intermediates.

For instance, it will be appreciated that the compounds of the present invention will be chiral by virtue of the non-equivalent substituent pattern around the C-atom which bears the $R_1$ substituent. Accordingly, the compounds of the present invention may be presented as mixtures of enantiomers, for instance, enantiomerically enriched mixtures or racemic mixtures. Preferably, however, the compounds of the present invention are "enantiomerically pure."

As used herein with reference to an enantiomer the term "enantiomerically pure" means that the enantiomer is substantially free of its enantiomeric pair. Enantiomeric purity is generally expressed in terms of enantiomeric excess or % e.e. For a pair of enantiomers [(+) and (−)] wherein the mixture of the two is given as the mole or weight fractions $F_{(+)}$ and $F_{(-)}$ (wherein $F_{(+)}+F_{(-)}=1$) the enantiomeric excess is defined as $|F_{(+)}-F_{(-)}|$. Accordingly, the percentage e.e. is expressed by $100\times|F_{(+)}-F_{(-)}|$. As used herein the term "enantiomerically pure" refers to an enantiomer having a % e.e. of greater than 70%. Preferably the enantiomerically pure enantiomer has a % e.e. of greater than 80%, more preferably greater than 90%, and most preferably greater than 95%.

The preferred stereoisomer of compounds of formula I which contains a stereogenic centre at the point of attachment of $R_1$ is depicted by the structure below.

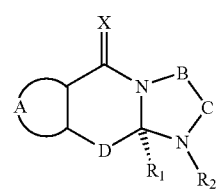

It will be appreciated by those skilled in the art that the absolute configuration (R or S) designation depends on the priority sequence of each group attached to the stereogenic centre according to the Cahn-Ingold-Prelog system.

Where the compound has at least one carbon-carbon double bond, it may occur in Z- and E-forms and all isomeric forms of the compounds are included in the present invention.

The salts of the compounds of formulae I and Ia are preferably pharmaceutically acceptable, but it will be appreciated that non-pharmaceutically acceptable salts also fall within the scope of the present invention, since these are useful as intermediates in the preparation of pharmaceutically acceptable salts.

It will be appreciated that pharmaceutically acceptable derivatives of the compounds of formulae I and Ia and the salts thereof, are also within the scope and spirit of the invention. Such derivatives includes pharmaceutically acceptable esters, prodrugs, solvates and hydrates of the compounds or their salts. Pharmaceutically acceptable derivatives may include any solvate, hydrate or any other compound or prodrug which, upon administration to a subject, is capable of providing (directly or indirectly) a compound of formula I or an antivirally active metabolite or residue thereof.

The pharmaceutically acceptable salts include acid addition salts, base addition salts, salts of pharmaceutically acceptable esters and the salts of quaternary amines and pyridiniums. The acid addition salts are formed from a compound of the invention and a pharmaceutically acceptable inorganic or organic acid including but not limited to hydrochloric, hydrobromic, sulfuric, phosphoric, methanesulfonic, toluenesulphonic, benzenesulphonic, acetic, propionic, ascorbic, citric, malonic, fumaric, maleic, lactic, salicyclic, sulfamic, or tartartic acids. The counter ion of quarternary amines and pyridiniums include chloride, bromide, iodide, sulfate, phosphate, methansulfonate, citrate, acetate, malonate, fumarate, sulfamate, and tartate. The base addition salts include but are not limited to salts such as sodium, potassium, calcium, lithium, magnesium, ammonium and alkylammonium. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others. The salts may be made in a known manner, for example by treating the compound with an appropriate acid or base in the presence of a suitable solvent.

The compounds of the invention may be in crystalline form either as the free compounds or as solvates (e.g. hydrates) and it is intended that both forms are within the scope of the present invention. Methods of solvation are generally known within the art.

The term "solvate" is a complex of variable stoichiometry formed by a solute (in this invention, a compound of the invention) and a solvent. Such solvents preferably do not interfere with the biological activity of the solute. Solvents may be, by way of example, water, ethanol or acetic acid. Methods of solvation are generally known within the art.

The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester derivative or a ring nitrogen atom is converted to an N-oxide. Examples of ester derivatives include alkyl esters, phosphate esters and those formed from amino acids, preferably valine. Any compound that is a prodrug of a compound of the invention is within the scope and spirit of the invention. Conventional procedures for the preparation of suitable prodrugs according to the invention are described in text books, such as "Design of Prodrugs" Ed. H. Bundgaard, Elsevier, 1985.

The term "pharmaceutically acceptable ester" includes biologically acceptable esters of compound of the invention such as sulphonic, phosphonic and carboxylic acid derivatives.

Thus, in another aspect of the invention, there is provided a prodrug or pharmaceutically acceptable ester of a compound of formula I or Ia.

In another aspect of the invention, there is provided a pharmaceutical composition that comprises a therapeutically effective amount of one or more of the aforementioned anti-RSV compounds of formulae I and Ia, including pharmaceutically acceptable derivatives thereof, and optionally a pharmaceutically acceptable carrier or diluent.

Unless otherwise specified the terms "treatment" or "treating", in the context of a method or use of the invention, includes both therapeutic and prophylactic treatments.

In further aspect of the present invention, there is provided the use of a compound of formula I or Ia, or salt thereof for the treatment (therapeutic or prophylactic) of RSV infections.

Without wanting to be bound by theory it is believed that the compounds of the present invention exhibit favourable anti-RSV activity by inhibiting the RSV virus's fusion process.

In a further form of the invention there is provided a process for the production of compounds of formulae I and Ia. These compounds may be prepared using the procedure outlined in the following methods.

Scheme 1 depicts a general process for manufacture of compounds of formula III. Compounds of formula III are within the scope of the compounds of formula Ia where $R^2$ is H and serve as useful synthetic intermediates. Compounds of formula III may be prepared via appropriate starting materials of formula II.

Scheme 1

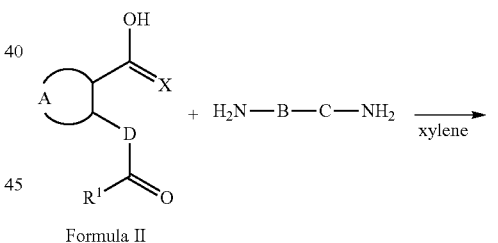

Formula II

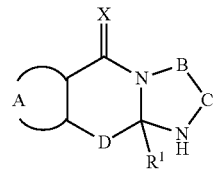

Formula III

In general, one equivalent of an appropriate keto-acid of formula II is reacted with approximately 3 equivalents of an appropriate diamine of the general formula H$_2$N—B—C—NH$_2$. The mixture is heated under reflux in an inert solvent, such as 1,2-dichloroethane, toluene or xylenes in a flask that may be fitted with a Dean-Stark apparatus for 3-24 h. A catalyst, such as an acid tosylate, can be used. After this time the reaction is allowed to cool and the product filtered and recrystallised from an appropriate solvent. If no precipitate forms the solvent is evaporated and the residue recrystallised or purified using flash chromatography or preparative HPLC.

Methods for the preparation of 2-(2'-oxo-2'-aryl)benzoic acids of formula II have been described by Guion T. S. et al., 1996, Synthetic Communications, 26:1753-1762, by Epsztajn, J. et al., Synth. Communications, 1992, 22:1239-1247, by Brugggink A. et al., Tetrahedron, 1975, 31:2607-2619 and by Ames, D. E. et al., 1976, J. Chem. Soc. Perkin Trans. 1, 1073-1078.

In a further aspect of the invention, new methods have been developed for the preparation of certain compounds of formula II and are described herein. Scheme 2 illustrates an example of a sequence that is useful for the manufacture of keto-acids of formula II (where X=O and D is —CH$_2$—). Generally, an appropriate aromatic o-halocarboxylic acid is suspended in tert-butanol or another suitable solvent with approximately 1.5 equivalents of an appropriate β-diketone. To this mixture is added approximately 0.25 equivalents of copper, copper (I) bromide or copper (I) iodide or both. The suspension is then treated with approximately 1.6 equivalents of potassium tert-butoxide or sodium ethoxide, sealed in a pressure-resistant vessel and heated in a microwave reactor with stirring at around 180° C. for approximately 1 hour. Alternatively, a solvent with a sufficiently high boiling point (such as N,N-dimethylacetamide) may be used and the mixture is heated at reflux in an open vessel until the substrate has been substantially converted. The resulting mixture is diluted with water, neutralised with aqueous NH$_4$Cl and extracted with a suitable organic solvent. The organic extracts are dried and concentrated and the residue may be purified by flash chromatography. The lactone intermediate is then hydrolysed by treatment with dilute aqueous hydroxide solution using acetonitrile as a co-solvent.

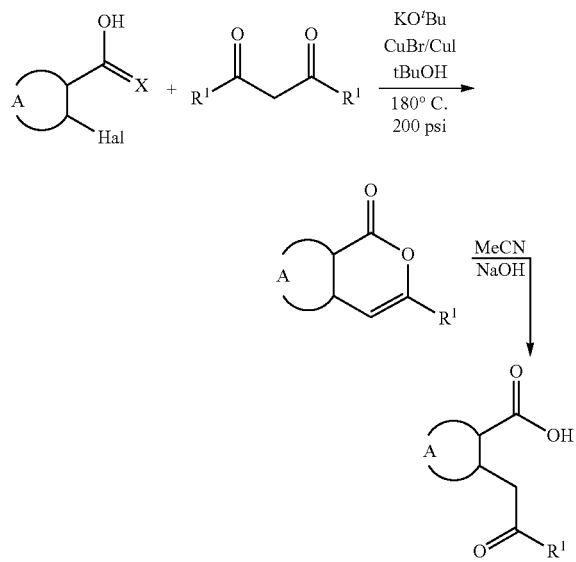

Scheme 2

Other compounds of formula II may be prepared by substitution of an α-methylene ketone. A suitable keto-acid of formula II (where X=O and D is —[CH$_2$]$_n$—) and a catalytic amount of 18-crown-6 are suspended in THF and cooled to −78° C. The selected alkyl halide or dihalide (approximately 3 equivalents) and then potassium t-butoxide are added. The mixture is stirred and allowed to warm to room temperature. When the reaction is complete, the mixture is cooled again and quenched with a saturated solution of ammonium chloride and diluted with a small amount of water. The organic layer is separated and washed with brine, dried over MgSO$_4$ and concentrated. The residue may be purified by recrystallisation or by flash chromatography. This method is an adaptation of procedures described in J. Org. Chem. 1991, 56:7188-7190.

Other compounds of formula I may be obtained by acylating compounds of formula III as illustrated in Scheme 3.

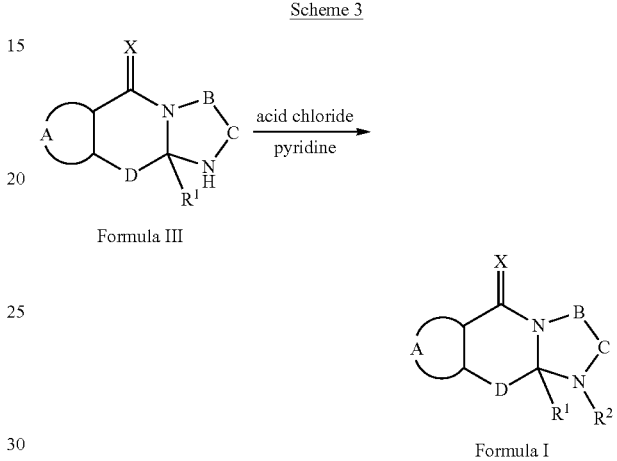

Scheme 3

In one method, two equivalents of diisopropylethylamine or triethylamine are added to one equivalent of a compound of formula III in THF at 0° C. An acid chloride, or other acylating agent, is added to the mixture and the reaction monitored by HPLC. When the reaction is complete the reaction is quenched with water and the product extracted into a suitable organic solvent and worked up according to standard methods. Similar acylation may also be carried out by reacting one equivalent of the compound of formula III with one equivalent of the appropriate acid chloride in xylene at 120° C. for 1-24 h. The reaction is then allowed to cool and the product isolated. Alternatively, compounds of formula III may be treated with approximately 2.2 equivalents of an appropriate acid chloride or anhydride in pyridine at approximately −5° C. The mixture is allowed to warm to room temperature and after stirring for 2-24 h the product is isolated by standard methods. Acylation may also be achieved by treating the appropriate compound of formula III with the appropriate carboxylic acid (3 equivalents), TFFH (3.3 equivalents) and DIEA (3.3 equivalents) in DMF and heating to 45° C. for approximately 14 days. After this time the product is isolated by standard methods.

N-alkylated and N-sulfonylated compounds of formula I are best obtained using suitable N-substituted diamines. These may be prepared by known methods for example that are described by Kruse L. I., et al., J. Med. Chem. 1990, 33, 781-789. The appropriate keto-acid (2 equivalents) and N-substituted diamine (1 equivalent) in chlorobenzene, toluene or xylene are placed in a flask equipped with a stirrer and Dean-Stark water separator and heated at reflux until no further water is seen to separate (1-8 h) (Scheme 4). The solvent is then removed and the residue can be purified using standard methods.

Scheme 4

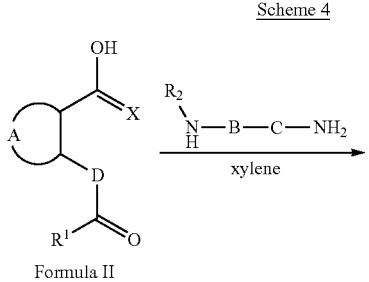

Formula II

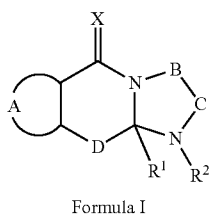

Formula I

To prepare compounds of formula I where R² is a urea or thiourea, one equivalent of the appropriate compound of formula III is reacted with one equivalent of the appropriate isocyanate or isothiocyanate in an inert solvent such as THF or xylene at a temperature ranging from 20-120° C. for 1-24 h. The reaction is then allowed to cool and the product is filtered, washed and either recrystallised from an appropriate solvent or purified using chromatography.

Other compounds of formula I can be prepared by the addition, removal or modification of existing substituents. This could be achieved by using standard techniques for functional group inter-conversion that are well known in the industry, such as those described in "Comprehensive organic transformations: a guide to functional group preparations" by Larock R. C., New York, VCH Publishers, Inc. 1989.

Examples of functional group inter-conversions are: —C(O)NR'R" from —CO₂CH₃ by heating with or without catalytic metal cyanide, e.g. NaCN, and HNR'R" in CH₃OH; —OC(O)R from —OH with e.g., ClC(O)R in pyridine; —NC(S)NR'R" from —NHR with an alkylisothiocyanate or thiocyanic acid; —NRC(O)OR' from —NHR with alkyl chloroformate; —NRC(O)NR'R" from —NHR by treatment with an isocyanate, e.g. HN=C=O or RN=C=O; —NRC(O)R' from —NHR by treatment with ClC(O)R' in pyridine; —C(=NR)NR'R" from —C(NR'R")SR with H₃NR⁺OAc⁻ by heating in alcohol; —C(NR'R")SR from —C(S)NR'R" with R—I in an inert solvent, e.g. acetone; —C(S)NR'R" (where R' or R" is not hydrogen) from —C(S)NH₂ with HNR'R"; —C(=NCN)—NR'R" from —C(—NR'R")—SR with NH₂CN by heating in anhydrous alcohol, alternatively from —C(=NH)—NR'R" by treatment with BrCN and NaOEt in EtOH; —NR—C(=NCN)SR from —NHR' by treatment with (RS)₂C=NCN; —NR"SO₂R from —NHR' by treatment with ClSO₂R by heating in pyridine; —NR'C(S)R from —NR'C(O)R by treatment with Lawesson's reagent [2,4-bis(4-methoxyphenyl)-1,3,2,4-dithiadiphosphetane-2,4-disulfide]; —NRSO₂CF₃ from —NHR with triflic anhydride and base, —CH(NH₂)CHO from —CH(NH₂)C(O)OR' with Na(Hg) and HCl/EtOH; —CH₂C(O)OH from —C(O)OH by treatment with SOCl₂ then CH₂N₂ then H₂O/Ag₂O; —C(O)OH from —CH₂C(O)OCH₃ by treatment with PhMgX/HX then acetic anhydride then CrO₃; R—OC(O)R' from RC(O)R' by R"CO₃H; —CCH₂OH from —C(O)OR' with Na/R'OH; —CHCH₂ from —CH₂CH₂OH by the Chugaev reaction; —NH₂ from —C(O)OH by the Curtius reaction; —NH₂ from —C(O)NHOH with TsCl/base then H₂O; —CHC(O)CHR from —CHCHOHCHR by using the Dess-Martin Periodinane regent or CrO₃/aqH₂SO₄/acetone; —C₆H₅CHO from —C₆H₅CH₃ with CrO₂Cl₂; —CHO from —CN with SnCl₂/HCl; —CN from —C(O)NHR with PCl₅; —CH₂R from —C(O)R with N₂H₄/KOH.

During the reactions a number of the moieties may need to be protected. Suitable protecting groups are well known in industry and have been described in many references such as Protective Groups in Organic Synthesis, Greene, T. W. and Wuts, P. G. M., Wiley-Interscience, New York, 1999 or Protecting Groups, Kocienski, P. J., Thieme, Stuttgart, 1994.

The abbreviations that may be used herein, included in Schemes 1 to 4, and the experimental section are as follows unless indicated otherwise:
DCM: dichloromethane
DIEA: diisopropylethylamine
DMF: dimethylformamide
Et: ethyl
EtOAc: ethyl acetate
Me: methyl
MeOH: methyl alcohol
MS: mass spectrometry
NMR: nuclear magnetic resonance
Ph: phenyl
HPLC: high performance liquid chromatography
TEA: triethylamine
TFA: Trifluoroacetic acid
TFFH: Fluoro-N,N,N'',N''-tetramethylformamidinium hexafluorophosphate
THF: tetrahydrofuran
TsCl: Tosyl chloride
TsOH: Toluenesulphonic acid The invention also pertains to therapeutic compositions for the prevention and/or treatment of RSV, containing at least one compound of formula I or Ia including pharmaceutical acceptable salts or prodrugs.

It is contemplated that the compositions of the invention may further contain or be administered with one or more other compounds having anti-viral activity in respect of RSV, such as Virazole®, or other agents such as RespiGam™ or Synagis®.

It is contemplated that the compositions of the invention may further contain or be administered in combination with other drugs to treat symptoms of the disease, such as for example anti-inflammatory medicaments, such as diclofenac, diflunisal, etodolac, fenoprofen, flurbiprofen, ibuprofen, indomethacin, ketoprofen, ketorolac, mefanamic acid, meloxicam, nabumetone, naproxen, oxaprozin, piroxicam, salsalate, sulindac, tolmetin.

It is contemplated that the compositions of the invention may further contain or be administered with other drugs to treat symptoms of the disease, such as for example, steroids such as short-acting beta-agonists: albuterol, levalbuterol, bitolterol, pirbuterol, terbutaline, ipratropium bromide, prednisone, prednisolone, and methylprednisolone; long-acting beta-agonists, such as salmeterol or formoterol; leukotriene modifiers, such as monoleukast, zafirlukast, and zileuton; theophyllines; nedocromils; and cromolyns.

The term "composition" is intended to include the formulation of an active ingredient with conventional carriers and excipients, and also with encapsulating materials as the carrier, to give a capsule in which the active ingredient (with or without other carriers) is surrounded by the encapsulation carrier.

As will be readily appreciated by those skilled in the art, the route of administration and the nature of the pharmaceutically acceptable carrier will depend on the nature of the condition and the animal to be treated. It is believed that the choice of a particular carrier or delivery system, and route of administration could be readily determined by a person skilled in the art. In the preparation of any formulation containing the compounds care can be taken to ensure that the activity of the compound is not destroyed in the process and that the compound is able to reach its site of action without being destroyed. In some circumstances it may be necessary to protect the compound by means known in the art, such as, for example, micro encapsulation. Similarly the route of administration chosen can be such that the compound reaches its site of action.

The pharmaceutical compositions or formulations include those suitable for oral, rectal, nasal, topical (including buccal and sub-lingual), vaginal or parenteral (including intramuscular, sub-cutaneous and intravenous) administration or in a form suitable for administration by inhalation or insufflation. It is envisaged that the compositions may be provided in a form suitable for oral or nasal administration or by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administrated in a wide variety of oral and parenteral dosage forms. It will be understood to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations may include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

For example, in powders, the carrier is a finely divided solid that is in a mixture with the finely divided active component.

For example, in tablets, the active component is mixed with the carrier having the necessary binding capacity in suitable proportions and compacted in the shape and size desired.

The powders and tablets preferably contain from five or ten to about seventy percent of the active compound. Suitable carriers may be magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized moulds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both.

The compositions according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, eg. sterile, pyrogen-free water, before use.

Pharmaceutical forms suitable for injectable use include sterile injectable solutions or dispersions, and sterile powders for the extemporaneous preparation of sterile injectable solutions. They can be stable under the conditions of manufacture and storage and may be preserved against oxidation and the contaminating action of microorganisms such as bacteria or fungi.

Those skilled in the art may readily determine appropriate formulations for the compounds of the present invention using conventional approaches. Identification of preferred pH ranges and suitable excipients, for example antioxidants, is routine in the art. Buffer systems are routinely used to provide pH values of a desired range and include carboxylic acid buffers for example acetate, citrate, lactate and succinate. A variety of antioxidants are available for such formulations including phenolic compounds such as BHT or vitamin E, reducing agents such as methionine or sulphite, and metal chelators such as EDTA.

The solvent or dispersion medium for the injectable solution or dispersion may contain any of the conventional solvent or carrier systems for the compounds, and may contain, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about where necessary by the inclusion of various antibacterial and antifungal agents, for example, parabens, chlorobutanol, phenol, sorbic acid, thimerosal and the like. In many cases, it will be preferable to include agents to adjust osmolality, for example, sugars or sodium chloride. Preferably, the formulation for injection will be isotonic with blood. Prolonged absorption of the injectable compositions can be brought about by the use in the compositions of agents delaying absorption, for example, aluminium monostearate and gelatin. Pharmaceutical forms suitable for injectable use may be delivered by any appropriate route including intravenous, intramuscular, intracerebral, intrathecal, epidural injection or infusion.

Sterile injectable solutions are prepared by incorporating the active compounds in the required amount in the appropriate solvent with various other ingredients such as these enumerated above, as required, followed by filtered sterilization. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, preferred methods of preparation are vacuum drying or freeze-drying of a previously sterile-filtered solution of the active ingredient plus any additional desired ingredients.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations preferably contain at least 1% by weight of active compound. The percentage of the compositions and preparations may, of course, be varied and may conveniently be between about 5 to about 80% of the weight of the unit. The amount of active compound in therapeutically useful compositions can be sufficient that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Any material used in preparing any dosage unit form can be pharmaceutically pure and substantially non-toxic in the amounts employed. In addition, the active compound(s) may be incorporated into sustained-release preparations and formulations, including those which allow specific delivery of the active peptide to specific regions of the gut.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except in so far as any conventional media or agent is incompatible with the active ingredient, use thereof in the therapeutic compositions is contemplated. Supplementary active ingredients can also be incorporated into the compositions.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronisation.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The invention also includes the compounds of formula I, Ia, II, in the absence of carrier where the compounds are in unit dosage form.

The amount of compound of formula I administered may be in the range from about 10 mg to 2000 mg per day, depending on the activity of the compound and the disease to be treated.

Liquids or powders for intranasal administration, tablets or capsules for oral administration and liquids for intravenous administration are the preferred compositions.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

EXPERIMENTAL

Synthetic Procedures $^1$H NMR spectra were recorded on either a Bruker Avance DRX 400, AC 200 or AM 300 spectrometer. Spectra were recorded in $CDCl_3$, $d_6$-acetone, $CD_3OD$ or $d_6$-DMSO using the residual solvent peak as a reference. Chemical shifts are reported on the δ scale in parts per million (ppm) using the following conventions to assign the multiplicity: s (singlet), d (doublet), t (triplet), q (quartet) m (multiplet) and prefixed b (broad). Mass spectra (ESI) were recorded on a Finnigan LCQ Advantage spectrometer. Flash chromatography was performed on 40-63 μm silica gel 60 (Merck No. 9385). Preparative HPLC was carried out using a Gilson 322 pump with a Gilson 215 liquid handler and a HP1100 PDA detector. Unless stated otherwise, HPLC systems employed Phenomenex C8(2) columns using water containing 0.1% TFA and either acetonitrile or acetonitrile containing 0.06% TFA.

Method A

One equivalent of an appropriate keto-acid of formula II or its ester analogue is reacted with approximately 3 equivalents of an appropriate diamine of the general formula $H_2N$—B—C—$NH_2$. The mixture is heated under reflux in an inert solvent, such as 1,2-dichloroethane, toluene or xylene, in a flask that may be fitted with a Dean-Stark apparatus for 1-24 h or until no more water is being collected in the trap. A catalyst, such as an acid tosylate, can be used. After this time the reaction is allowed to cool and the product filtered and recrystallised from an appropriate solvent. If no precipitate forms the solvent is evaporated in vacuo and the residue recrystallised or purified using flash chromatography or preparative HPLC.

This method for forming compounds of formula III is an adaptation of procedures described in U.S. Pat. No. 4,058, 529, Sulkowski, T. S., et al., 1967, J. Org. Chem., 32:2180-2184 and Houlihan, W. J., et al., 1975, J. Med. Chem., 18:182-185.

10a-(4-Chlorophenyl)-2,3,10,10a-tetrahydro-1H-imidazo[1,2-b]isoquinolin-5-one

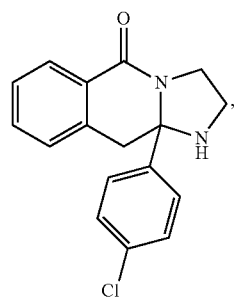 [SMILES: O=C1c2ccccc2CC2(c3ccc(Cl)cc3)NCCN12]

The isoquinolinone derivative above was prepared by Method A using ethylenediamine and 2-(benzoylmethyl)benzoic acid.

$^1$H NMR (300 MHz, d6-acetone) δ 2.58-2.70 (m, 1H), 3.27-3.36 (m, 1H), 3.43-3.52 (m, 1H), 3.46 (d, 1H, J 15.4 Hz), 3.53 (d, 1H, J 15.3 Hz), 3.68-3.79 (m, 1H), 7.05-7.10 (m, 1H), 7.24 (d, 2H, J 8.8 Hz), 7.29-7.34 (m, 2H), 7.32 (d, 2H, J 8.8 Hz), 7.93-7.97 (m, 1H).

ESI-MS m/z calculated [M+H]$^+$: 299.0; found: 298.9.

9a-(4-Chlorophenyl)-2,3,9,9a-tetrahydro-1H-1,3a,8-triazacyclopenta[b]naphthalen-4-one

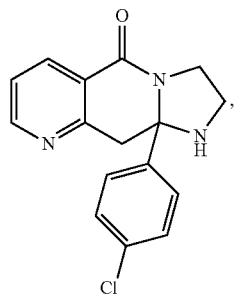 [SMILES: O=C1c2cccnc2CC2(c3ccc(Cl)cc3)NCCN12]

The polyaza-tetrahydronaphthalenone derivative above was prepared by Method A using ethylenediamine and 2-[2-(4-chlorophenyl)-2-oxoethyl]-nicotinic acid.

$^1$H NMR (300 MHz, d6-acetone) δ 3.33-3.79 (m, 6H), 7.26-7.36 (m, 5H), 8.21 (dd, 1H), 8.48 (dd, 1H).

ESI-MS m/z calculated [M+H]$^+$: 300.0; found: 299.9.

Method B

Two equivalents of diisopropylethylamine or triethylamine are added to one equivalent of a compound of formula III in THF or other suitable inert solvent at 0° C. An isocyanate, isothiocyanate, acid chloride or other acylating agent is added to the mixture and the reaction monitored by HPLC. When complete, the reaction is quenched with water and the product extracted into EtOAc. The EtOAc is subsequently washed with solutions of 1:1 sat. NH$_4$Cl$_{(aq)}$/water, 1:1 sat. Na$_2$CO$_{3(aq)}$/water and sat. Na$_2$CO$_{3(aq)}$. The EtOAc is dried (Na$_2$SO$_4$ or MgSO$_4$), the solvent evaporated in vacuo and the residue either crystallised or purified by flash chromatography or by preparative HPLC.

N-{2-[10a-(4-Chlorophenyl)-5-oxo-2,3,10,10a-tetrahydro-5H-imidazo[1,2-b]isoquinolin-1-yl]-2-oxoethyl}-4-fluorobenzenesulfonamide

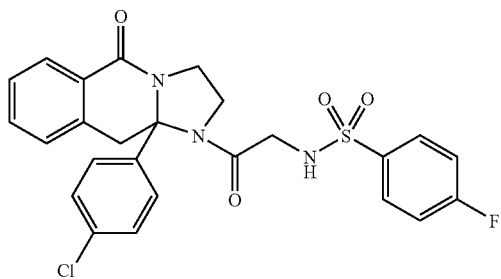 [SMILES: O=C(CNS(=O)(=O)c1ccc(F)cc1)N1CCN2C(=O)c3ccccc3CC12c1ccc(Cl)cc1]

The amide above was prepared by Method B using 4-(fluorobenzenesulfonylamino)acetyl chloride and triethylamine in dichloromethane and purified by flash chromatography.

$^1$H NMR (300 MHz, CDCl$_3$) δ 3.39 (d, 1H, J 15 Hz), 3.54-3.62 (m, 1H), 3.66-3.89 (m, 4H), 4.44 (d, 1H, J 16 Hz), 4.44-4.53 (m, 1H), 5.48-5.51 (m, 1H), 7.13-7.33 (m, 8H), 7.37-7.42 (m, 1H), 7.86-7.91 (m, 2H), 7.97 (dd, 1H, J 7.5 Hz, 1.3 Hz).

ESI-MS m/z calculated [M+H]$^+$: 514.0; found: 514.0.

Method C

One equivalent of the appropriate compound of formula III is allowed to react with one equivalent of the appropriate acid chloride or alternative acylating agent in a suitable inert solvent, such as toluene, in the presence of a non-nucleophilic base, such as triethylamine, at elevated temperature until the reaction is substantially complete. An acyl transfer reagent, such as N,N-dimethyl-4-aminopyridine, may also be added to the reaction mixture. The mixture is then allowed to cool and the product filtered and recrystallised from an appropriate solvent. If no precipitate is formed the reaction is purified using flash chromatography or preparative HPLC.

4-[10a-(4-Chlorophenyl)-5-oxo-2,3,10,10a-tetrahydro-5H-imidazo[1,2-b]isoquinolin-1-yl]-4-oxobutyric acid

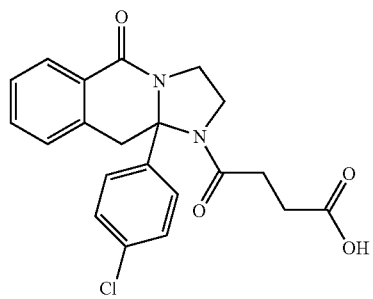 [SMILES: O=C(O)CCC(=O)N1CCN2C(=O)c3ccccc3CC12c1ccc(Cl)cc1]

The amide above was prepared by Method C using succinic anhydride and triethylamine with N,N-dimethyl-4-aminopyridine in toluene at reflux for 3 days and purified by flash chromatography.

$^1$H NMR (300 MHz, CDCl$_3$) δ 2.57-2.60 (m, 2H), 2.64-2.67 (m, 2H), 3.55 (d, 1H, J 16 Hz), 3.76-3.84 (m, 2H), 3.96-4.06 (m, 1H), 4.43-4.52 (m, 1H), 4.60 (d, 1H, J 16 Hz), 7.12-7.20 (m, 3H), 7.28-7.40 (m, 4H), 7.96 (dd, 1H, J 7.6 Hz, 1.2 Hz).

ESI-MS m/z calculated [M+H]$^+$: 399.0; found: 399.0.

Method D

N-substituted diamines may be prepared according to methods that will be well known to persons skilled in the art. One such procedure is outlined in Kruse L. I., et al., 1990, J. Med. Chem., 33:781-789.

An appropriate compound of Formula II (2 equivalents) and N-substituted diamine of formula H$_2$N—B—C—NHR$^3$ (1 equivalent) in toluene, xylene or other suitable inert solvent are placed in a flask equipped with a stirrer and Dean-Stark apparatus. The mixture is heated to reflux until no further water is separating (typically 1-24 h). The solvent is then distilled off and the residue cooled. The residue is purified using flash chromatography or preparative HPLC.

10a'-(4'-Chlorophenyl)-1'-(4'-fluorobenzyl)-2',3',10'10a'-tetrahydro-1'H-spiro[cyclopropane-(1,10'-imidazo[1,2-b]isoquinolin[5]one)]

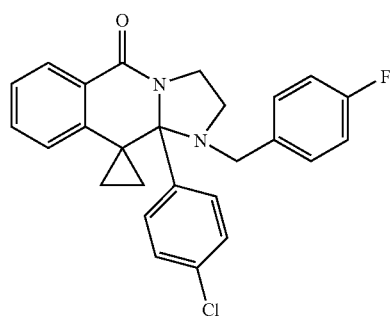 [SMILES: O=C1c2ccccc2C2(CC2)C2(c3ccc(Cl)cc3)N(Cc3ccc(F)cc3)CCN12]

The amide above was prepared by Method D using N-(4-fluorobenzyl)ethylenediamine in xylenes at reflux for 21 h and purified by flash chromatography.

$^1$H NMR (300 MHz, CDCl3) δ 0.42-0.49 (m, 1H), 1.56-1.64 (m 1H), 1.76-1.82 (m, 1H), 1.92-1.99 (m, 1H), 2.36 (d, 1H, J 14 Hz), 2.55-2.65 (m, 1H), 3.19-3.25 (m, 1H), 3.71 (d, 1H, J 14 Hz), 3.83-3.93 (m, 1H), 4.12-4.19 (m, 1H), 6.97-7.05 (m, 3H), 7.13-7.21 (m, 5H), 7.25-7.35 (m, 3H), 7.84 (dd, 1H, J 7.6 Hz, 1.3 Hz).

ESI-MS m/z calculated [M+H]$^+$: 433.0; found: 433.1.

Method E

One equivalent of the appropriate compound of formula III is reacted with one equivalent of the appropriate isocyanate or isothiocyanate in THF or xylene at a temperature ranging from 20-120° C. for 1-48 h. The reaction is then allowed to cool and the product filtered, washed and recrystallised from an appropriate solvent. If no precipitate forms then the product may be purified using flash chromatography or preparative HPLC.

Method F

The appropriate isocyanate, isothiocyanate, sulfonyl chloride, acid chloride, anhydride or alternative acylating agent (2.2 eq) is added directly for liquids or as a solution in pyridine (~1M) for solids to a solution of the appropriate compound of formula III (0.1 mmol) in pyridine (500 μL) at −5° C. The reaction is stirred and allowed to warm to room temperature for 2-24 h. The reaction is subsequently diluted with water and extracted three times with CH$_2$Cl$_2$ or other suitable organic solvent. The combined organic extracts are washed with 1N NaOH (3×) and 10% HCl (3×). In the case of basic products the acid wash is omitted and in the case of acidic products the basic wash is omitted. For neutral or basic products the crude purity may be improved by stirring the combined CH$_2$Cl$_2$ extract in the presence of a polymer-supported base (such as MP-carbonate resin, Argonaut Technologies Inc.) for 0.5-12 h. The CH$_2$Cl$_2$ extracts are dried (MgSO$_4$) and the solvent evaporated in vacuo. The crude products are subsequently purified by flash chromatography.

10a-(4-Chlorophenyl)-1-(pyridine-3-carbonyl)-2,3,10,10a-tetrahydro-1H-imidazo[1,2-b]isoquinolin-5-one

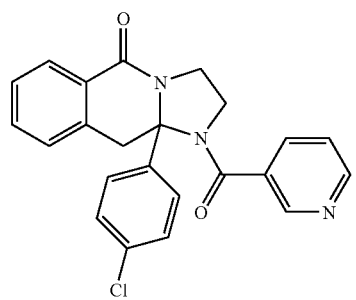 [SMILES: O=C(c1cccnc1)N1CCN2C(=O)c3ccccc3CC12c1ccc(Cl)cc1]

The acylated isoquinolinone derivative above was prepared by Method F using nicotinoyl chloride and 10a-(4-chlorophenyl)-2,3,10,10a-tetrahydro-1H-imidazo[1,2-b]isoquinolin-5-one.

$^1$H NMR (300 MHz, d6-acetone) δ 3.78-3.88 (m, 3H), 3.97-4.09 (m, 1H), 4.28-4.38 (m, 1H), 4.72 (d, 1H, J 16.0 Hz), 7.29 (d, 2H, J 8.9 Hz), 7.31-7.38 (m, 1H), 7.41-7.52 (m, 3H), 7.58 (d, 2H, J 8.9 Hz), 7.87-7.91 (m, 1H), 7.92 (ddd, 1H, J 1.7 Hz, J 2.2 Hz, J 7.9 Hz), 8.67 (dd, 1H, J 1.7 Hz, J 4.9 Hz), 8.73 (dd, 1H, J 0.9 Hz, J 2.2 Hz).

ESI-MS m/z calculated [M+H]$^+$: 404.0; found: 404.1.

10a-(4-Chlorophenyl)-1-(2-pyridin-2-yl-acetyl)-2,3,10,10a-tetrahydro-1H-imidazo[1,2-b]isoquinolin-5-one

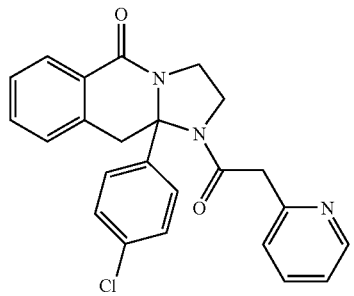 [SMILES: O=C(Cc1ccccn1)N1CCN2C(=O)c3ccccc3CC12c1ccc(Cl)cc1]

The acylated isoquinolinone derivative above was prepared by Method F. Pyridin-2-yl-acetic acid was pre-activated by treatment with one equivalent of O-benzotriazole-N,N,N',N'-tetramethyl-uronium-hexafluoro-phosphate in a DMF/pyridine solution. After 10 minutes, this solution was added to 10a-(4-chlorophenyl)-2,3,10,10a-tetrahydro-1H-imidazo[1,2-b]isoquinolin-5-one.

$^1$H NMR (300 MHz, CD$_2$Cl$_2$) δ 3.57 (d, 1H, J 16.0 Hz), 3.73-3.96 (m, 4H), 4.04-4.12 (m, 1H), 4.37-4.45 (m, 1H), 4.63 (d, 1H, J 16.0 Hz), 7.16-7.46 (m, 9H), 7.68 (ddd, 1H, J 7.7 Hz, 7.7 Hz, 1.8 Hz), 7.92 (dd, 1H, J 7.7 Hz, 1.8 Hz), 8.52 (d, 1H, J 4.9 Hz).

ESI-MS m/z calculated [M+H]$^+$: 418.0; found: 418.0.

Method G

This method is an adaptation of the method described by Copéret, C. et al., J. Org. Chem., 1998, 63, 1740-1741. 30% Hydrogen peroxide (10 eq) is added to a solution of either an appropriate compound of formula I or formula III (1 eq) and trioxorhenium 2.5 mol % in CH$_2$Cl$_2$ (4× volume of hydrogen peroxide solution) at ambient temperature. The mixture is stirred overnight after which time the mixture is diluted with water and stirred for a further 30 minutes. After this time the CH$_2$Cl$_2$ is separated and the aqueous layer extracted further with CH$_2$Cl$_2$ (2×). The combined extracts are dried and the solvent evaporated in vacuo to yield the desired product, which may be purified by crystallisation or chromatography as required.

9a-(4-Chlorophenyl)-1-(furan-3-carbonyl)-8-oxy-2,3,9,9a-tetrahydro-1H-1,3a,8-triazacyclopenta[b]naphthalen-4-one

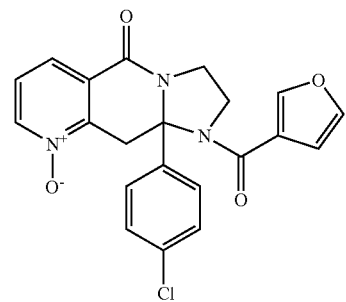 [SMILES: O=C(c1ccoc1)N1CCN2C(=O)c3ccc[n+]([O-])c3CC12c1ccc(Cl)cc1]

The oxygenated derivative above was prepared by Method G from 10a-(4-chlorophenyl)-2,3,10,10a-tetrahydro-1H-imidazo[1,2-b]isoquinolin-5-one.

$^1$H NMR (300 MHz, d6-acetone) δ 3.38 (d, 1H, J 17.8 Hz), 3.93-4.02 (m, 1H), 4.24-4.35 (m, 2H), 4.37-4.56 (m, 1H), 5.46 (d, 1H, J 17.8 Hz), 6.76-6.77 (m, 1H), 7.26 (d, 2H, J 8.7 Hz), 7.35-7.39 (m, 1H), 7.41 (d, 2H, J 8.7 Hz), 7.59-7.61 (m, 1H), 7.64 (d, 1H, J 7.9 Hz), 8.07-8.08 (m, 1H), 8.33 (d, 1H, J 6.5 Hz).

ESI-MS m/z calculated [M+H]$^+$: 410.0; found: 410.0.

Method H

An appropriate aromatic o-halocarboxylic acid is suspended in tert-butanol or another suitable solvent with approximately 1.5 equivalents of an appropriate β-diketone. To this mixture is added approximately 0.25 equivalents of copper, copper (I) bromide or copper (I) iodide. The suspension is then treated with approximately 1.6 equivalents of potassium tert-butoxide or sodium ethoxide, sealed in a pressure-resistant vessel and heated in a microwave reactor with stirring at around 180° C. for approximately 1 hour. Alternatively, a solvent with a sufficiently high boiling point (such as N,N-dimethylacetamide) may be used and the mixture is heated at reflux in an open vessel until the substrate has been substantially converted. The resulting mixture is diluted with water, neutralised with aqueous NH$_4$Cl and extracted with a suitable organic solvent. The organic extracts are dried and concentrated and the residue may be purified by flash chromatography. The lactone intermediate is then hydrolysed by treatment with dilute aqueous hydroxide solution using acetonitrile as a co-solvent.

3-[2-(4-Chlorophenyl)-2-oxoethyl]-isonicotinic acid

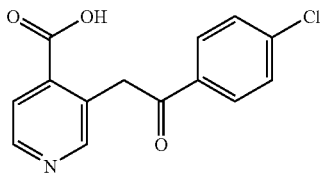 [SMILES: O=C(Cc1cnccc1C(=O)O)c1ccc(Cl)cc1]

3-[2-(4-Chlorophenyl)-2-oxoethyl]-isonicotinic acid (above) was prepared by Method H using 3-chloro-isonicotinic acid and 1,3-bis-(4-chlorophenyl)-propane-1,3-dione.

$^1$H NMR (300 MHz, d6-DMSO) δ 4.74 (s, 2H), 7.62 (d, 2H, J 8.7 Hz), 7.72 (d, 1H, J 5.0 Hz), 8.06 (d, 2H, J 8.7 Hz), 8.51 (s, 1H), 8.57 (d, 1H, J 5.0 Hz).

ESI-MS m/z calculated [M+H]$^+$: 276.0; found: 276.1

Method I

An appropriate aromatic carboxylic acid derivative is treated with aluminium chloride (1-3 equivalents) and an excess of a suitable aromatic nucleophile. The mixture is cooled or heated (typically 0-90° C.) if necessary and allowed to react until the carboxylic acid derivative is substantially consumed. The reaction mixture is poured into ice and dilute HCl. If a solid precipitates, it may be filtered off and washed. If no solid precipitates, the mixture is extracted into ethyl acetate or dichloromethane, dried with MgSO$_4$ and concentrated. The product may be further purified by recrystallisation from a suitable solvent or by chromatography. In some cases the product cyclises to form a lactone, which may be hydrolysed by treatment with dilute aqueous hydroxide solution using acetonitrile as a co-solvent.

2-[2-(4-Chlorophenyl)-2-oxoethyl]-benzoic acid

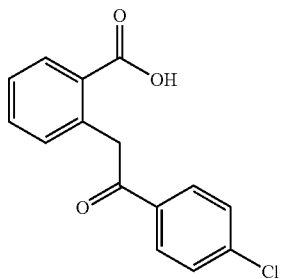 [SMILES: O=C(Cc1ccccc1C(=O)O)c1ccc(Cl)cc1]

2-[2-(4-Chlorophenyl)-2-oxoethyl]-benzoic acid (above) was prepared by method I using homophthalic anhydride and chlorobenzene. In this case, it was found to be advantageous to heat the reaction to 85° C. for 4 hours. The product was isolated by flash chromatography.

$^1$H NMR (300 MHz, CDCl$_3$) 4.66 (s, 2H), 7.26 (d, 1H, J 7.1 Hz), 7.41 (dd, 1H, J 7.6 Hz, J 7.6 Hz), 7.45 (d, 2H, J 8.5 Hz), 7.55 (dd, 1H, J 7.4 Hz, J 7.5 Hz), 7.96 (d, 2H, J 8.5 Hz), 8.12 (d, 2H, J 7.8 Hz)

Method J

A mixture of an appropriate 2-methyl aromatic carboxylic acid in THF is treated with approximately 2 to 4 equivalents of lithium diisopropylamide at a temperature between −78° C. and 0° C. The mixture is stirred for around 1 hour while the temperature is increased to 0° C. The mixture is then cooled to −78° C. and a solution of approximately 1.2 equivalents of an appropriate ester, amide, Weinreb amide or suitable alternative electrophile is then added. The reaction is allowed to warm to 0° C. with stirring for 2 to 4 hours and then allowed to warm to room temperature before being poured into dilute aqueous HCl. The crude product is collected by filtration and purified by recrystallisation or flash chromatography. If no precipitate forms the solution is extracted with a suitable organic solvent and the organic extracts are dried and concentrated. The residue may be purified by recrystallisation or flash chromatography.

The method is an adaptation of procedures described in Guion, T. S., et al., 1996, Synth. Communications, 26:1753-1762 and Epsztajn, J., et al., 1992, Synth. Communications, 22:1239-1247.

2-[2-(4-Chlorophenyl)-2-oxoethyl]-3-fluorobenzoic acid

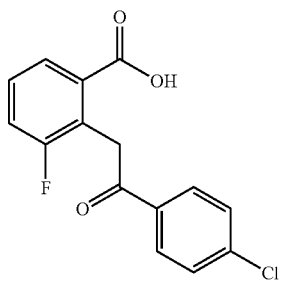 [SMILES: O=C(Cc1c(F)cccc1C(=O)O)c1ccc(Cl)cc1]

The keto-acid above was prepared by Method J using 3-fluoro-2-methylbenzoic acid and methyl 4-chlorobenzoate.

$^1$H NMR (300 MHz, d6-acetone) δ 4.76 (s, 2H), 7.33 (m, 1H), 7.43 (m, 1H), 7.47 (d, 2H, J 8.5 Hz), 7.93 (d, 1H, J 7.7 Hz), 7.98 (d, 2H, J 8.5 Hz).

Method K

A compound of formula II (where X=O and D is —[CH$_2$]$_n$—) and a catalytic amount of 18-crown-6 are suspended in THF and cooled to −78° C. The selected alkyl halide or dihalide (approximately 3 equivalents) and then potassium t-butoxide are added. The mixture is stirred and allowed to warm to room temperature. When the reaction is complete, the mixture is cooled again and quenched with a saturated solution of ammonium chloride and diluted with a small amount of water. The organic layer is separated and washed with brine, dried over MgSO$_4$ and concentrated. The residue may be purified by recrystallisation or flash chromatography.

This method is an adaptation of procedures described in J. Org. Chem. 1991, 56:7188-7190.

2-[2-(4-Chlorophenyl)-1,1-dimethyl-2-oxo-ethyl]-benzoic acid methyl ester

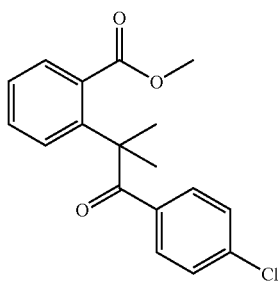 [SMILES: COC(=O)c1ccccc1C(C)(C)C(=O)c1ccc(Cl)cc1]

The keto-ester above was prepared according to Method K from 2-[2-(4-chlorophenyl)-2-oxoethyl]-benzoic acid and 3.1 equivalents of methyl iodide.

ESI-MS m/z calculated [M+H]$^+$: 317.0; found: 317.0

Method L

An appropriate 2-formyl substituted aromatic carboxylic acid and an appropriate α-methylene ketone are dissolved or suspended in ethanol. The mixture is cooled to 0° C. and the temperature is maintained below 5° C. while an aqueous solution containing approximately 1.2 equivalents of 1 M sodium hydroxide is added dropwise. The stirred solution is allowed to warm to ambient temperature. The solution is acidified with H$_2$SO$_4$, heated to 60° C. for 30 minutes and then filtered. The keto-lactone thus obtained is suspended in ethanol and hydrolysed using aqueous sodium hydroxide. The crude enone solution is then treated with hydrogen in the presence of palladium on charcoal until reduction of the alkene is complete. The reaction mixture is acidified, extracted into ethyl acetate, dried (MgSO$_4$) and concentrated.

2-[3-(4-Chlorophenyl)-3-oxo-propyl]-benzoic acid

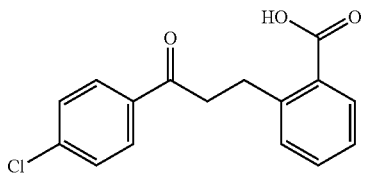 [SMILES: O=C(CCc1ccccc1C(=O)O)c1ccc(Cl)cc1]

The keto-acid above was prepared by Method L from 2-formylbenzoic acid and 1-(4-chlorophenyl)-ethanone.

$^1$H NMR (300 MHz, CDCl$_3$) 3.15-3.50 (m, 4H), 7.15-7.62 (m, 5H, overlapping CHCl$_3$), 7.74-7.83 (m, 1H), 7.87-7.98 (m, 2H)

ESI-MS m/z calculated for [M+H]$^+$: 289.0; found: 288.9

Method M

An appropriate compound of Formula I that contains an oxidisable alkylene group is dissolved or suspended in dichloromethane and treated with potassium permanganate (5 equivalents) and a catalytic amount of 18-crown-6 in dichloromethane and the mixture is stirred at ambient temperature. After allowing time to react (typically 2-48 hours), the mixture is washed with an equal volume of water approximately six times. The organic layer is then dried (MgSO$_4$) and concentrated. The residue may be purified by flash chromatography. Alternatively, the substrate is dissolved or suspended in acetic acid and treated with chromium (VI) oxide. After allowing time to react (typically 2-48 hours), the mixture is diluted with ethyl acetate and washed several times with water. The organic layer is then dried (MgSO$_4$) and concentrated. The crude product may be purified by flash chromatography.

10a'-(4'-Chlorophenyl)-1'-(4'-methoxybenzoyl)-2',3',10',10a'-tetrahydro-1'H-spiro[cyclopropane-(1,10'-imidazo[1,2-b]isoquinolin[5]one)]

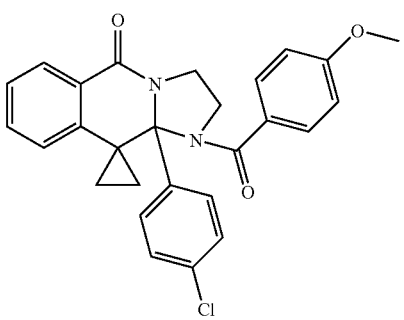 [SMILES: COc1ccc(C(=O)N2CCN3C(=O)c4ccccc4C4(CC4)C23c2ccc(Cl)cc2)cc1]

The isoquinolinone derivative above was prepared by Method M from 10a'-(4'-chlorophenyl)-1'-(4'-methoxybenzyl)-2',3',10',10a'-tetrahydro-1'H-spiro[cyclopropane-(1,10'-imidazo[1,2-b]isoquinolin[5]one)] using potassium permanganate in dichloromethane and was purified by flash chromatography.

$^1$H NMR (300 MHz, d6-acetone) δ 0.62 (ddd, 1H, J 10.1, 7.4, 4.5 Hz), 1.61 (ddd, 1H, J 10.1, 6.6, 4.5 Hz), 2.10-2.19 (m, 2H), 3.85 (s, 3H), 3.94-4.14 (m, 3H), 4.36-4.41 (m, 1H), 6.97 (d, 2H, J 8.8 Hz), 7.15 (d, 2H, J 8.8 Hz), 7.26 (td, 1H, J 7.7, 1.1 Hz), 7.36 (d, 1H, J 7.7 Hz), 7.41 (d, 2H, J 8.8 Hz), 7.53 (t, 1H, J 7.7 Hz), 7.59 (d, 2H, J 8.8 Hz), 7.77 (dd, 1H, J 7.7, 1.1 Hz).

ESI-MS m/z calculated [M+H]$^+$: 459.0; found: 459.0

10a-(4-Chlorophenyl)-10,10a-dihydro-1H-imidazo[1,2-b]isoquinoline-2,3,5-trione

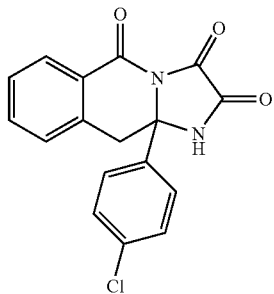 [SMILES: O=C1NC2(c3ccc(Cl)cc3)Cc3ccccc3C(=O)N2C1=O]

The isoquinolinone derivative above was prepared by method M from 10a-(4-chlorophenyl)-2,3,10,10a-tetrahydro-1H-imidazo[1,2-b]isoquinolin-5-one using chromium (VI) oxide in acetic acid.

$^1$H NMR (300 MHz, d6-acetone) δ 4.04 (d, 1H, J 15.7 Hz), 4.31 (d, 1H, J 15.7 Hz), 7.37 (d, 2H, J 8.9 Hz) 7.39-7.44 (m, 1H), 7.48-7.53 (m, 1H), 7.51 (d, 2H, J 8.8 Hz), 7.60 (ddd, 1H, J 7.5 Hz, 7.4 Hz, 1.1 Hz), 7.98 (dd, 1H, J 7.8, 1.1 Hz).

ESI-MS m/z calculated [M+H]$^+$: 327.0; found: 326.9

Method N

A selected carbonyl compound is dissolved in toluene or suitable inert solvent and treated with Lawesson's reagent (approximately 1.1 equivalents). The mixture is heated to reflux for 24-72 h. The cooled mixture is then washed several times with water and the organic phase is dried (MgSO$_4$) and concentrated. The residue may be purified by flash chromatography.

10a-(4-Chlorophenyl)-2,3,10,10a-tetrahydro-1H-imidazo[1,2-b]isoquinoline-5-thione

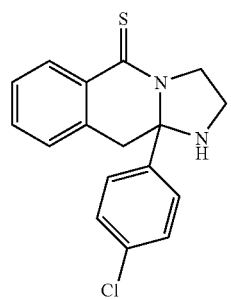

The above thioamide was prepared by Method N from 10a-(4-chlorophenyl)-2,3,10,10a-tetrahydro-1H-imidazo[1,2-b]isoquinolin-5-one $^1$H NMR (300 MHz, d6-acetone) δ 2.68-2.75 (m, 1H), 3.38-3.42 (m, 1H), 3.55 (br s, 2H), 3.71 (br s, 1H), 3.87 (dd, 1H, J 13.5, 7.7 Hz), 4.05 (ddd, 1H, J 13.5, 9.7, 8.3 Hz), 7.04 (d, 1H, J 7.1 Hz), 7.22-7.33 (m, 6H), 8.42 (d, 1H, J 7.5 Hz).

ESI-MS m/z calculated [M+H]$^+$: 315.0; found: 315.0

Method O

Selected compounds of the invention may be separated into single stereoisomers by HPLC using chromatographic columns with a chiral stationary phase. For example, the following racemic compounds were separated into enantiomers under the conditions detailed below.

Column: Chiralcel OD-H Column 250×4.6 mm
Detector wavelength: 254 nm
Separation of Compound 1-019
Mobile Phase A: Ethanol
Flow Rate: 0.7 mL/min
Isocratic Elution: 100% Mobile Phase A
Run Time: 30 mins
Column Temperature: 30° C.
Injection Volume: 20 µl
Separation of Compounds 1-008, 1-036 & 1-043
Mobile Phase A: Hexane
Mobile Phase B: Ethanol
Flow Rate: 0.7 mL/min
Run Time: 42 mins
Post Run time: 5 mins
Column Temperature: 30° C.
Injection Volume: 20 µl
Gradient Timetable:

| Time (min) | % Mobile Phase B |
|---|---|
| 0 | 2 |
| 30 | 98 |
| 40 | 98 |
| 42 | 2 |

Separation of Compounds 1-006, 1-005, 1-029, 1-031, 1-032, 2-02 & 2-06
Mobile Phase A: Hexane
Mobile Phase B: Ethanol
Flow Rate: 0.7 mL/min
Isocratic Elution: 70% Mobile Phase A, 30% Mobile Phase B
Run Time: 33 mins
Column Temperature: 30° C.
Injection Volume: 20 µl

TABLE 1

Separation of Enantiomers Using Chiralcel OD-H Column (elution conditions described above)

| Compound Number | Retention Time of Enantiomer A (min) | Retention Time of Enantiomer B (min) |
|---|---|---|
| 1-019 | 9.3 | 12.66 |
| 1-008 | 30.4 | 34.5 |
| 1-006 | 15.7 | 18.0 |
| 1-005 | 13.4 | 17.9 |
| 2-02 | 8.2 | 13.4 |
| 1-029 | 13.0 | 19.7 |
| 1-031 | 20.6 | 23.9 |
| 1-032 | 13.2 | 15.4 |
| 1-036 | 24.9 | 28.0 |
| 1-043 | 22.6 | 25.3 |
| 2-06 | 7.1 | 10.3 |

It will be understood that compounds of Formula I that are obtained by the above processes may, where appropriate, be elaborated into additional compounds of Formula I using techniques known in the art.

The above described methods were used to make the compounds in Table 2 and Table 3 below. All compounds shown have been prepared. The compounds have been characterised by mass spectrometry and the observed molecular ion for each is indicated in the tables.

TABLE 2
Prepared compounds of formula I
| Compound no. | Structure | Observed m/z ([M + H]+) | Synthesis method(s) |
|---|---|---|---|
| 1-001 | 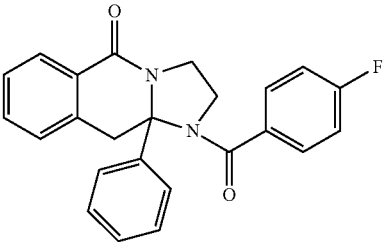 [SMILES: O=C(c1ccc(F)cc1)N1CCN2C(=O)c3ccccc3CC12c1ccccc1] | 387.0 | H, A, F |
| 1-002 | 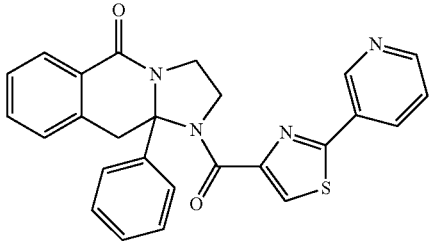 [SMILES: O=C(c1csc(-c2cccnc2)n1)N1CCN2C(=O)c3ccccc3CC12c1ccccc1] | 453.1 | H, A, F |
| 1-003 | 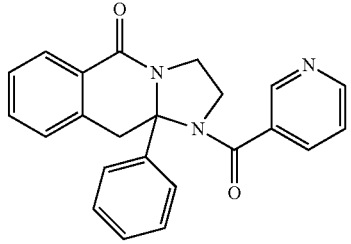 [SMILES: O=C(c1cccnc1)N1CCN2C(=O)c3ccccc3CC12c1ccccc1] | 370.1 | H, A, F |
| 1-004 | 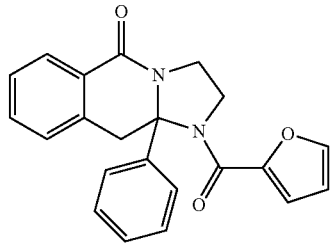 [SMILES: O=C(c1ccco1)N1CCN2C(=O)c3ccccc3CC12c1ccccc1] | 359.1 | H, A, F |
| 1-005 | 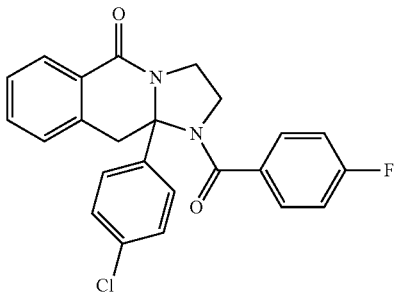 | 421.1 | I, A, F |

TABLE 2-continued

Prepared compounds of formula I

| Compound no. | Structure | Observed m/z ([M + H]+) | Synthesis method(s) |
|---|---|---|---|
| 1-006 | 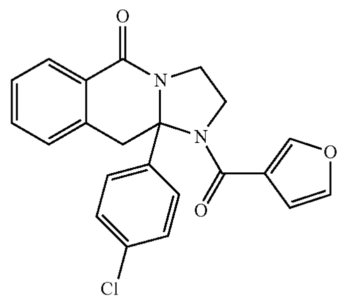 [SMILES: O=C(c1ccoc1)N1CCN2C(=O)c3ccccc3CC12c1ccc(Cl)cc1] | 393.1 | I, A, F |
| 1-007 | 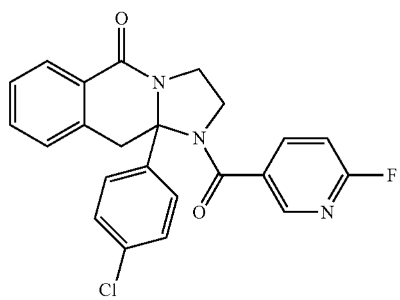 [SMILES: O=C(c1ccc(F)nc1)N1CCN2C(=O)c3ccccc3CC12c1ccc(Cl)cc1] | 422.1 | I, A, F |
| 1-008 | 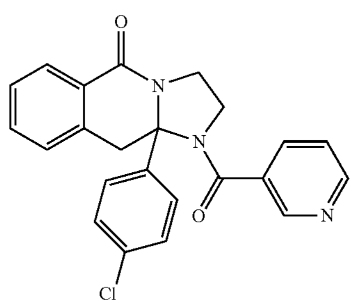 [SMILES: O=C(c1cccnc1)N1CCN2C(=O)c3ccccc3CC12c1ccc(Cl)cc1] | 404.1 | I, A, F |
| 1-009 | 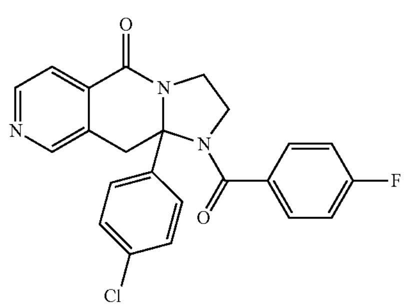 [SMILES: O=C(c1ccc(F)cc1)N1CCN2C(=O)c3ccncc3CC12c1ccc(Cl)cc1] | 422.1 | H, A, F |
| 1-010 | 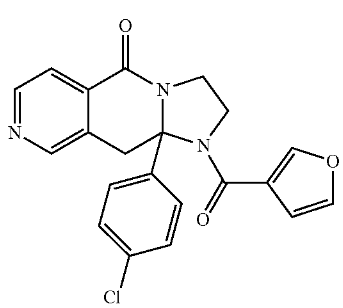 [SMILES: O=C(c1ccoc1)N1CCN2C(=O)c3ccncc3CC12c1ccc(Cl)cc1] | 394.1 | H, A, F |

TABLE 2-continued

Prepared compounds of formula I

| Compound no. | Structure | Observed m/z ([M + H]+) | Synthesis method(s) |
|---|---|---|---|
| 1-011 | 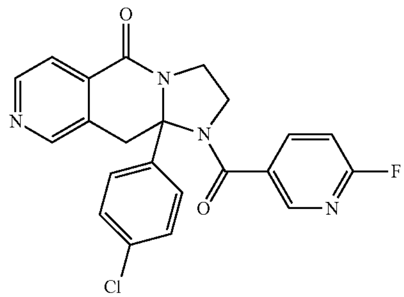 [SMILES: O=C(c1ccc(F)nc1)N1CCN2C(=O)c3ccncc3CC12c1ccc(Cl)cc1] | 423.1 | H, A, F |
| 1-012 | 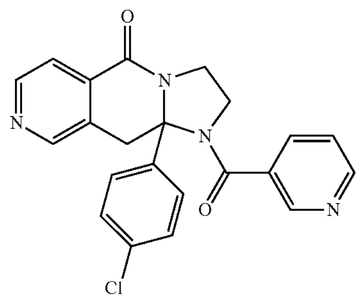 [SMILES: O=C(c1cccnc1)N1CCN2C(=O)c3ccncc3CC12c1ccc(Cl)cc1] | 405.2 | H, A, F |
| 1-013 | 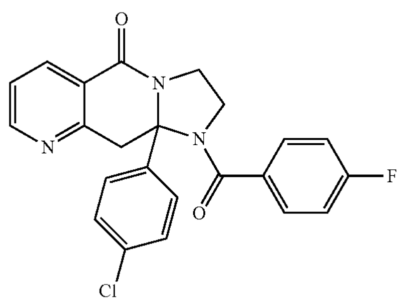 [SMILES: O=C(c1ccc(F)cc1)N1CCN2C(=O)c3cccnc3CC12c1ccc(Cl)cc1] | 422.1 | H, A, F |
| 1-014 | 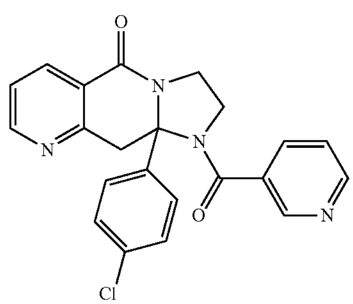 [SMILES: O=C(c1cccnc1)N1CCN2C(=O)c3cccnc3CC12c1ccc(Cl)cc1] | 405.2 | H, A, F |
| 1-015 | 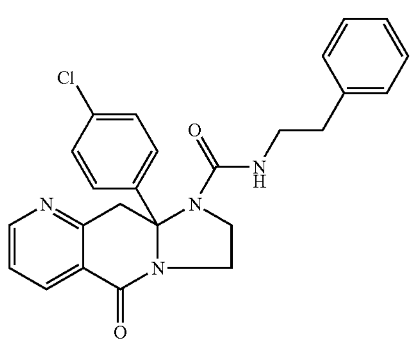 [SMILES: O=C(NCCc1ccccc1)N1CCN2C(=O)c3cccnc3CC12c1ccc(Cl)cc1] | 447.1 | H, A, F |

TABLE 2-continued
Prepared compounds of formula I
| Compound no. | Structure | Observed m/z ([M + H]+) | Synthesis method(s) |
|---|---|---|---|
| 1-016 | 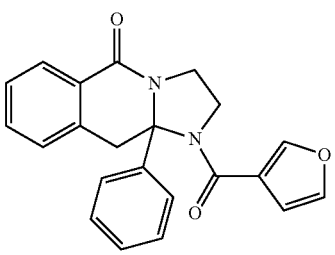 [SMILES: O=C(c1ccoc1)N1CCN2C(=O)c3ccccc3CC12c1ccccc1] | 359.1 | I, A, F |
| 1-017 | 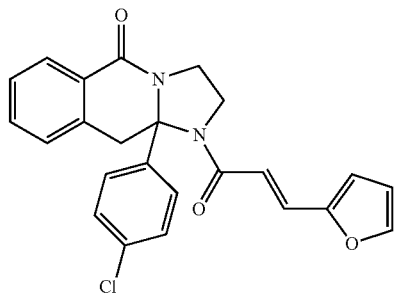 [SMILES: O=C(/C=C/c1ccco1)N1CCN2C(=O)c3ccccc3CC12c1ccc(Cl)cc1] | 419.0 | I, A, F |
| 1-018 | 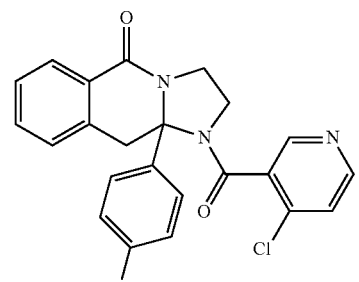 | 438.0 | I, A, F |
| 1-019 | 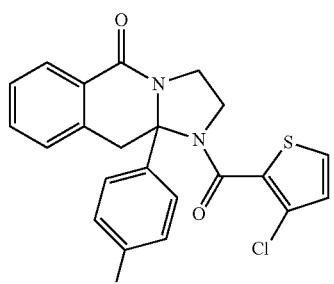 | 443.0 | I, A, F |
| 1-020 | 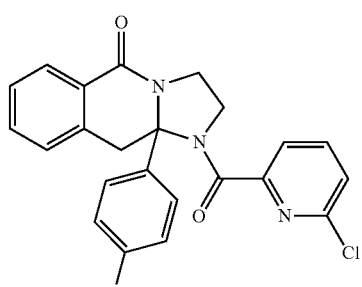 | 438.0 | I, A, F |

TABLE 2-continued

Prepared compounds of formula I

| Compound no. | Structure | Observed m/z ([M + H]+) | Synthesis method(s) |
|---|---|---|---|
| 1-021 | 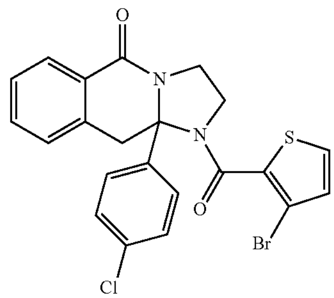 [SMILES: O=C1c2ccccc2CC2(c3ccc(Cl)cc3)N1CCN2C(=O)c1sccc1Br] | 487.0 | I, A, F |
| 1-022 | 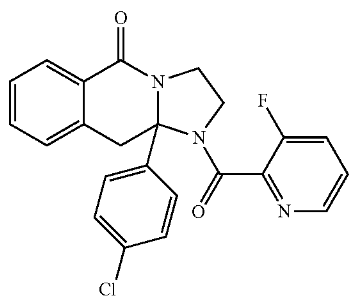 [SMILES: O=C1c2ccccc2CC2(c3ccc(Cl)cc3)N1CCN2C(=O)c1ncccc1F] | 422.0 | I, A, F |
| 1-023 | 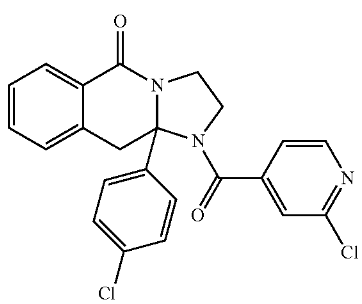 [SMILES: O=C(c1ccnc(Cl)c1)N1CCN2C(=O)c3ccccc3CC12c1ccc(Cl)cc1] | 438.0 | I, A, F |
| 1-024 | 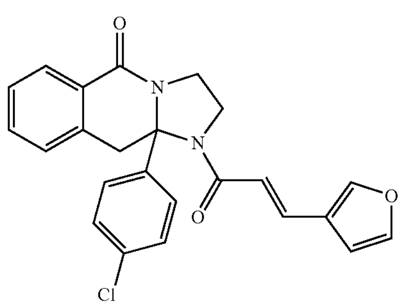 [SMILES: O=C(/C=C/c1ccoc1)N1CCN2C(=O)c3ccccc3CC12c1ccc(Cl)cc1] | 419.0 | I, A, F |
| 1-025 | 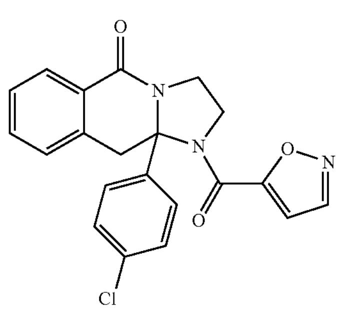 [SMILES: O=C(c1ccno1)N1CCN2C(=O)c3ccccc3CC12c1ccc(Cl)cc1] | 394.1 | I, A, F |

TABLE 2-continued

Prepared compounds of formula I

| Compound no. | Structure | Observed m/z ([M + H]+) | Synthesis method(s) |
|---|---|---|---|
| 1-026 | 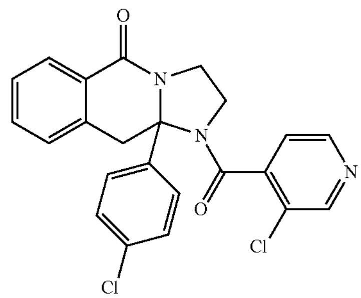 [SMILES: O=C(c1ccncc1Cl)N1CCN2C(=O)c3ccccc3CC12c1ccc(Cl)cc1] | 438.0 | I, A, F |
| 1-027 | 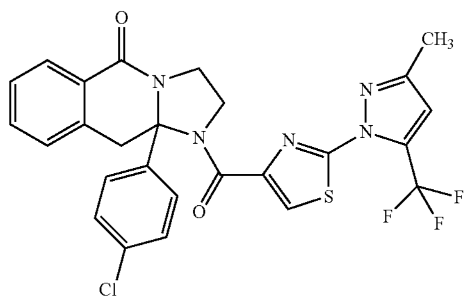 [SMILES: Cc1cc(C(F)(F)F)n(-c2nc(C(=O)N3CCN4C(=O)c5ccccc5CC34c3ccc(Cl)cc3)cs2)n1] | 558.0 | I, A, F |
| 1-028 | 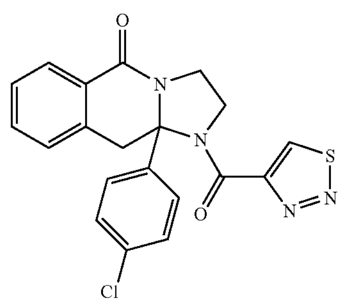 [SMILES: O=C(c1csnn1)N1CCN2C(=O)c3ccccc3CC12c1ccc(Cl)cc1] | 411.0 | I, A, F |
| 1-029 | 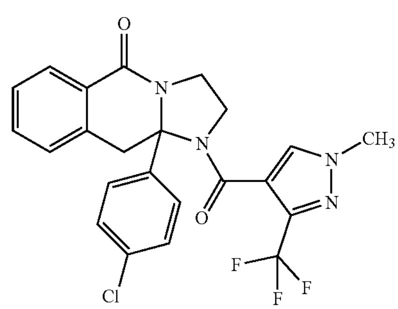 [SMILES: Cn1cc(C(=O)N2CCN3C(=O)c4ccccc4CC32c2ccc(Cl)cc2)c(C(F)(F)F)n1] | 475.0 | I, A, F |
| 1-030 | 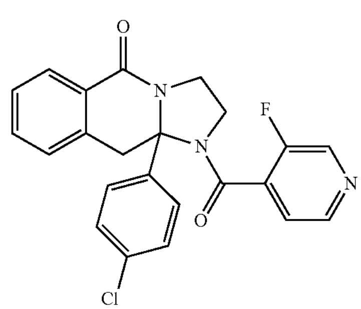 [SMILES: O=C(c1ccncc1F)N1CCN2C(=O)c3ccccc3CC12c1ccc(Cl)cc1] | 422.0 | I, A, F |

TABLE 2-continued
Prepared compounds of formula I
| Compound no. | Structure | Observed m/z ([M + H]+) | Synthesis method(s) |
|---|---|---|---|
| 1-031 | 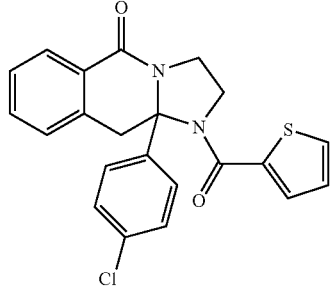 [SMILES: O=C(c1cccs1)N1CCN2C(=O)c3ccccc3CC12c1ccc(Cl)cc1] | 409.0 | I, A, F |
| 1-032 | 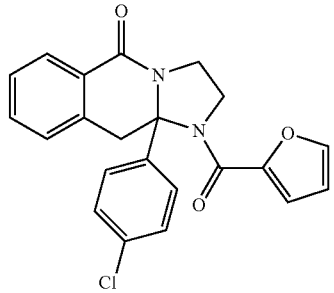 [SMILES: O=C(c1ccco1)N1CCN2C(=O)c3ccccc3CC12c1ccc(Cl)cc1] | 393.0 | I, A, F |
| 1-033 | 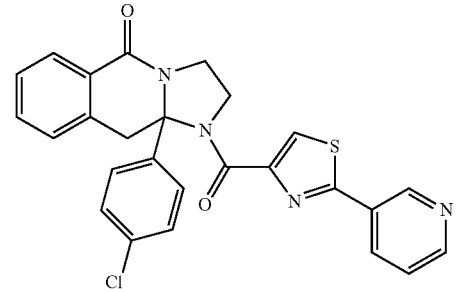 [SMILES: O=C(c1csc(-c2cccnc2)n1)N1CCN2C(=O)c3ccccc3CC12c1ccc(Cl)cc1] | 487.0 | I, A, F |
| 1-034 | 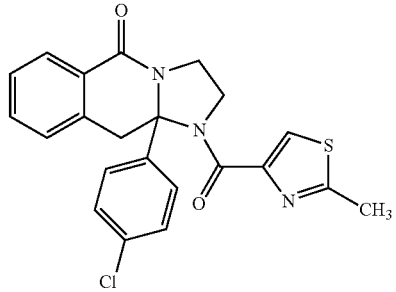 [SMILES: Cc1nc(C(=O)N2CCN3C(=O)c4ccccc4CC23c2ccc(Cl)cc2)cs1] | 424.0 | I, A, F |
| 1-035 | 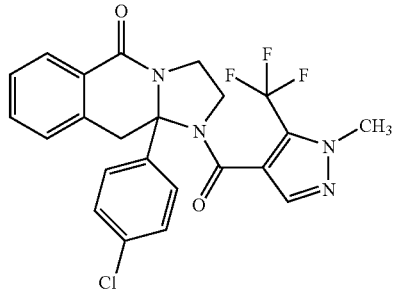 [SMILES: Cn1ncc(C(=O)N2CCN3C(=O)c4ccccc4CC32c2ccc(Cl)cc2)c1C(F)(F)F] | 475.0 | I, A, F |

TABLE 2-continued

Prepared compounds of formula I

| Compound no. | Structure | Observed m/z ([M + H]+) | Synthesis method(s) |
|---|---|---|---|
| 1-036 | 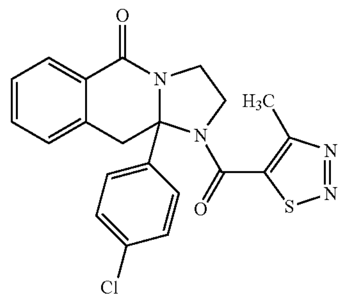 [SMILES: Cc1nnsc1C(=O)N1CCN2C(=O)c3ccccc3CC21c1ccc(Cl)cc1] | 424.9 | I, A, F |
| 1-037 | 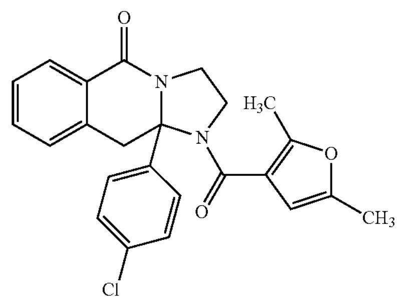 [SMILES: Cc1cc(C(=O)N2CCN3C(=O)c4ccccc4CC32c2ccc(Cl)cc2)c(C)o1] | 421.0 | I, A, F |
| 1-038 | 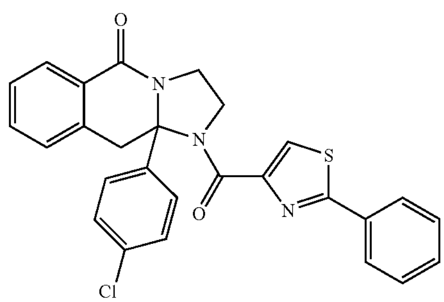 [SMILES: O=C(c1csc(-c2ccccc2)n1)N1CCN2C(=O)c3ccccc3CC12c1ccc(Cl)cc1] | 486.0 | I, A, F |
| 1-039 | 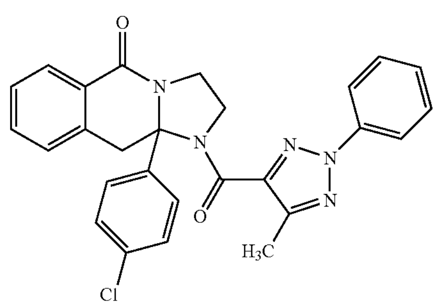 [SMILES: Cc1nn(-c2ccccc2)nc1C(=O)N1CCN2C(=O)c3ccccc3CC21c1ccc(Cl)cc1] | 484.0 | I, A, F |
| 1-040 | 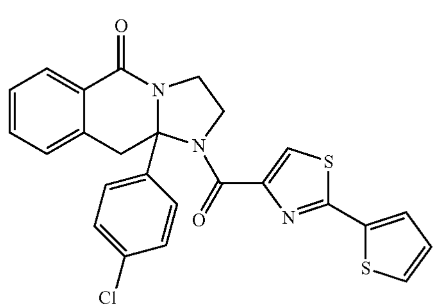 [SMILES: O=C(c1csc(-c2cccs2)n1)N1CCN2C(=O)c3ccccc3CC12c1ccc(Cl)cc1] | 492.0 | I, A, F |

TABLE 2-continued

Prepared compounds of formula I

| Compound no. | Structure | Observed m/z ([M + H]+) | Synthesis method(s) |
|---|---|---|---|
| 1-041 | 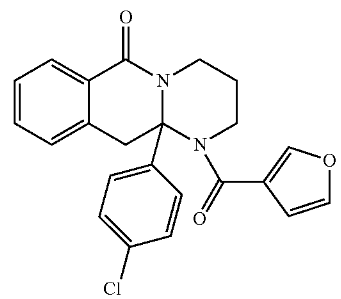 [SMILES: O=C(c1ccoc1)N1CCCN2C(=O)c3ccccc3CC12c1ccc(Cl)cc1] | 407.1 | I, A, F |
| 1-042 | 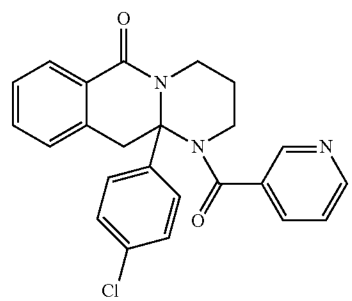 [SMILES: O=C(c1cccnc1)N1CCCN2C(=O)c3ccccc3CC12c1ccc(Cl)cc1] | 418.1 | I, A, F |
| 1-043 | 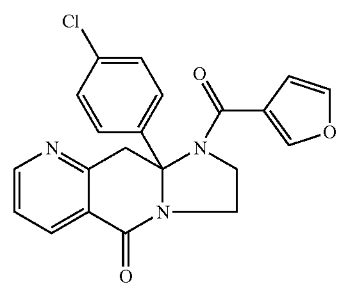 [SMILES: O=C(c1ccoc1)N1CCN2C(=O)c3cccnc3CC12c1ccc(Cl)cc1] | 394.1 | H, A, F |
| 1-044 | 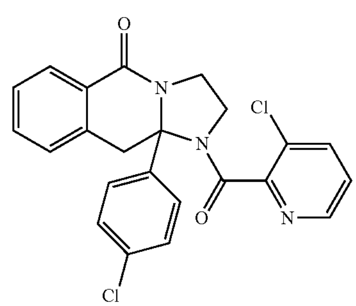 | 438.0 | I, A, F |
| 1-045 | 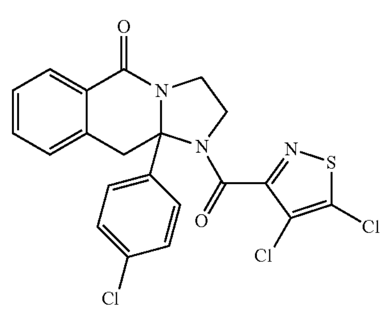 [SMILES: O=C1c2ccccc2CC2(c3ccc(Cl)cc3)N1CCN2C(=O)c1nsc(Cl)c1Cl] | 477.9 | I, A, F |

TABLE 2-continued

Prepared compounds of formula I

| Compound no. | Structure | Observed m/z ([M + H]+) | Synthesis method(s) |
|---|---|---|---|
| 1-046 | 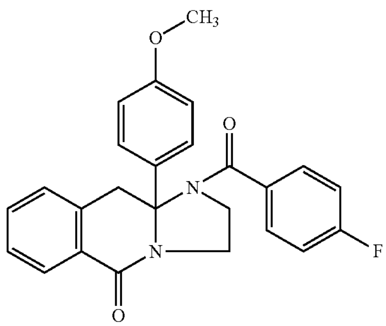 [SMILES: COc1ccc(C23Cc4ccccc4C(=O)N2CCN3C(=O)c2ccc(F)cc2)cc1] | 417.1 | I, A, F |
| 1-047 | 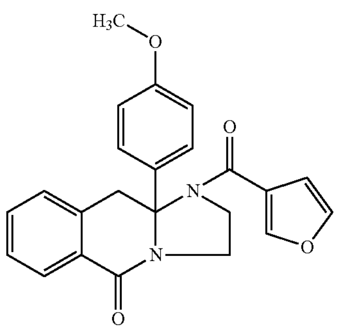 [SMILES: COc1ccc(C23Cc4ccccc4C(=O)N2CCN3C(=O)c2ccoc2)cc1] | 389.0 | I, A, F |
| 1-048 | 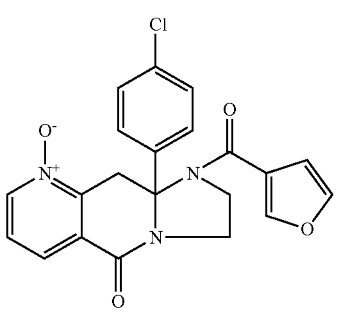 [SMILES: O=C(c1ccoc1)N1CCN2C(=O)c3ccc[n+]([O-])c3CC12c1ccc(Cl)cc1] | 410.0 | H, A, F, G |
| 1-049 | 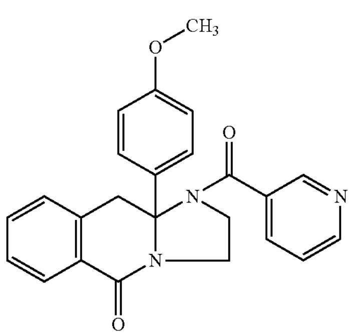 [SMILES: COc1ccc(C23Cc4ccccc4C(=O)N2CCN3C(=O)c2cccnc2)cc1] | 400.2 | I, A, F |

TABLE 2-continued
Prepared compounds of formula I
| Compound no. | Structure | Observed m/z ([M + H]+) | Synthesis method(s) |
|---|---|---|---|
| 1-050 | 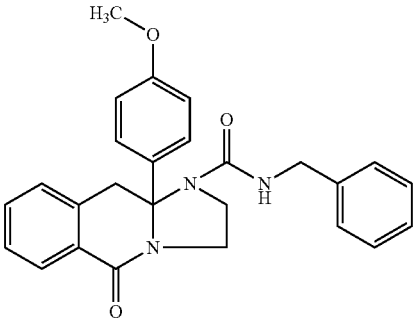 [SMILES: COc1ccc(C23Cc4ccccc4C(=O)N2CCN3C(=O)NCc2ccccc2)cc1] | 428.0 | I, A, F |
| 1-051 | 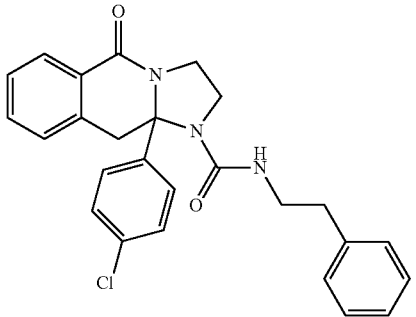 [SMILES: O=C(NCCc1ccccc1)N1CCN2C(=O)c3ccccc3CC12c1ccc(Cl)cc1] | 446.0 | I, A, F |
| 1-052 | 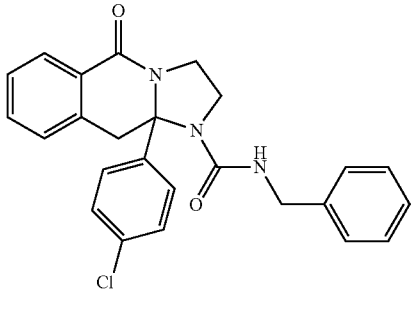 [SMILES: O=C(NCc1ccccc1)N1CCN2C(=O)c3ccccc3CC12c1ccc(Cl)cc1] | 432.0 | I, A, F |
| 1-053 | 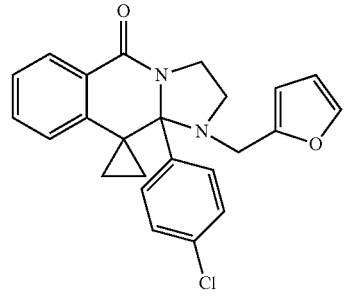 [SMILES: O=C1c2ccccc2C2(CC2)C2(c3ccc(Cl)cc3)N(Cc3ccco3)CCN12] | 405.1 | I, K, D |

TABLE 2-continued
Prepared compounds of formula I
| Compound no. | Structure | Observed m/z ([M + H]+) | Synthesis method(s) |
|---|---|---|---|
| 1-054 | 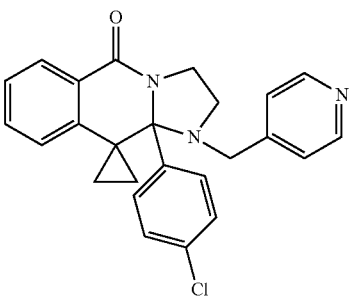 [SMILES: O=C1c2ccccc2C2(CC2)C2(c3ccc(Cl)cc3)N(Cc3ccncc3)CCN12] | 416.1 | I, K, D |
| 1-055 | 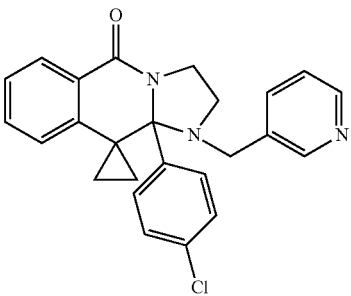 [SMILES: O=C1c2ccccc2C2(CC2)C2(c3ccc(Cl)cc3)N(Cc3cccnc3)CCN12] | 416.1 | I, K, D |
| 1-056 | 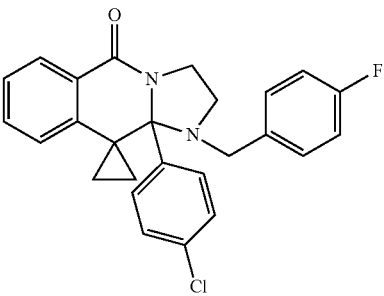 [SMILES: O=C1c2ccccc2C2(CC2)C2(c3ccc(Cl)cc3)N(Cc3ccc(F)cc3)CCN12] | 433.1 | I, K, D |
| 1-057 | 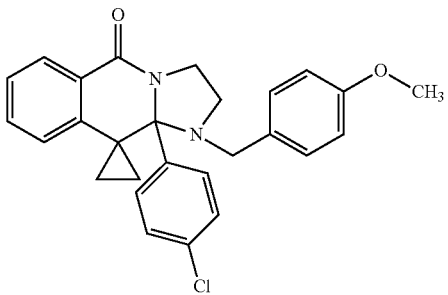 [SMILES: COc1ccc(CN2CCN3C(=O)c4ccccc4C4(CC4)C23c2ccc(Cl)cc2)cc1] | 445.0 | I, K, D |
| 1-058 | 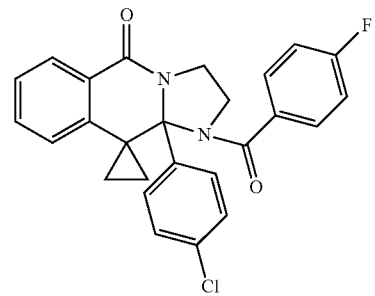 [SMILES: O=C(c1ccc(F)cc1)N1CCN2C(=O)c3ccccc3C3(CC3)C12c1ccc(Cl)cc1] | 447.0 | I, K, D, M |

TABLE 2-continued
Prepared compounds of formula I
| Compound no. | Structure | Observed m/z ([M + H]+) | Synthesis method(s) |
|---|---|---|---|
| 1-059 | 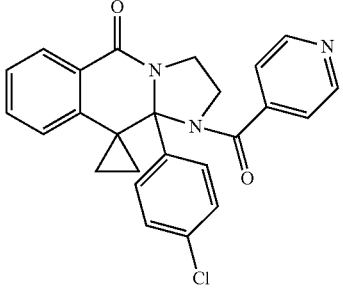 [SMILES: O=C(c1ccncc1)N1CCN2C(=O)c3ccccc3C3(CC3)C12c1ccc(Cl)cc1] | 430.0 | I, K, D, M |
| 1-060 | 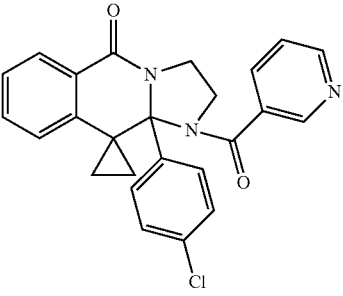 [SMILES: O=C(c1cccnc1)N1CCN2C(=O)c3ccccc3C3(CC3)C12c1ccc(Cl)cc1] | 430.0 | I, K, D, M |
| 1-061 | 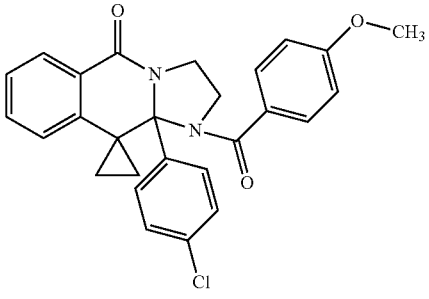 [SMILES: COc1ccc(C(=O)N2CCN3C(=O)c4ccccc4C4(CC4)C23c2ccc(Cl)cc2)cc1] | 459.0 | I, K, D, M |
| 1-062 | 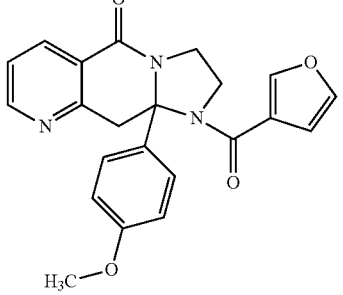 | 390.0 | J, A, F |
| 1-063 | 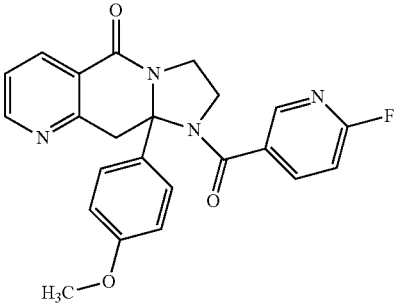 [SMILES: COc1ccc(C23Cc4ncccc4C(=O)N2CCN3C(=O)c2ccc(F)nc2)cc1] | 419.0 | J, A, F |

TABLE 2-continued
Prepared compounds of formula I
| Compound no. | Structure | Observed m/z ([M + H]⁺) | Synthesis method(s) |
|---|---|---|---|
| 1-064 | 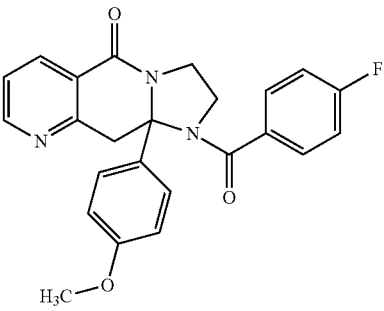 [SMILES: COc1ccc(C23Cc4ncccc4C(=O)N2CCN3C(=O)c2ccc(F)cc2)cc1] | 418.0 | J, A, F |
| 1-065 | 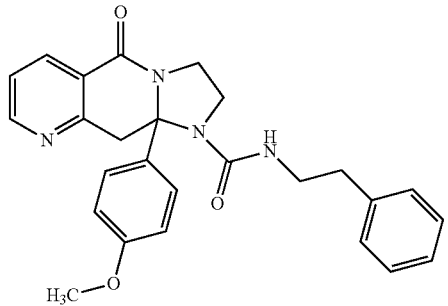 [SMILES: COc1ccc(C23Cc4ncccc4C(=O)N2CCN3C(=O)NCCc2ccccc2)cc1] | 443.0 | J, A, F |
| 1-066 | 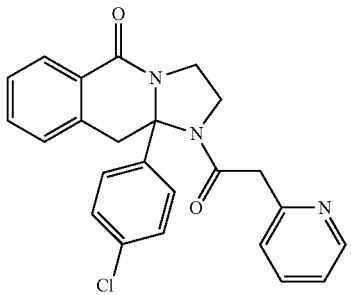 [SMILES: O=C(Cc1ccccn1)N1CCN2C(=O)c3ccccc3CC12c1ccc(Cl)cc1] | 418.0 | I, A, F |
| 1-067 | 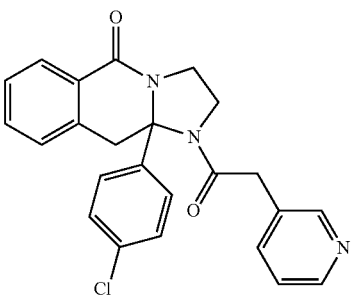 [SMILES: O=C(Cc1cccnc1)N1CCN2C(=O)c3ccccc3CC12c1ccc(Cl)cc1] | 418.1 | I, A, F |

TABLE 2-continued

Prepared compounds of formula I

| Compound no. | Structure | Observed m/z ([M + H]+) | Synthesis method(s) |
|---|---|---|---|
| 1-068 | 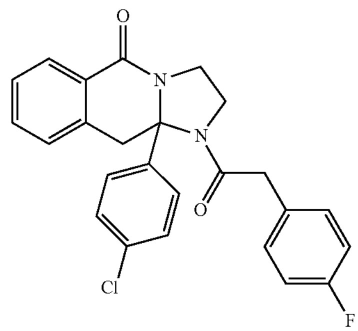 [SMILES: O=C(Cc1ccc(F)cc1)N1CCN2C(=O)c3ccccc3CC12c1ccc(Cl)cc1] | 435.1 | I, A, F |
| 1-069 | 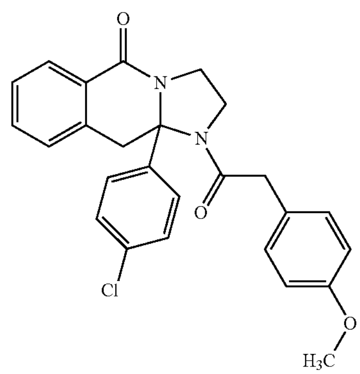 [SMILES: COc1ccc(CC(=O)N2CCN3C(=O)c4ccccc4CC23c2ccc(Cl)cc2)cc1] | 447.0 | I, A, F |
| 1-070 | 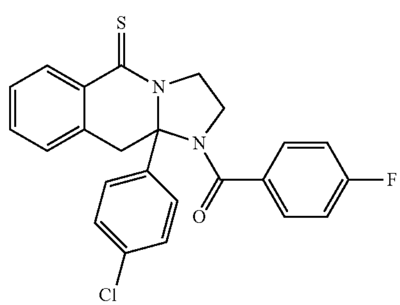 | 436.9 | I, A, N, F |
| 1-071 | 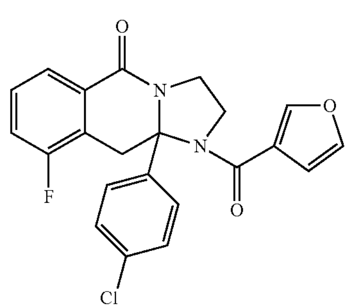 [SMILES: O=C(c1ccoc1)N1CCN2C(=O)c3cccc(F)c3CC12c1ccc(Cl)cc1] | 411.0 | J, A, F |

TABLE 2-continued

Prepared compounds of formula I

| Compound no. | Structure | Observed m/z ([M + H]+) | Synthesis method(s) |
|---|---|---|---|
| 1-072 | 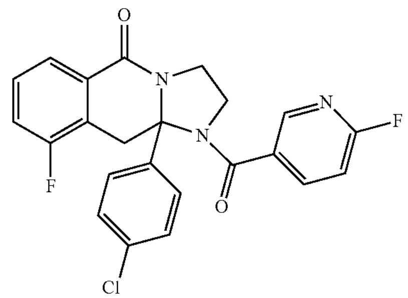 [SMILES: O=C(c1ccc(F)nc1)N1CCN2C(=O)c3cccc(F)c3CC12c1ccc(Cl)cc1] | 440.1 | J, A, F |
| 1-073 | 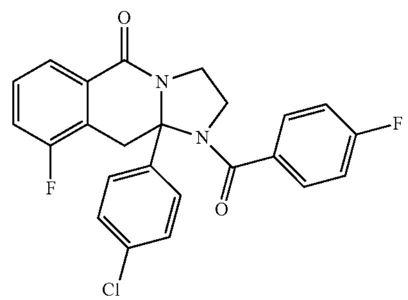 [SMILES: O=C(c1ccc(F)cc1)N1CCN2C(=O)c3cccc(F)c3CC12c1ccc(Cl)cc1] | 439.1 | J, A, F |
| 1-074 | 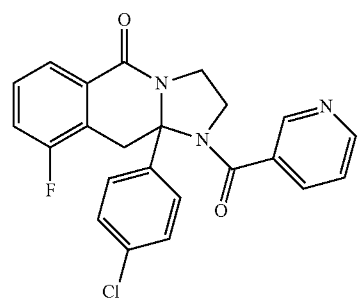 [SMILES: O=C(c1cccnc1)N1CCN2C(=O)c3cccc(F)c3CC12c1ccc(Cl)cc1] | 422.1 | J, A, F |
| 1-075 | 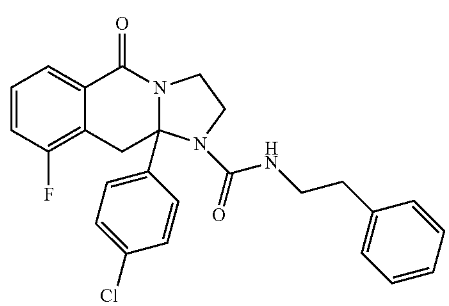 [SMILES: O=C(NCCc1ccccc1)N1CCN2C(=O)c3cccc(F)c3CC12c1ccc(Cl)cc1] | 464.0 | J, A, F |
| 1-076 | 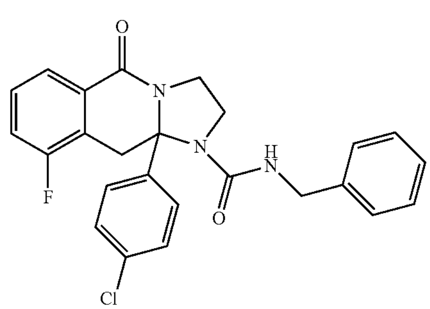 [SMILES: O=C(NCc1ccccc1)N1CCN2C(=O)c3cccc(F)c3CC12c1ccc(Cl)cc1] | 450.0 | J, A, F |

TABLE 2-continued

Prepared compounds of formula I

| Compound no. | Structure | Observed m/z ([M + H]+) | Synthesis method(s) |
|---|---|---|---|
| 1-077 | 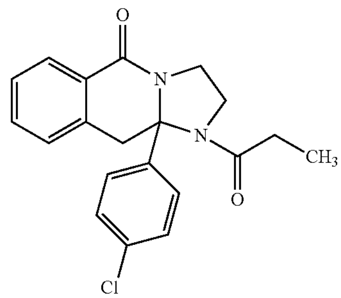 [SMILES: CCC(=O)N1CCN2C(=O)c3ccccc3CC12c1ccc(Cl)cc1] | 355.0 | I, A, F |
| 1-078 | 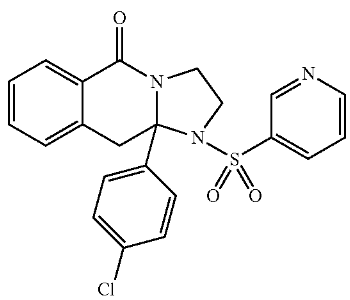 [SMILES: O=C1c2ccccc2CC2(c3ccc(Cl)cc3)N1CCN2S(=O)(=O)c1cccnc1] | 440.0 | I, A, F |
| 1-079 | 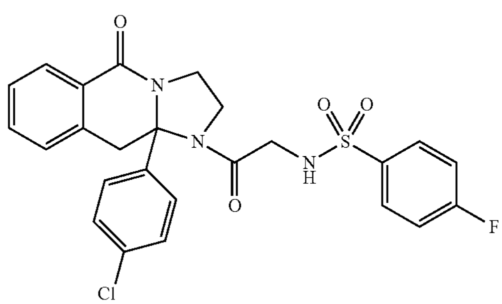 [SMILES: O=C(CNS(=O)(=O)c1ccc(F)cc1)N1CCN2C(=O)c3ccccc3CC12c1ccc(Cl)cc1] | 514.0 | I, A, B |
| 1-080 | 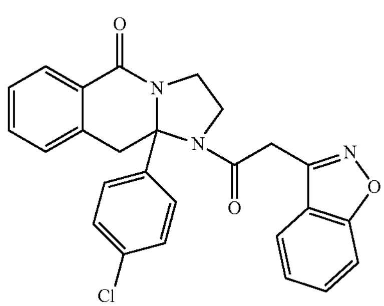 [SMILES: O=C(Cc1noc2ccccc12)N1CCN2C(=O)c3ccccc3CC12c1ccc(Cl)cc1] | 458.0 | I, A, B |
| 1-081 | 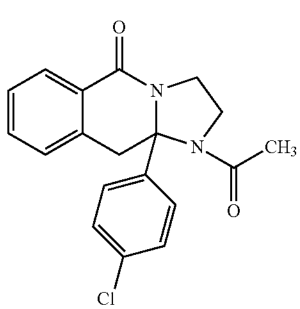 [SMILES: CC(=O)N1CCN2C(=O)c3ccccc3CC12c1ccc(Cl)cc1] | 341.0 | I, A, F |

TABLE 2-continued

Prepared compounds of formula I

| Compound no. | Structure | Observed m/z ([M + H]+) | Synthesis method(s) |
|---|---|---|---|
| 1-082 | 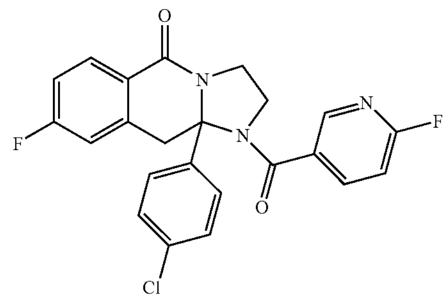 [SMILES: O=C(c1ccc(F)nc1)N1CCN2C(=O)c3ccc(F)cc3CC12c1ccc(Cl)cc1] | 440.1 | J, A, F |
| 1-083 | 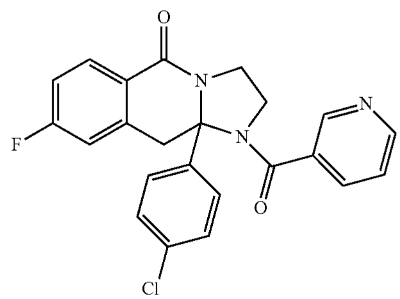 [SMILES: O=C(c1cccnc1)N1CCN2C(=O)c3ccc(F)cc3CC12c1ccc(Cl)cc1] | 422.0 | J, A, F |
| 1-084 | 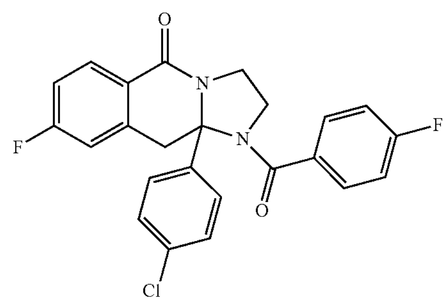 [SMILES: O=C(c1ccc(F)cc1)N1CCN2C(=O)c3ccc(F)cc3CC12c1ccc(Cl)cc1] | 439.1 | J, A, F |
| 1-085 | 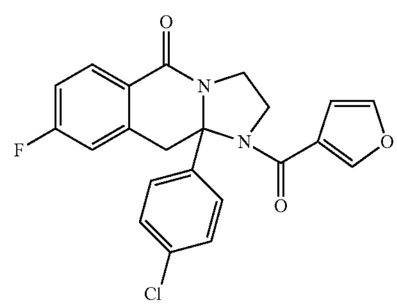 [SMILES: O=C(c1ccoc1)N1CCN2C(=O)c3ccc(F)cc3CC12c1ccc(Cl)cc1] | 411.0 | J, A, F |
| 1-086 | 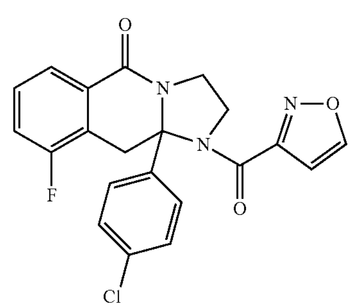 [SMILES: O=C(c1ccon1)N1CCN2C(=O)c3cccc(F)c3CC12c1ccc(Cl)cc1] | 412.0 | J, A, F |

TABLE 2-continued

Prepared compounds of formula I

| Compound no. | Structure | Observed m/z ([M + H]⁺) | Synthesis method(s) |
|---|---|---|---|
| 1-087 | 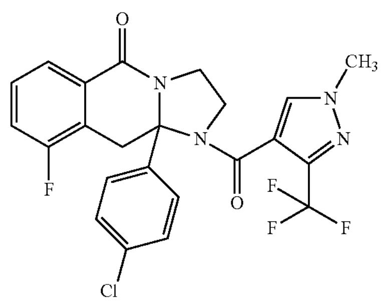 [SMILES: Cn1cc(C(=O)N2CCN3C(=O)c4cccc(F)c4CC23c2ccc(Cl)cc2)c(C(F)(F)F)n1] | 493.0 | J, A, F |
| 1-088 | 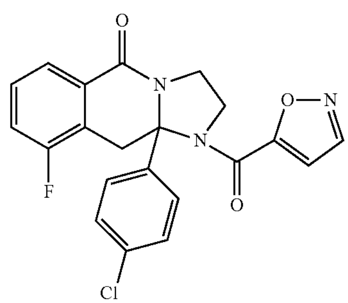 [SMILES: O=C(c1ccno1)N1CCN2C(=O)c3cccc(F)c3CC12c1ccc(Cl)cc1] | 412.0 | J, A, F |
| 1-089 | 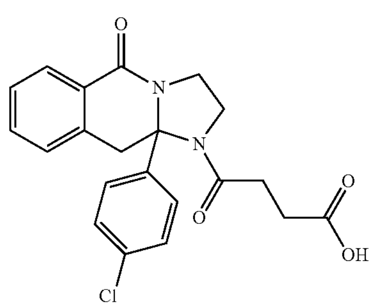 [SMILES: O=C(O)CCC(=O)N1CCN2C(=O)c3ccccc3CC12c1ccc(Cl)cc1] | 399.0 | I, A, C |
| 1-090 | 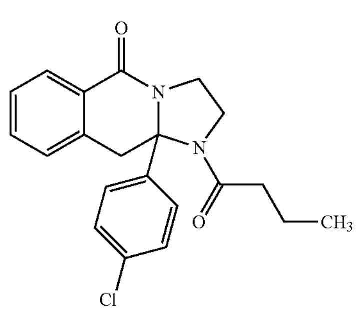 [SMILES: CCCC(=O)N1CCN2C(=O)c3ccccc3CC12c1ccc(Cl)cc1] | 369.0 | I, A, F |

TABLE 2-continued
Prepared compounds of formula I
| Compound no. | Structure | Observed m/z ([M + H]+) | Synthesis method(s) |
|---|---|---|---|
| 1-091 | 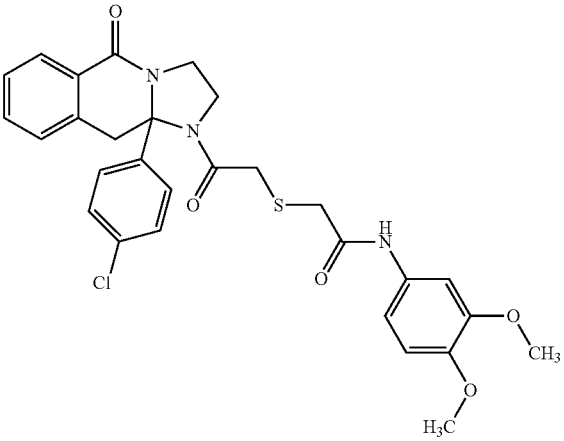 [SMILES: COc1ccc(NC(=O)CSCC(=O)N2CCN3C(=O)c4ccccc4CC23c2ccc(Cl)cc2)cc1OC] | 566.0 | I, A, F |
| 1-092 | 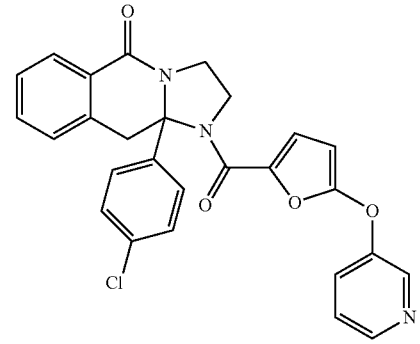 [SMILES: O=C(c1ccc(Oc2cccnc2)o1)N1CCN2C(=O)c3ccccc3CC12c1ccc(Cl)cc1] | 486.0 | I, A, F |
| 1-093 | 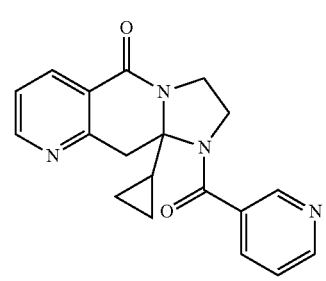 [SMILES: O=C(c1cccnc1)N1CCN2C(=O)c3cccnc3CC12C1CC1] | 335.1 | J, A, F |
| 1-094 | 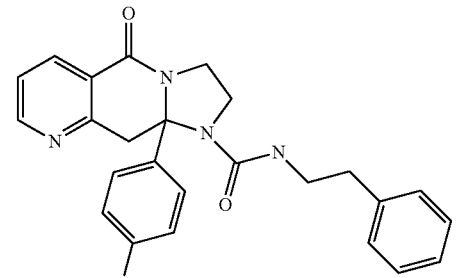 | 429.1 | J, A, F |

TABLE 2-continued

Prepared compounds of formula I

| Compound no. | Structure | Observed m/z ([M + H]+) | Synthesis method(s) |
|---|---|---|---|
| 1-095 | 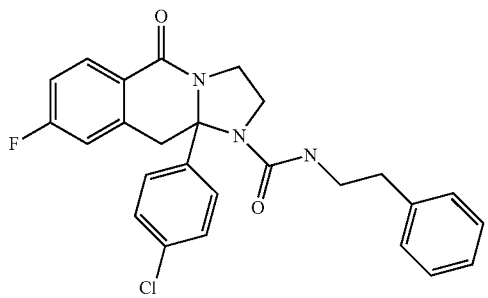 [SMILES: O=C(NCCc1ccccc1)N1CCN2C(=O)c3ccc(F)cc3CC12c1ccc(Cl)cc1] | 464.0 | J, A, F |
| 1-096 | 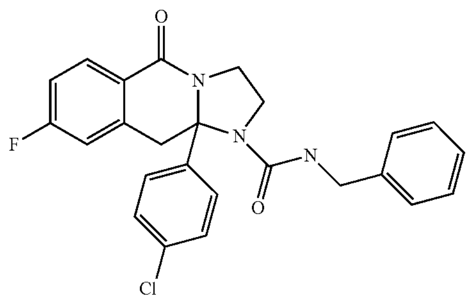 [SMILES: O=C(NCc1ccccc1)N1CCN2C(=O)c3ccc(F)cc3CC12c1ccc(Cl)cc1] | 450.0 | J, A, F |
| 1-097 | 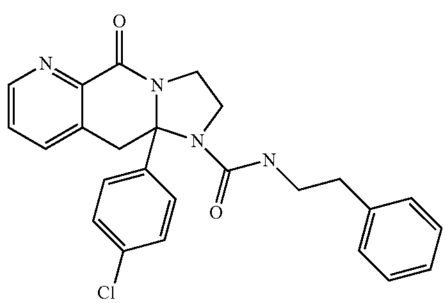 [SMILES: O=C(NCCc1ccccc1)N1CCN2C(=O)c3ncccc3CC12c1ccc(Cl)cc1] | 447.0 | J, A, F |
| 1-098 | 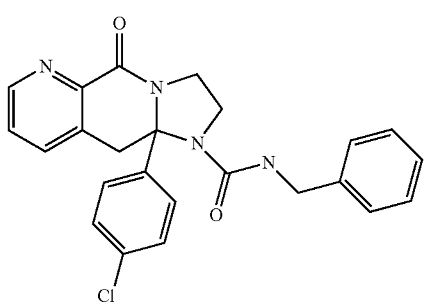 [SMILES: O=C(NCc1ccccc1)N1CCN2C(=O)c3ncccc3CC12c1ccc(Cl)cc1] | 433.3 | J, A, F |
| 1-099 | 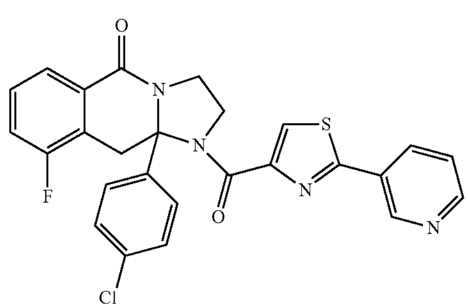 [SMILES: O=C(c1csc(-c2cccnc2)n1)N1CCN2C(=O)c3cccc(F)c3CC12c1ccc(Cl)cc1] | 505.0 | J, A, F |

TABLE 2-continued
Prepared compounds of formula I
| Compound no. | Structure | Observed m/z ([M + H]+) | Synthesis method(s) |
|---|---|---|---|
| 1-100 | 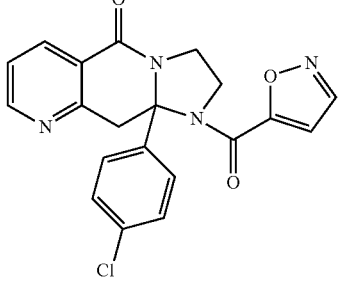 | 395.0 | H, A, F |
| 1-101 | 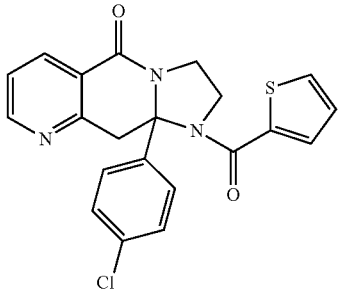 [SMILES: O=C(c1cccs1)N1CCN2C(=O)c3cccnc3CC12c1ccc(Cl)cc1] | 410.0 | H, A, F |
| 1-102 | 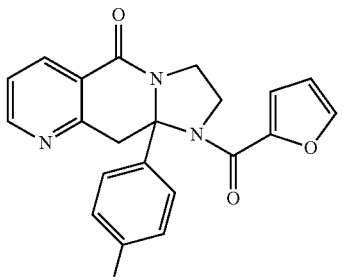 | 394.0 | H, A, F |
| 1-103 | 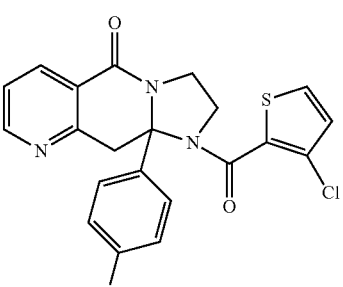 | 444.0 | H, A, F |
| 1-104 | 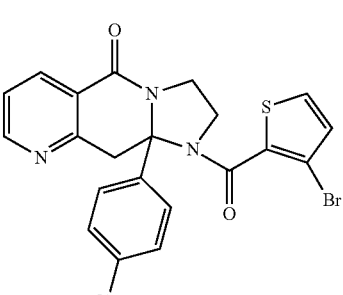 | 487.9 | H, A, F |

TABLE 2-continued

Prepared compounds of formula I

| Compound no. | Structure | Observed m/z ([M + H]⁺) | Synthesis method(s) |
|---|---|---|---|
| 1-105 | 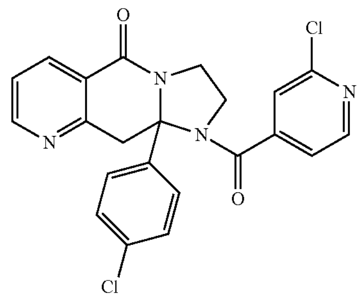 [SMILES: O=C(c1ccnc(Cl)c1)N1CCN2C(=O)c3cccnc3CC12c1ccc(Cl)cc1] | 439.0 | H, A, F |
| 1-106 | 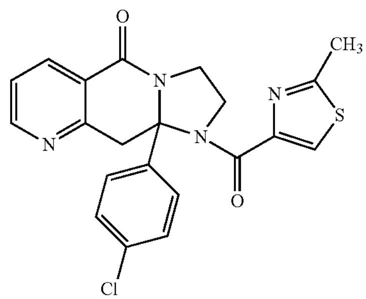 [SMILES: Cc1nc(C(=O)N2CCN3C(=O)c4cccnc4CC23c2ccc(Cl)cc2)cs1] | 425.0 | H, A, F |
| 1-107 | 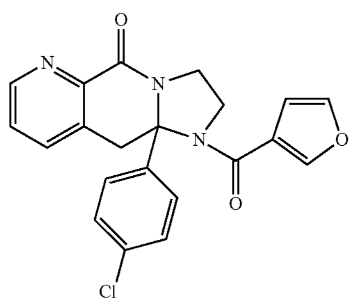 [SMILES: O=C(c1ccoc1)N1CCN2C(=O)c3ncccc3CC12c1ccc(Cl)cc1] | 394.0 | J, A, F |
| 1-108 | 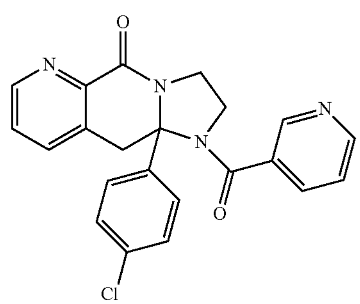 [SMILES: O=C(c1cccnc1)N1CCN2C(=O)c3ncccc3CC12c1ccc(Cl)cc1] | 405.0 | J, A, F |
| 1-109 | 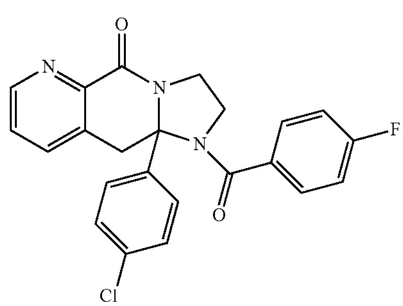 | 422.0 | J, A, F |

TABLE 2-continued

Prepared compounds of formula I

| Compound no. | Structure | Observed m/z ([M + H]+) | Synthesis method(s) |
|---|---|---|---|
| 1-110 | 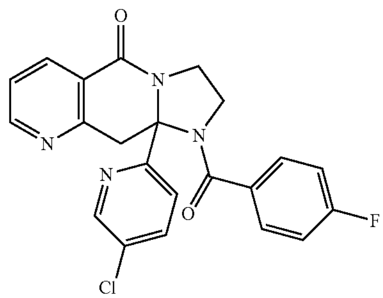 [SMILES: O=C(c1ccc(F)cc1)N1CCN2C(=O)c3cccnc3CC12c1ccc(Cl)cn1] | 423.0 | J, A, F |
| 1-111 | 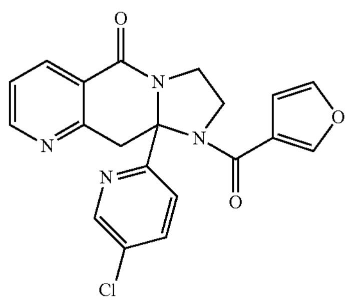 [SMILES: O=C(c1ccoc1)N1CCN2C(=O)c3cccnc3CC12c1ccc(Cl)cn1] | 395.0 | J, A, F |
| 1-112 | 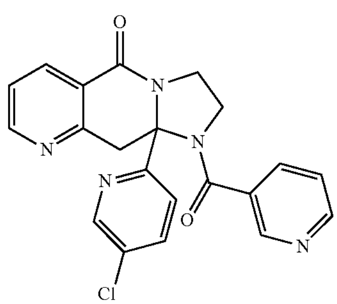 [SMILES: O=C(c1cccnc1)N1CCN2C(=O)c3cccnc3CC12c1ccc(Cl)cn1] | 406.0 | J, A, F |
| 1-113 | 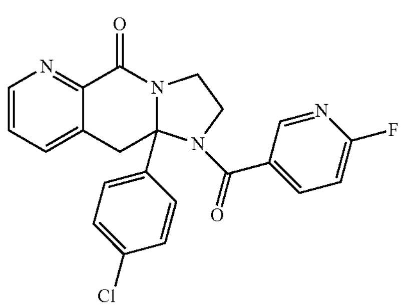 [SMILES: O=C(c1ccc(F)nc1)N1CCN2C(=O)c3ncccc3CC12c1ccc(Cl)cc1] | 423.0 | J, A, F |
| 1-114 | 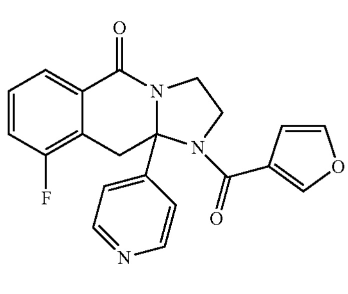 [SMILES: O=C(c1ccoc1)N1CCN2C(=O)c3cccc(F)c3CC12c1ccncc1] | 378.1 | J, A, F |

TABLE 2-continued

Prepared compounds of formula I

| Compound no. | Structure | Observed m/z ([M + H]⁺) | Synthesis method(s) |
|---|---|---|---|
| 1-115 | 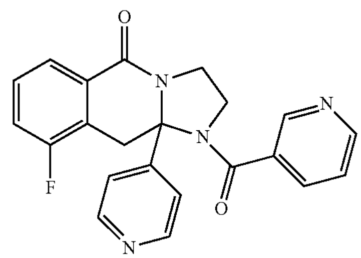 [SMILES: O=C(c1cccnc1)N1CCN2C(=O)c3cccc(F)c3CC12c1ccncc1] | 389.1 | J, A, F |
| 1-116 | 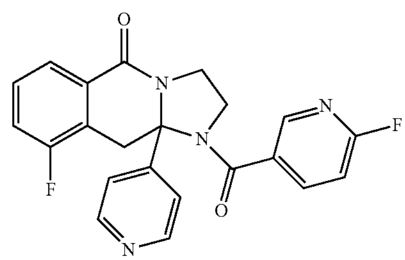 [SMILES: O=C(c1ccc(F)nc1)N1CCN2C(=O)c3cccc(F)c3CC12c1ccncc1] | 407.1 | J, A, F |
| 1-117 | 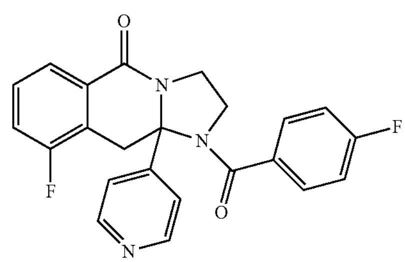 [SMILES: O=C(c1ccc(F)cc1)N1CCN2C(=O)c3cccc(F)c3CC12c1ccncc1] | 406.2 | J, A, F |
| 1-118 | 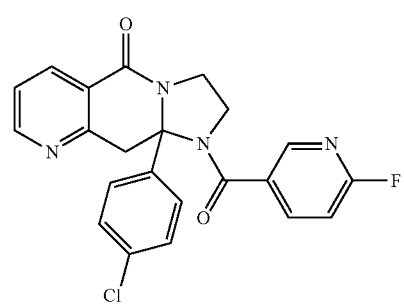 | 423.1 | J, A, F |
| 1-119 | 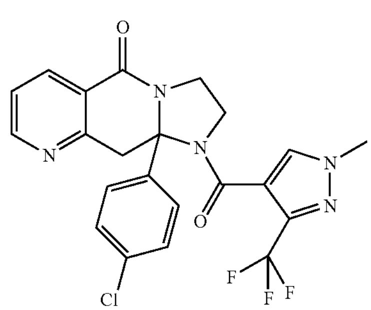 [SMILES: Cn1cc(C(=O)N2CCN3C(=O)c4cccnc4CC32c2ccc(Cl)cc2)c(C(F)(F)F)n1] | 476.1 | J, A, F |

TABLE 2-continued

Prepared compounds of formula I

| Compound no. | Structure | Observed m/z ([M + H]+) | Synthesis method(s) |
|---|---|---|---|
| 1-120 | 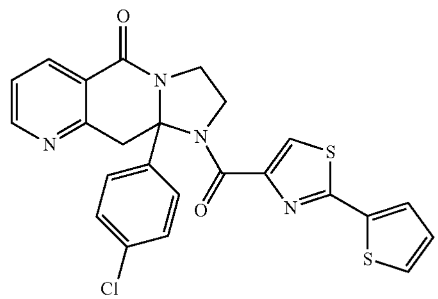 [SMILES: O=C(c1csc(-c2cccs2)n1)N1CCN2C(=O)c3cccnc3CC12c1ccc(Cl)cc1] | 493.0 | J, A, F |
| 1-121 | 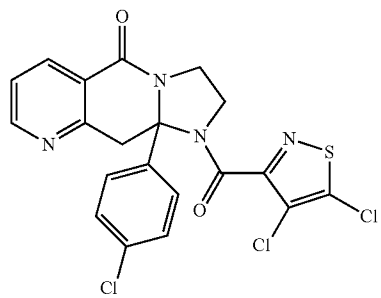 [SMILES: O=C1c2cccnc2CC2(c3ccc(Cl)cc3)N1CCN2C(=O)c1nsc(Cl)c1Cl] | 481.0 | J, A, F |
| 1-122 | 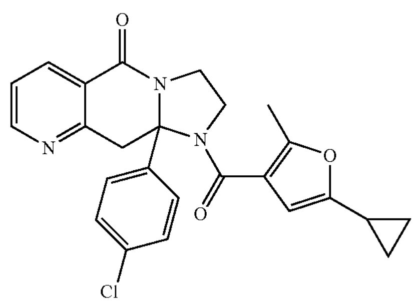 [SMILES: Cc1oc(C2CC2)cc1C(=O)N1CCN2C(=O)c3cccnc3CC21c1ccc(Cl)cc1] | 448.1 | J, A, F |
| 1-123 | 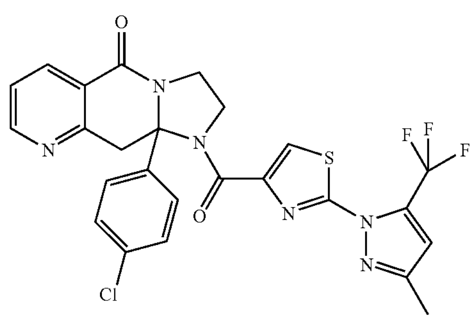 [SMILES: Cc1cc(C(F)(F)F)n(-c2nc(C(=O)N3CCN4C(=O)c5cccnc5CC34c3ccc(Cl)cc3)cs2)n1] | 559.1 | J, A, F |
| 1-124 | 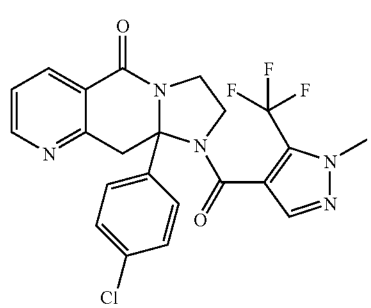 [SMILES: Cn1ncc(C(=O)N2CCN3C(=O)c4cccnc4CC32c2ccc(Cl)cc2)c1C(F)(F)F] | 476.1 | J, A, F |

TABLE 2-continued
Prepared compounds of formula I
| Compound no. | Structure | Observed m/z ([M + H]+) | Synthesis method(s) |
|---|---|---|---|
| 1-125 | 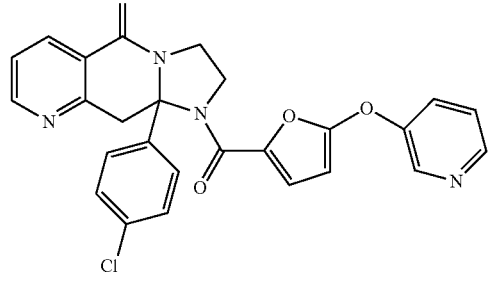 | 487.1 | J, A, F |
| 1-126 | 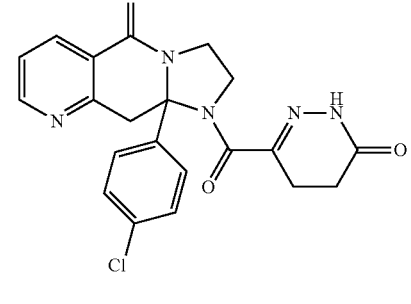 | 424.1 | J, A, F |
| 1-127 | 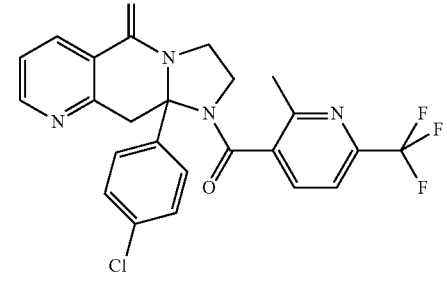 | 487.1 | J, A, F |
| 1-128 | 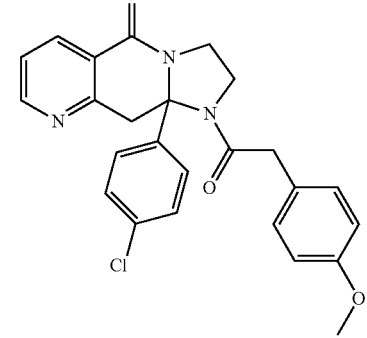 | 448.1 | J, A, F |

TABLE 2-continued
Prepared compounds of formula I
| Compound no. | Structure | Observed m/z ([M + H]+) | Synthesis method(s) |
|---|---|---|---|
| 1-129 | 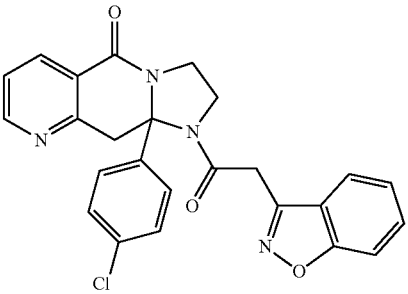 [SMILES: O=C(Cc1noc2ccccc12)N1CCN2C(=O)c3cccnc3CC12c1ccc(Cl)cc1] | 459.1 | J, A, F |
| 1-130 | 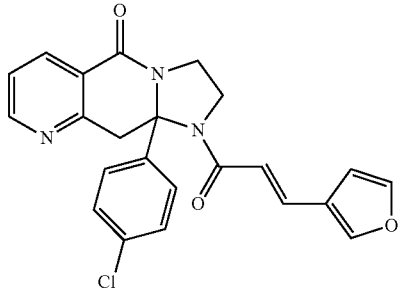 [SMILES: O=C(/C=C/c1ccoc1)N1CCN2C(=O)c3cccnc3CC12c1ccc(Cl)cc1] | 420.1 | J, A, F |
| 1-131 | 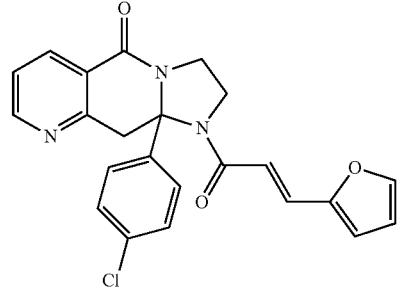 [SMILES: O=C(/C=C/c1ccco1)N1CCN2C(=O)c3cccnc3CC12c1ccc(Cl)cc1] | 420.1 | J, A, F |
| 1-132 | 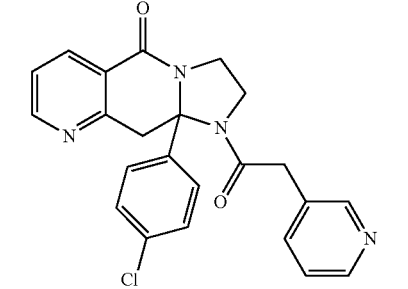 [SMILES: O=C(Cc1cccnc1)N1CCN2C(=O)c3cccnc3CC12c1ccc(Cl)cc1] | 419.1 | J, A, F |
| 1-133 | 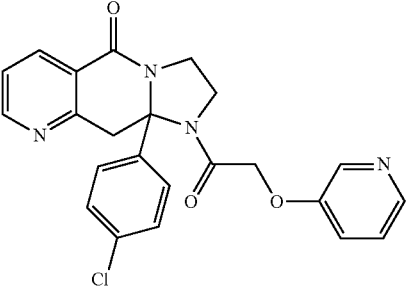 [SMILES: O=C(COc1cccnc1)N1CCN2C(=O)c3cccnc3CC12c1ccc(Cl)cc1] | 435.1 | J, A, F |

TABLE 2-continued
Prepared compounds of formula I
| Compound no. | Structure | Observed m/z ([M + H]+) | Synthesis method(s) |
|---|---|---|---|
| 1-134 | 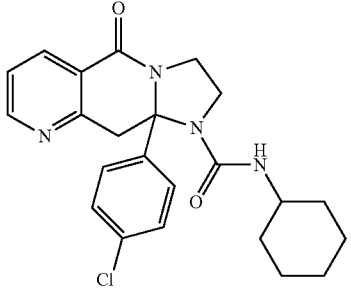 [SMILES: O=C(NC1CCCCC1)N1CCN2C(=O)c3cccnc3CC12c1ccc(Cl)cc1] | 425.0 | J, A, F |
| 1-135 | 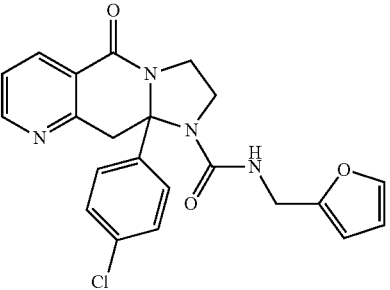 [SMILES: O=C(NCc1ccco1)N1CCN2C(=O)c3cccnc3CC12c1ccc(Cl)cc1] | 423.0 | J, A, F |
| 1-136 | 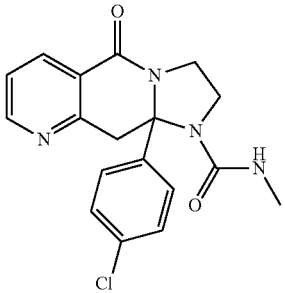 [SMILES: CNC(=O)N1CCN2C(=O)c3cccnc3CC12c1ccc(Cl)cc1] | 357.0 | J, A, F |
| 1-137 | 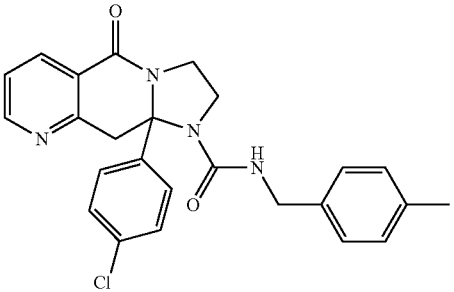 [SMILES: Cc1ccc(CNC(=O)N2CCN3C(=O)c4cccnc4CC23c2ccc(Cl)cc2)cc1] | 447.1 | J, A, F |
| 1-138 | 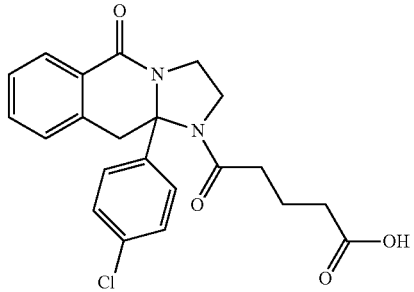 [SMILES: O=C(O)CCCC(=O)N1CCN2C(=O)c3ccccc3CC12c1ccc(Cl)cc1] | 413.0 | J, A, C |

TABLE 2-continued

Prepared compounds of formula I

| Compound no. | Structure | Observed m/z ([M + H]+) | Synthesis method(s) |
|---|---|---|---|
| 1-139 | 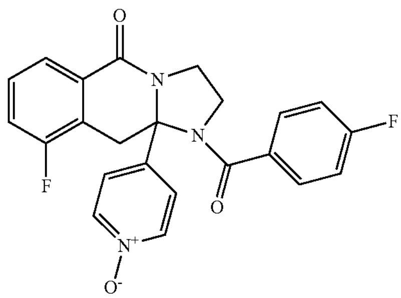 [SMILES: O=C(c1ccc(F)cc1)N1CCN2C(=O)c3cccc(F)c3CC12c1cc[n+]([O-])cc1] | 422.1 | J, A, F, G |
| 1-140 | 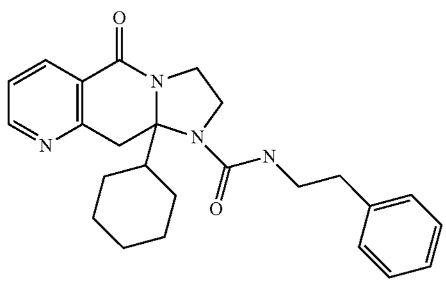 [SMILES: O=C(NCCc1ccccc1)N1CCN2C(=O)c3cccnc3CC12C1CCCCC1] | 419.1 | J, A, F |
| 1-141 | 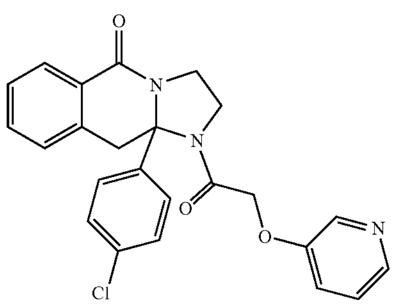 [SMILES: O=C(COc1cccnc1)N1CCN2C(=O)c3ccccc3CC12c1ccc(Cl)cc1] | 434.1 | I, A, F |
| 1-142 | 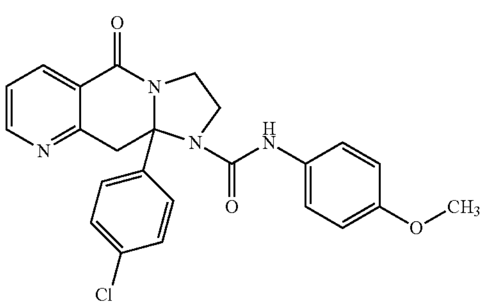 [SMILES: COc1ccc(NC(=O)N2CCN3C(=O)c4cccnc4CC23c2ccc(Cl)cc2)cc1] | 449.0 | H, A, F |
| 1-143 | 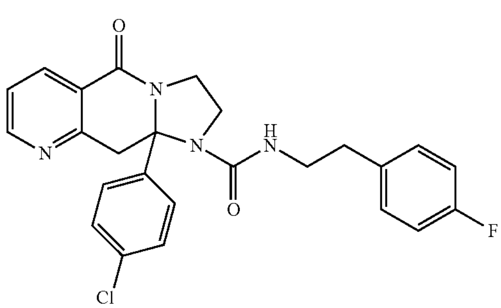 [SMILES: O=C(NCCc1ccc(F)cc1)N1CCN2C(=O)c3cccnc3CC12c1ccc(Cl)cc1] | 465.0 | H, A, F |

TABLE 2-continued
Prepared compounds of formula I
| Compound no. | Structure | Observed m/z ([M + H]+) | Synthesis method(s) |
|---|---|---|---|
| 1-144 | 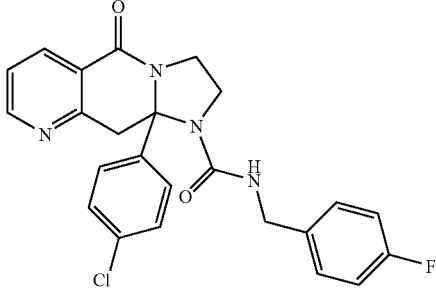 [SMILES: O=C(NCc1ccc(F)cc1)N1CCN2C(=O)c3cccnc3CC12c1ccc(Cl)cc1] | 451.0 | H, A, F |
| 1-145 | 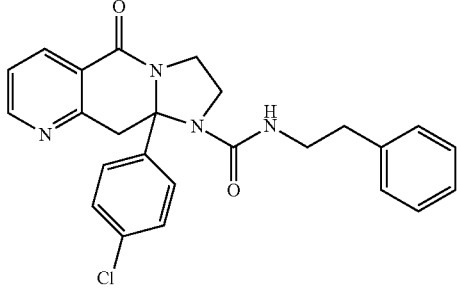 [SMILES: O=C(NCCc1ccccc1)N1CCN2C(=O)c3cccnc3CC12c1ccc(Cl)cc1] | 447.0 | H, A, F |
| 1-146 | 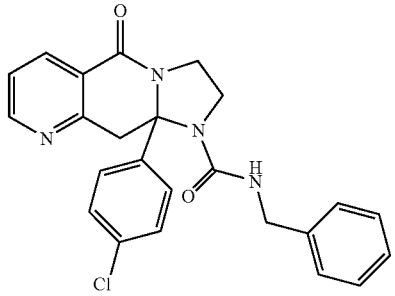 [SMILES: O=C(NCc1ccccc1)N1CCN2C(=O)c3cccnc3CC12c1ccc(Cl)cc1] | 433.0 | H, A, F |
| 1-147 | 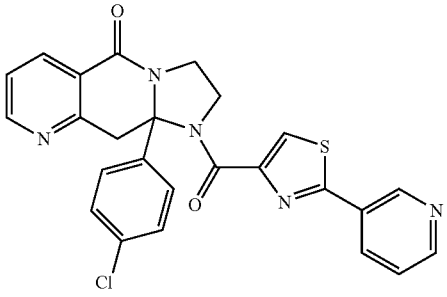 [SMILES: O=C(c1csc(-c2cccnc2)n1)N1CCN2C(=O)c3cccnc3CC12c1ccc(Cl)cc1] | 488.0 | H, A, F |
| 1-148 | 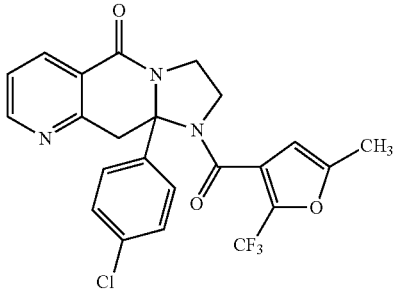 [SMILES: Cc1cc(C(=O)N2CCN3C(=O)c4cccnc4CC32c2ccc(Cl)cc2)c(C(F)(F)F)o1] | 476.1 | H, A, F |

TABLE 2-continued

Prepared compounds of formula I

| Compound no. | Structure | Observed m/z ([M + H]⁺) | Synthesis method(s) |
|---|---|---|---|
| 1-149 | 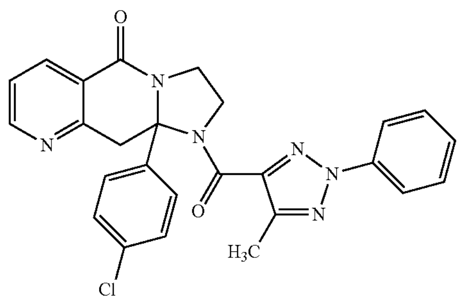 [SMILES: Cc1nn(-c2ccccc2)nc1C(=O)N1CCN2C(=O)c3cccnc3CC21c1ccc(Cl)cc1] | 485.1 | H, A, F |
| 1-150 | 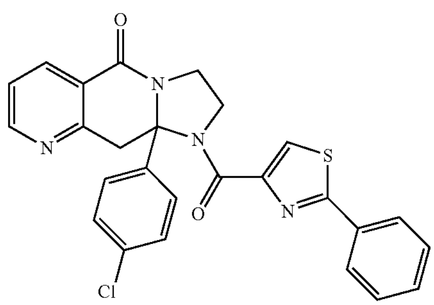 [SMILES: O=C(c1csc(-c2ccccc2)n1)N1CCN2C(=O)c3cccnc3CC12c1ccc(Cl)cc1] | 487.0 | H, A, F |
| 1-151 | 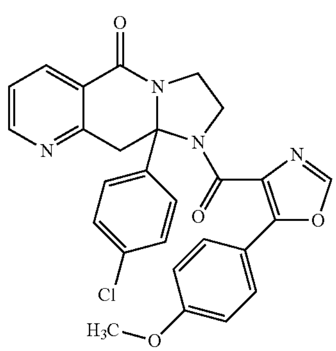 [SMILES: COc1ccc(-c2ocnc2C(=O)N2CCN3C(=O)c4cccnc4CC32c2ccc(Cl)cc2)cc1] | 501.1 | H, A, F |
| 1-152 | 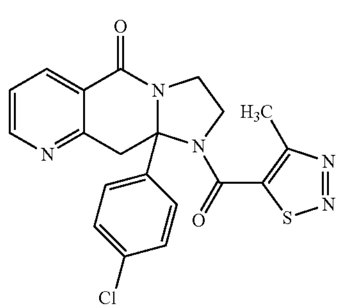 [SMILES: Cc1nnsc1C(=O)N1CCN2C(=O)c3cccnc3CC21c1ccc(Cl)cc1] | 426.0 | H, A, F |

TABLE 2-continued

Prepared compounds of formula I

| Compound no. | Structure | Observed m/z ([M + H]+) | Synthesis method(s) |
|---|---|---|---|
| 1-153 | 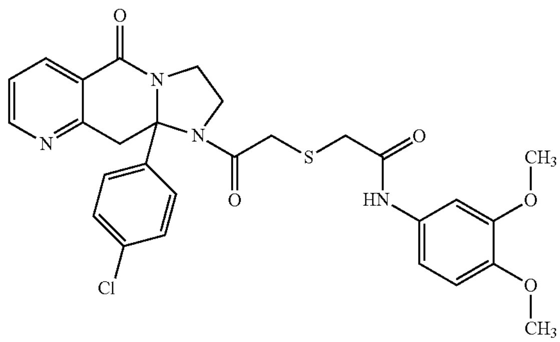 [SMILES: COc1ccc(NC(=O)CSCC(=O)N2CCN3C(=O)c4cccnc4CC23c2ccc(Cl)cc2)cc1OC] | 567.1 | H, A, F |
| 1-154 | 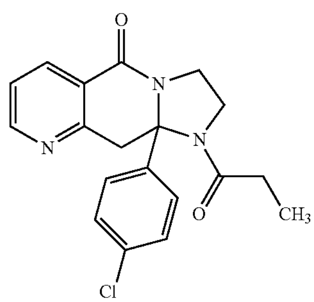 [SMILES: CCC(=O)N1CCN2C(=O)c3cccnc3CC12c1ccc(Cl)cc1] | 356.0 | H, A, F |

TABLE 3

Prepared compounds of formula III

| Compound no. | Structure | Observed m/z ([M + H]+) | Synthesis method(s) |
|---|---|---|---|
| 2-01 | 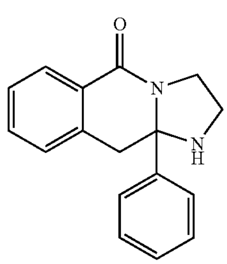 [SMILES: O=C1c2ccccc2CC2(c3ccccc3)NCCN12] | 265.0 | H, A |
| 2-02 | 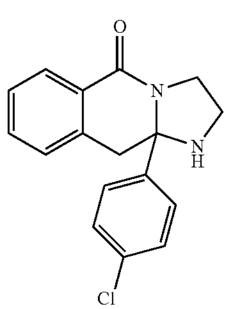 [SMILES: O=C1c2ccccc2CC2(c3ccc(Cl)cc3)NCCN12] | 298.9 | I, A |
| 2-03 | | 300.0 | H, A |
| 2-04 | | 300.0 | H, A |

TABLE 3-continued

Prepared compounds of formula III

| Compound no. | Structure | Observed m/z ([M + H]+) | Synthesis method(s) |
|---|---|---|---|
| 2-05 | 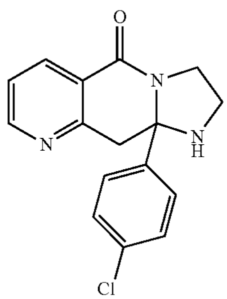 [SMILES: O=C1c2cccnc2CC2(c3ccc(Cl)cc3)NCCN12] | 300.0 | H, A |
| 2-06 | 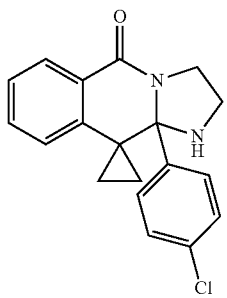 [SMILES: O=C1c2ccccc2C2(CC2)C2(c3ccc(Cl)cc3)NCCN12] | 325.0 | I, K, A |
| 2-07 | 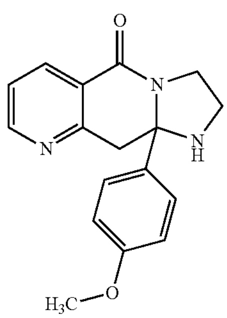 [SMILES: COc1ccc(C23Cc4ncccc4C(=O)N2CCN3)cc1] | 295.9 | J, A |
| 2-08 | 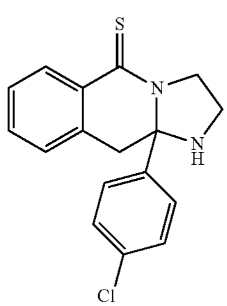 [SMILES: S=C1c2ccccc2CC2(c3ccc(Cl)cc3)NCCN12] | 314.8 | I, A, N |
| 2-09 | 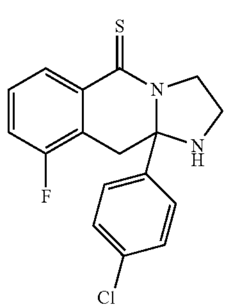 [SMILES: Fc1cccc2c1CC1(c3ccc(Cl)cc3)NCCN1C2=S] | 317.0 | J, A |
| 2-10 | | 317.0 | J, A |
| 2-11 | | 327.0 | I, K, A |
| 2-12 | | 295.0 | I, A |
| 2-13 | | 300.1 | J, A |
| 2-14 | | 272.0 | J, A |

TABLE 3-continued

Prepared compounds of formula III

| Compound no. | Structure | Observed m/z ([M + H]$^+$) | Synthesis method(s) |
|---|---|---|---|
| 2-15 | 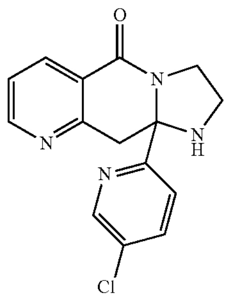 [SMILES: O=C1c2cccnc2CC2(c3ccc(Cl)cn3)NCCN12] | 301.0 | J, A |
| 2-16 | 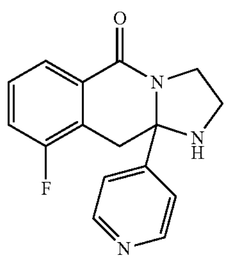 [SMILES: O=C1c2cccc(F)c2CC2(c3ccncc3)NCCN12] | 284.1 | J, A |
| 2-17 | 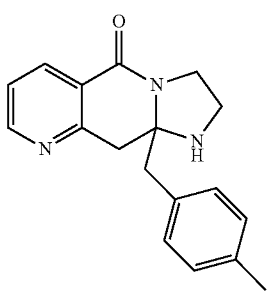 [SMILES: Cc1ccc(CC23Cc4ncccc4C(=O)N2CCN3)cc1] | 294.0 | J, A |
| 2-18 | 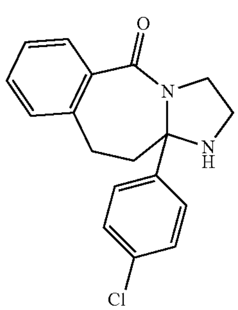 [SMILES: O=C1c2ccccc2CCC2(c3ccc(Cl)cc3)NCCN12] | 313.0 | L, A |
| 2-19 | 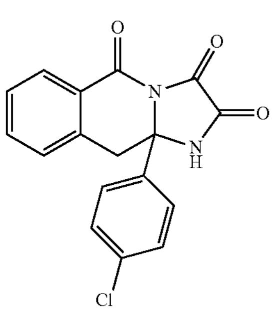 [SMILES: O=C1NC2(c3ccc(Cl)cc3)Cc3ccccc3C(=O)N2C1=O] | 326.9 | L, A, M |
| 2-20 | 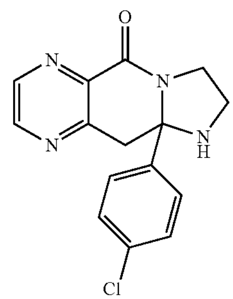 [SMILES: O=C1c2nccnc2CC2(c3ccc(Cl)cc3)NCCN12] | 300.9 | J, A |

Biological Data

Method P: RSV Antiviral Assay Protocol

Compounds of the invention were tested for their antiviral activity against respiratory syncytial virus. Cytopathic effect (CPE) assays were performed essentially as described in the literature (see for example Watanabe et al, 1994, J. Virological Methods, 48:257). Serial dilutions of the test compounds were made in 96 well plates. HEp2 cells ($1.0 \times 10^4$ cells/well) were infected with RSV at a low multiplicity of infection (e.g. RSV A2 at an moi of ~0.01) and added to plates to assess antiviral activity. Uninfected HEp2 cells were used to assess compound cytotoxicity. Assays were incubated for 5 days at 37° C. in a 5% $CO_2$ atmosphere. The extent of CPE was determined via metabolism of the vital dye 3-(4,5-dimethylthiaxol-2-yl)-2,5-diphenyltetrazolium bromide (MTT). MTT (1 mg/ml) was added to each well and plates incubated for 2 hours incubation at 37° C. Wells were aspirated, isopropanol (200 µL) was added and absorbance values read at 540/690 nm. Compound concentrations that inhibited CPE by 50% ($EC_{50}$) and developed cytotoxicity ($CC_{50}$) were calculated using non-linear regression analysis.

Representative data for compounds of the invention against RSV A2 are shown in Tables 4 and 5 where $EC_{50}$ values lie in the ranges A: <0.25 µM, B: 0.25-1.0 µM, C: 1.0-5.0 µM and D: >5.0 µM.

TABLE 4

RSV A2 Antiviral Data for Compounds of Table 2

| Cpd No. | Activity Range | Cpd No. | Activity Range |
|---|---|---|---|
| 1-001 | B | 1-029 | B |
| 1-002 | B | 1-043 | A |
| 1-003 | B | 1-066 | C |
| 1-005 | D | 1-069 | B |
| 1-006 | A | 1-071 | A |
| 1-007 | C | 1-073 | B |
| 1-008 | C | 1-077 | C |
| 1-010 | B | 1-079 | B |
| 1-014 | C | 1-083 | B |
| 1-015 | B | 1-087 | A |
| 1-019 | B | 1-101 | A |
| 1-025 | C | 1-109 | C |

TABLE 4

RSV A2 Antiviral Data for Compounds of Table 1

| Cpd No. | Activity Range | Cpd No. | Activity Range |
|---------|----------------|---------|----------------|
| 1-019a  | D              | 1-019b  | B              |
| 1-008a  | D              | 1-008b  | C              |
| 1-006a  | D              | 1-006b  | A              |
| 1-029a  | D              | 1-029b  | B              |
| 1-031a  | D              | 1-031b  | B              |
| 1-036a  | D              | 1-036b  | A              |
| 1-043a  | D              | 1-043b  | A              |

Method Q: RSV Fusion Assay

Selected compounds of the invention can be tested for their ability to inhibit the essential fusion processes of the respiratory syncytial virus.

Generation of RSV-F Constructs

Single-stranded synthetic DNA oligonucleotides encoding the portions of RSV A2 F glycoprotein incorporating optimal codons and without potential poly(A) addition or splice sites were generated synthetically (Mason et al, WO0242326). A membrane-anchored full-length F was generated essentially according to the method described therein and in Morton et al.

Syncytium Formation Assay

Fusion activity of the RSV-F constructs was measured in 293 cells essentially according to the method described in Morton et al, 2003, Virology, 311:275. For example: cells in six well plates at approximately 80% confluency were transfected by adding plasmid DNA (2 μg/well) carrying the constructs of interest in CaPO$_4$ solution for 4 hours. After glycerol shock and wash, the transfected cells were trypsinized and 1.5×10$^4$ cells/well added to 96-well plates containing half-log serial dilutions of the test compound. Syncytium formation was evaluated by visual inspection and quantified at 48 hours post-transfection by addition of 20 μL of CellTiter 96 One Solution (Promega) followed by incubation for 4 hours at 37° C. The colour reaction was then stopped by addition of 25 μL 10% SDS to each well and absorbance values read at 540/690 nm. The compound concentration that reduced absorbance relative to untreated control cultures by 50% (EC$_{50}$) was calculated using non-linear regression analysis.

Method R: RSV Cotton Rat Model

The cotton rat model was performed essentially as described in the literature (Wyde et al, 2003, Antiviral Res., 60:221). Briefly, cotton rats weighing 50-100 g were lightly anesthetized with isoflurane and dosed orally with 100 mg/kg/day of compound or vehicle control. Viral infection followed 2 hours post-treatment in similarly anesthetized rats by intranasal instillation with approximately 1000 TCID$_{50}$ of RSV A2 per animal. Four days after virus inoculation, each cotton rat was sacrificed and their lungs removed and RSV titres determined by plaque assay.

Method S: RSV Balb/c Mouse Model

The mouse model was performed essentially as described by Clanci et al, 2004, Antimicrobial Agents and Chemotherapy., 48:413). Briefly, eight week old female Balb/c mice were weighed, anesthetized intraperitoneally with Avertin™ and compound or vehicle administered orally 6 hours preinfection. Mice were inoculated intranasally with approximately 10000 TCID$_{50}$ RSV A2 per animal. Three days after virus inoculation, each mouse was sacrificed and their lungs removed and RSV titres determined by plaque assay.

The claims defining the invention are as follows:

1. A compound of formula I or salt thereof

Formula I wherein:

R$_1$ is selected from C$_{1-12}$ alkyl, C$_{2-12}$ alkenyl, C$_{2-12}$ alkynyl, —(CH$_2$)$_n$C$_{3-7}$ cycloalkyl, —(CH$_2$)$_n$C$_{4-7}$ cycloalkenyl, —(CH$_2$)$_n$aryl, —(CH$_2$)$_n$aryl C$_{1-12}$ alkyl, —(CH$_2$)$_n$arylC$_{2-12}$ alkenyl, —(CH$_2$)$_n$arylC$_{2-12}$ alkynyl, and —(CH$_2$)$_n$ heterocyclyl; n is 0-6; and said alkyl, alkenyl, alkynyl, cycloalkyl, cycloalkenyl, aryl and heterocyclyl groups are optionally substituted;

R$_2$ is selected from H, O, —CH$_2$R$_3$, —C(=Y)R$_3$, —C(=Y)OR$_3$, —C(=Y)N(R$_4$)R$_3$, —C(=Y)CH$_2$N(R$_4$)R$_3$, —C(=Y)CH$_2$SR$_3$ and —S(O)$_w$R$_5$, where R$_3$ is selected from hydrogen, C$_{1-12}$ alkyl, C$_{2-12}$ alkenyl, C$_{2-12}$ alkynyl, —(CH$_2$)$_m$C$_{3-7}$ cycloalkyl, —(CH$_2$)$_m$C$_{4-7}$ cycloalkenyl, —(CH$_2$)$_m$ aryl, —(CH$_2$)$_m$ arylC$_{1-12}$ alkyl, —(CH$_2$)$_m$ arylC$_{2-12}$ alkenyl, —(CH$_2$)$_m$ arylC$_{2-12}$ alkynyl and —(CH$_2$)$_m$ heterocyclyl; and when R$_2$ is —CH$_2$R$_3$, or —C(=Y)R$_3$, R$_3$ may also be selected from —S—R$_5$ and —O—R$_5$; m is 0-6; R$_4$ is hydrogen or C$_{1-6}$ alkyl; R$_5$ is C$_{1-6}$ alkyl, C$_{2-6}$ alkenyl, C$_{2-6}$ alkynyl, C$_{3-7}$ cycloalkyl, C$_{4-7}$ cycloalkenyl, benzyl, aryl or heterocyclyl; w is 0, 1 or 2; and the alkyl, alkenyl, alkynyl, cycloalkyl, cycloalkenyl, aryl and heterocyclyl groups are optionally substituted;

X is O and Y is selected from O, S and NR$_6$, where R$_6$ is independently selected from hydrogen, C$_{1-6}$ alkyl, hydroxy and C$_{1-6}$ alkoxy;

A together with the atoms to which it is attached forms an optionally substituted phenyl;

B—C is —CH$_2$CH$_2$; and

D is —CH$_2$, provided that when A together with the atoms to which it is attached forms an unsubstituted phenyl ring, and R$_1$ is unsubstituted phenyl, then R$_2$ is not H.

2. A compound according to claim 1, wherein R$_1$ represents an optionally substituted aryl, optionally substituted alkyl or optionally substituted heterocyclyl.

3. A compound according to claim 2, wherein R$_1$ represents an optionally substituted phenyl, optionally substituted thienyl, optionally substituted pyrrolyl or optionally substituted pyridyl.

4. A compound according to claim 3, wherein R$_1$ represents an optionally substituted phenyl ring.

5. A compound according to claim 1, wherein R$_1$ is optionally substituted phenyl, where the substituents are each independently selected from halo, hydroxy or alkoxy; cycloalkyl; and optionally halo-substituted pyridyl and an N-oxide thereof.

6. A compound according to claim 5, wherein R$_1$ is optionally substituted phenyl, where the substituents are each independently selected from chloro, hydroxy or methoxy; C$_{3-7}$ cycloalkyl; and optionally halo-substituted pyridyl and an N-oxide thereof.

7. A compound according to claim 5, wherein R$_1$ is phenyl, 4-chlorophenyl, 4-methoxyphenyl, 4-hydroxyphenyl, 5-chloro-2-pyridyl, 4-pyridyl or 4-pyridyl N-oxide.

8. A compound according to claim 1, wherein R$_2$ is selected from O, —CH$_2$R$_3$, —C(=Y)R$_3$, —C(=Y)OR$_3$, —C(=Y)

—N(R$_4$)R$_3$, —C(=Y)CH$_2$N(R$_4$)R$_3$, —C(=Y)CH$_2$SR$_3$ and —S(O)$_w$R$_5$; where R$_3$ is selected from hydrogen, C$_{1-12}$ alkyl, C$_{2-12}$ alkenyl, C$_{2-12}$ alkynyl, —(CH$_2$)$_m$C$_{3-7}$ cycloalkyl, —(CH$_2$)$_m$C$_{4-7}$ cycloalkenyl, —(CH$_2$)$_m$ aryl, —(CH$_2$)$_m$arylC$_{1-12}$ alkyl, —(CH$_2$)$_m$ arylC$_{2-12}$ alkenyl, —(CH$_2$)$_m$arylC$_{2-12}$ alkynyl and —(CH$_2$)$_m$ heterocyclyl; and when R$_2$ is —CH$_2$R$_3$, or —C(=Y)R$_3$, R$_3$ may also be selected from —S—R$_5$ and —O—R$_5$; m is 0-6; R$_4$ is hydrogen or C$_{1-6}$ alkyl; R$_5$ is C$_{1-6}$ alkyl, C$_{2-6}$ alkenyl, C$_{2-6}$ alkynyl, C$_{3-7}$ cycloalkyl, C$_{4-7}$cycloalkenyl, benzyl, aryl or heterocyclyl; w is 0, 1 or 2; and the alkyl, alkenyl, alkynyl, cycloalkyl, cycloalkenyl, aryl and heterocyclyl groups are optionally substituted.

9. A compound according to claim 1, where R$_2$ is —CH$_2$—R$_3$, wherein R$_3$ is —(CH$_2$)$_m$ optionally substituted aryl or —(CH$_2$)$_m$ optionally substituted heterocyclyl, and m is 0 to 3.

10. A compound according to claim 1, where R$_2$ is —C(=Y)CH$_2$N(R$_4$)R$_3$ or —C(=Y)CH$_2$SR$_3$, wherein R$_3$ is —(CH$_2$)$_m$ optionally substituted aryl or —(CH$_2$)$_m$ optionally substituted heterocyclyl, m is 0 to 3, Y is O, and R$_4$ is H or C$_{1-6}$ alkyl.

11. A compound according to claim 1, where R$_2$ is —CON(R$_4$)R$_3$, wherein R$_4$ is H, R$_3$ is —(CH$_2$)$_m$ optionally substituted aryl or —(CH$_2$)$_m$ optionally substituted heteroaryl, and m is 0 to 2.

12. A compound according to claim 1, where R$_2$ is —C(=Y)R$_3$, wherein Y is O or S, R$_3$ is —(CH$_2$)$_m$ optionally substituted aryl or —(CH$_2$)$_m$ optionally substituted heteroaryl, and m is 0 to 3.

13. A compound according to claim 12, wherein Y is O, m is 0, and R$_3$ is an optionally substituted 5 or 6 membered monocyclic heterocycle, an optionally substituted 9 or 10 membered bicyclic heterocycle or an optionally substituted aryl group.

14. A compound according to claim 1, wherein R$_2$ is —CH$_2$R$_3$, —C(=O)R$_3$, —C(=O)N(R$_4$)R$_3$ or —SO$_2$R$_5$; where:
  a. R$_3$ in —CH$_2$R$_3$ or —C(=O)R$_3$ is (i) optionally substituted alkyl, where the substituents are each independently selected from —COOH, —SCH$_2$CONHaryl, —NHSO$_2$aryl, heteroaryl and aryl, each further optionally independently substituted with halo or alkoxy; (ii) optionally substituted phenyl, where the substituents are each independently selected from halo; (iii) optionally substituted 5- or 6-membered heteroaryl, where the substituents are each independently selected from halo, alkyl, haloalkyl, cycloalkyl, aryl, heteroaryloxy, and heteroaryl optionally substituted with alkyl or haloalkyl; or (iv) optionally substituted alkenyl, where the substituents are each independently selected from heteroaryl;
  b. R$_4$ is H;
  c. R$_3$ in —C(=O)N(R$_4$)R$_3$ is cycloalkyl, heteroaralkyl, alkyl, aralkyl, or heteroaryl; and
  d. R$_5$ is heteroaryl.

15. A compound according to claim 1, wherein R$_2$ is —CH$_2$R$_3$, —C(=O)R$_3$, —C(=O)N(R$_4$)R$_3$ or —SO$_2$R$_5$; where:
  a. R$_3$ in —CH$_2$R$_3$ or —C(=O)R$_3$ is (i) optionally substituted methyl, ethyl, or propyl, where the substituents are each independently selected from —COOH, —SCH$_2$CONH-3,4-dimethoxyphenyl, —NHSO$_2$-4-fluorophenyl, pyridyloxy, benzisoxazolyl, pyridyl, furyl, 4-fluorophenyl, and 4-methoxyphenyl; (ii) optionally substituted phenyl, where the substituents are each independently selected from methoxy, F and Cl; (iii) optionally substituted thiazolyl, pyridyl, furyl, thienyl, isoxazolyl, isothiazolyl, 1,2,3-thiadiazolyl, or pyrazolyl, where the substituents are each independently selected from pyridyloxy, cyclopropyl, Me, CF$_3$, phenyl, thienyl, pyridyl, F, Cl, Br, and 5-CF$_3$-3-methyl-1-pyrazolyl; or (iv) 2-furylethen-1-yl;
  b. R$_4$ is H;
  c. R$_3$ in —C(=O)N(R$_4$)R$_3$ is 2-pheneth-1-yl, benzyl, cyclohexyl, 2-furylmethyl, methyl, 4-methylbenzyl, or pyridyl; and
  d. R$_5$ is pyridyl.

16. A compound according to claim 13, wherein R$_3$ is selected from phenyl, furyl, thienyl, pyridyl, oxazolyl, thiazolyl, pyrazolyl, furazanyl, isoxazolyl, isothiazolyl, 1,2,3-triazolyl, 1,3,4-triazolyl, 1,2,3-thiadiazolyl, 1,3,4-thiadiazolyl, pyridazinyl, pyrimidinyl, benzo[b]furanyl, benzo[b]thiophenyl and benzoisoxazolyl; each of which may be optionally substituted.

17. A compound according to claim 1, where R$_2$ is —COR$_3$; wherein R$_3$ is selected from phenyl, furyl, thienyl, pyridyl, oxazolyl, thiazolyl, pyrazolyl, furazanyl, isoxazolyl, isothiazolyl, 1,2,3-triazolyl, 1,3,4-triazolyl, 1,2,3-thiadiazolyl, 1,3,4-thiadiazolyl, pyridazinyl, pyrimidinyl, benzo[b]furanyl, benzo[b]thiophenyl and benzoisoxazolyl, each of which may be optionally substituted.

18. A compound according to claim 1, wherein R$_1$ is an optionally substituted phenyl, and R$_2$ is —C(O)Optionally substituted aryl or —C(O)Optionally substituted heterocyclyl.

19. A compound according to claim 1, wherein ring A is an unsubstituted phenyl ring.

20. A pharmaceutical composition comprising a compound of formula Ia or salt thereof:

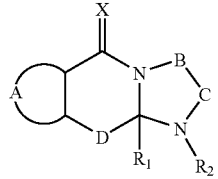

Formula Ia wherein:
R$_2$ is selected from H, O, —CH$_2$R$_3$, —C(=Y)R$_3$, —C(=Y)OR$_3$, —C(=Y)N(R$_4$)R$_3$, —(CH$_2$)$_n$C$_{4-7}$ cycloalkenyl, —(CH$_2$)$_n$ aryl, —(CH$_2$)$_n$ arylC$_{1-12}$ alkyl, —(CH$_2$)$_n$ arylC$_{2-12}$ alkenyl, —(CH$_2$)$_n$arylC$_{2-12}$alkynyl, and —(CH$_2$)$_n$ heterocyclyl; n is 0-6; and said alkyl, alkenyl, alkynyl, cycloalkyl, cycloalkenyl, aryl and heterocyclyl groups are optionally substituted;

R$_2$ is selected from O, —CH$_2$R$_3$, —C(=Y)R$_3$, —C(=Y)OR$_3$, —C(=Y)N(R$_4$)R$_3$, —C(=Y)CH$_2$N(R$_4$)R$_3$, —C(=Y)CH$_2$SR$_3$ and —S(O)$_w$R$_5$, where R$_3$ is selected from hydrogen, C$_{1-12}$ alkyl, C$_{2-12}$ alkenyl, C$_{2-12}$ alkynyl, —(CH$_2$)$_m$C$_{3-7}$cycloalkyl, —(CH$_2$)$_m$C$_{4-7}$ cycloalkenyl, —(CH$_2$)$_m$ aryl, —(CH$_2$)$_m$ arylC$_{1-12}$ alkyl, —(CH$_2$)$_m$ arylC$_{2-12}$ alkenyl, —(CH$_2$)$_m$ arylC$_{2-12}$ alkynyl and —(CH$_2$)$_m$ heterocyclyl; and when R$_2$ is —CH$_2$R$_3$, or —C(=Y)R$_3$, R$_3$ may also be selected from —S—R$_5$ and —O—R$_5$; m is 0-6; R$_4$ is hydrogen or C$_{1-6}$ alkyl; R$_5$ is C$_{1-6}$ alkyl, C$_{2-6}$ alkenyl, C$_{2-6}$ alkynyl, C$_{3-7}$ cycloalkyl, C$_{4-7}$ cycloalkenyl, benzyl, aryl or heterocyclyl; w is 0, 1 or 2; and the alkyl, alkenyl, alkynyl, cycloalkyl, cycloalkenyl, aryl and heterocyclyl groups are optionally substituted;

X is O and Y is selected from O, S and NR$_6$, where R$_6$ is independently selected from hydrogen, C$_{1-6}$ alkyl, hydroxy and C$_{1-6}$alkoxy;

A together with the atoms to which it is attached forms an optionally substituted aryl phenyl;

B—C is —CH$_2$CH$_2$—; and

D is —CH$_2$—, and at least one pharmaceutically acceptable adjuvant, carrier or diluent, provided that when A together with the atoms to which it is attached forms an unsubstituted phenyl ring, and R$_1$ is unsubstituted phenyl, then R$_2$ is not H.

21. A pharmaceutical composition according to claim 20, further comprising one or more anti-viral actives, selected from ribavirin, respiratory syncytial virus immunoglobulin, and palivizumab.

22. A compound selected from the group consisting of:

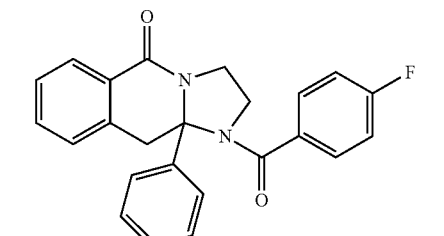

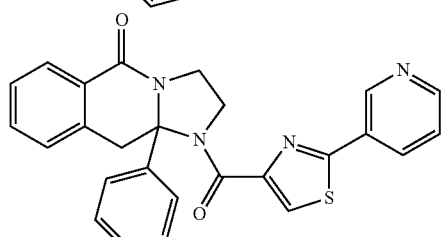

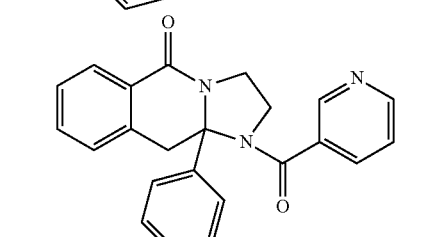

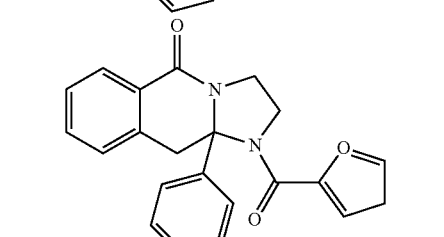

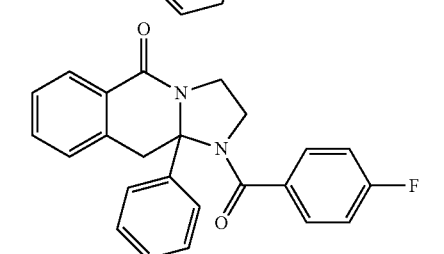

-continued

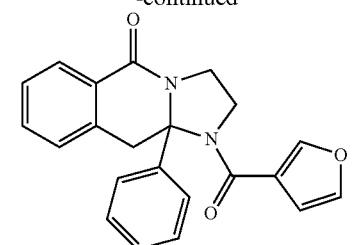

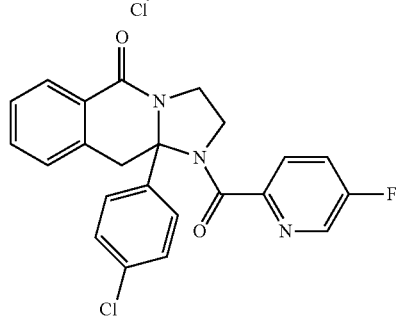

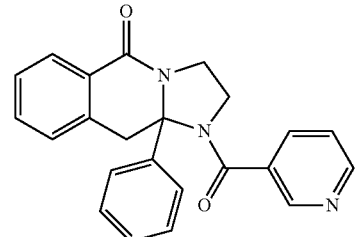

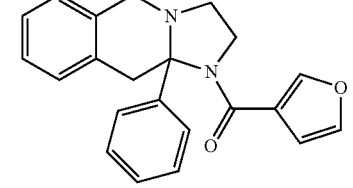

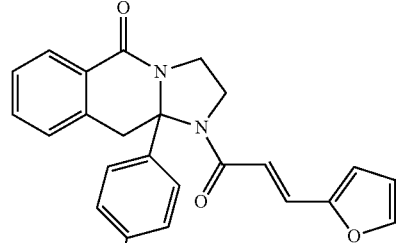

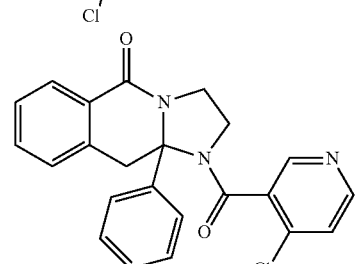

113
-continued
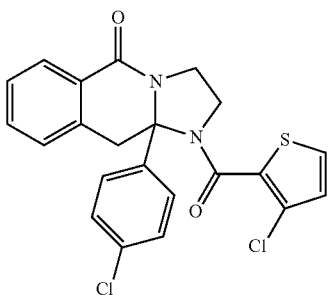
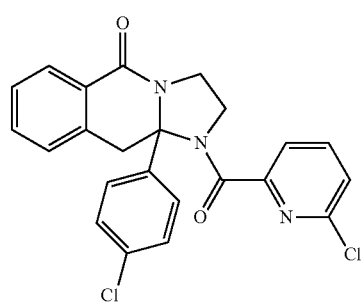
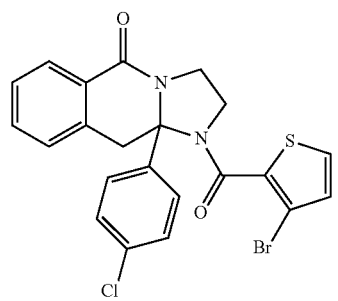
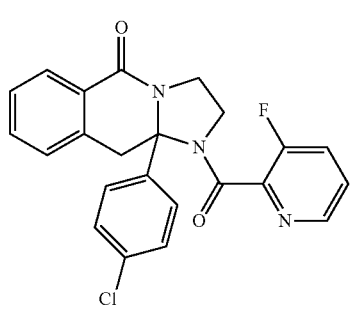
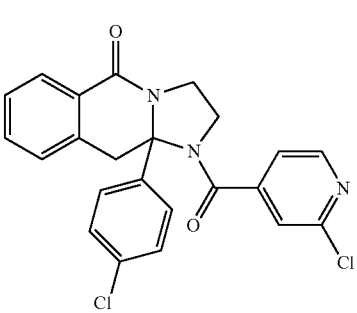
114
-continued
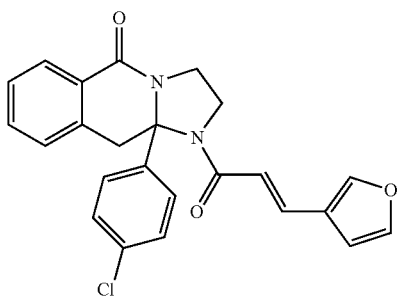
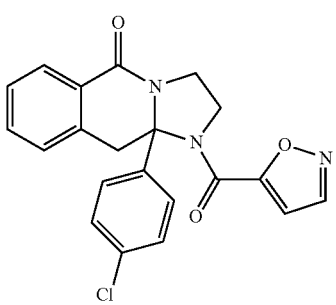
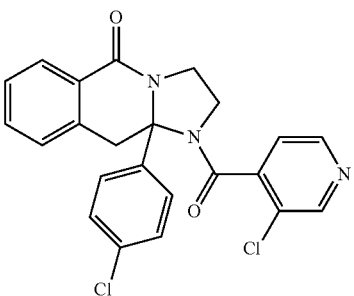
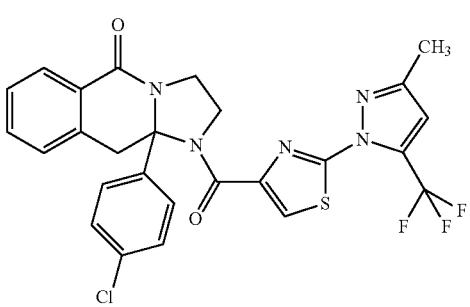
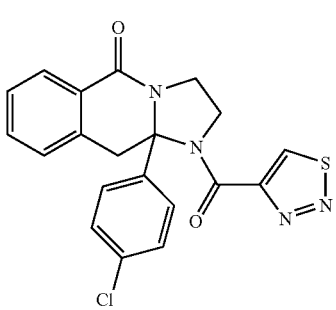

115
-continued
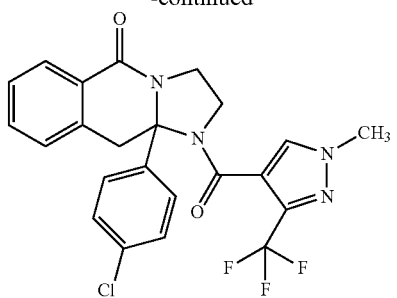
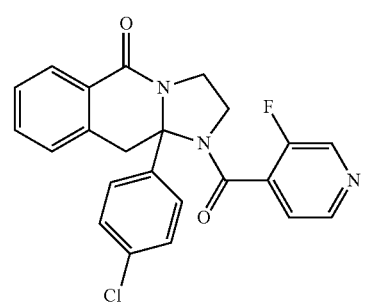
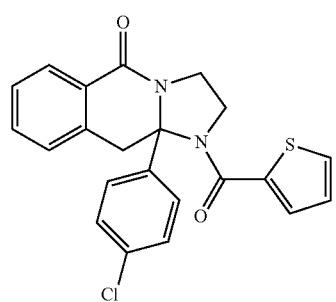
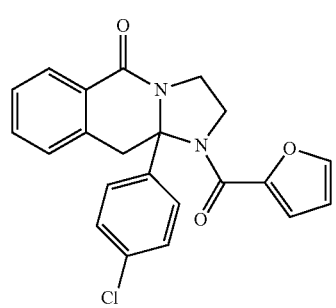
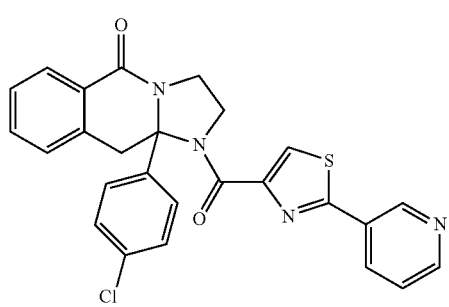
116
-continued
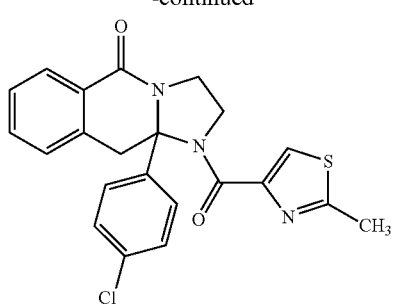
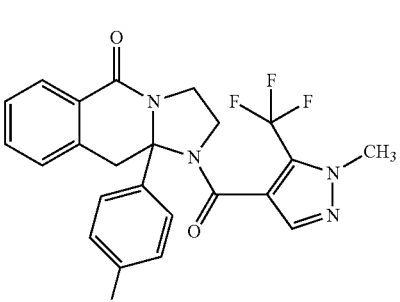
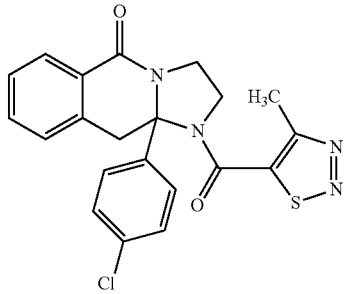
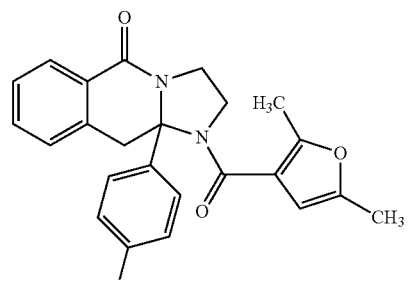
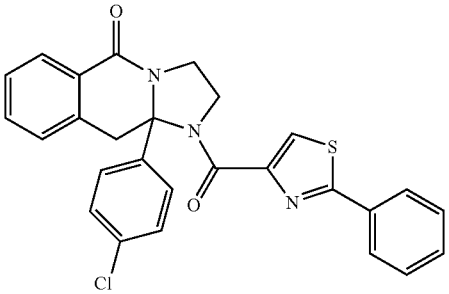

117
-continued
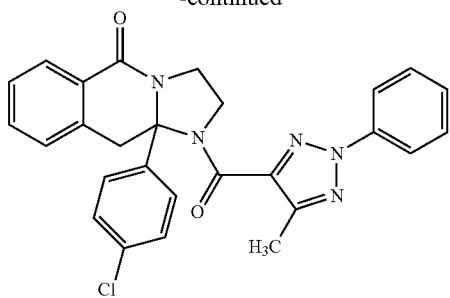
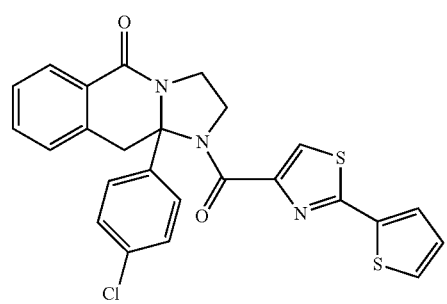
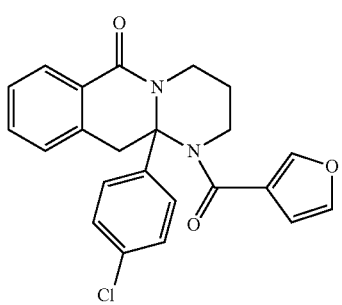
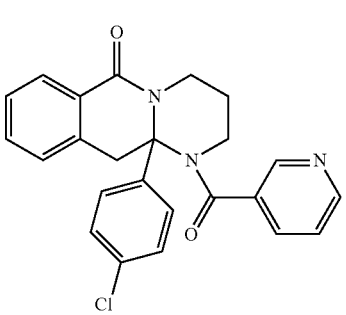
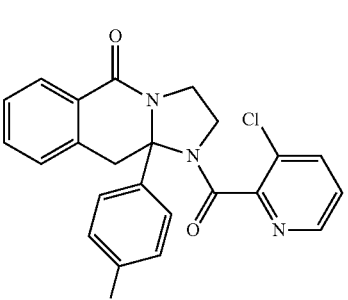
118
-continued
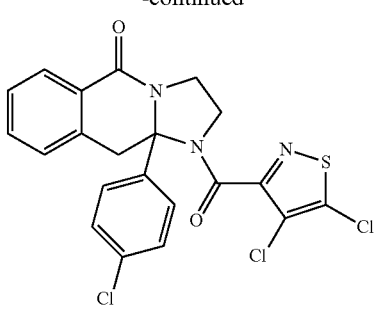
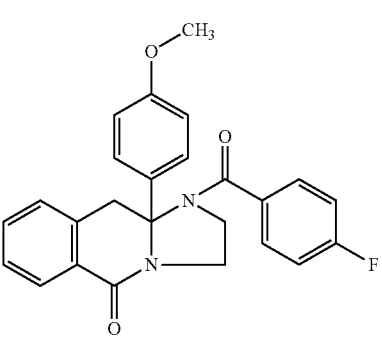
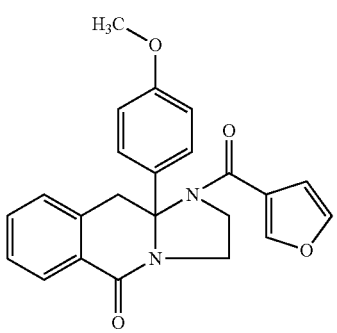
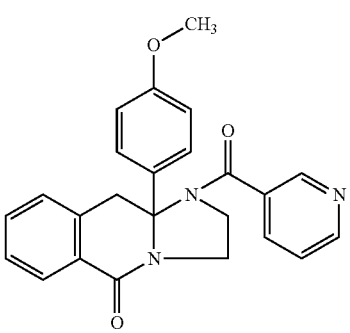
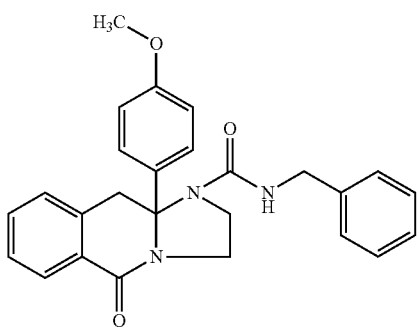

119
-continued
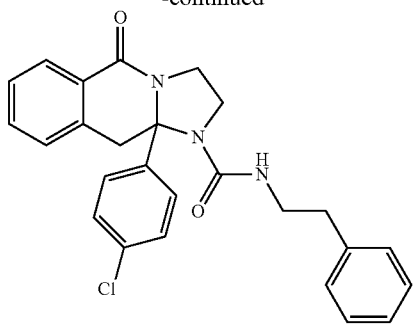
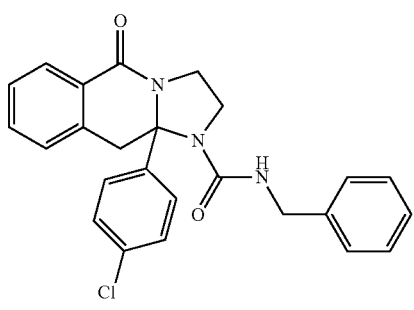 [SMILES: O=C(NCc1ccccc1)N1CCN2C(=O)c3ccccc3CC12c1ccc(Cl)cc1]
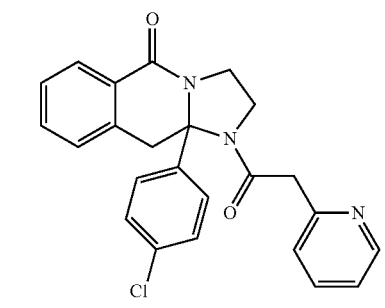 [SMILES: O=C(Cc1ccccn1)N1CCN2C(=O)c3ccccc3CC12c1ccc(Cl)cc1]
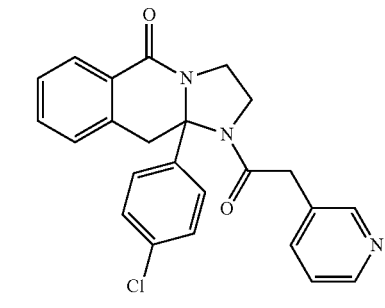
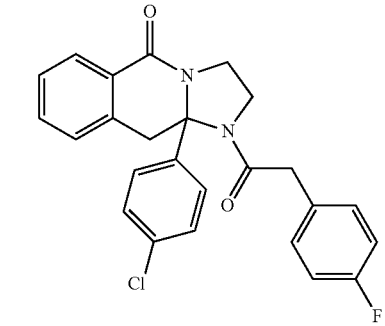
120
-continued
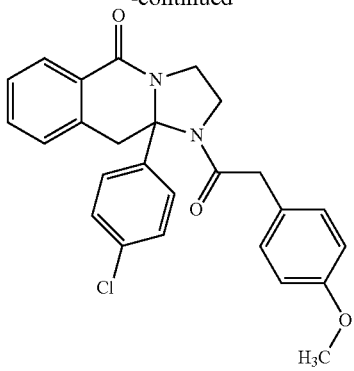
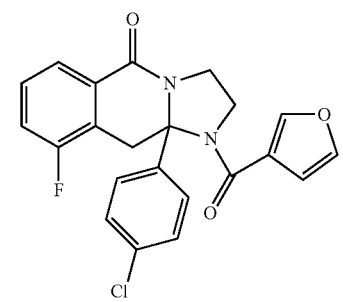
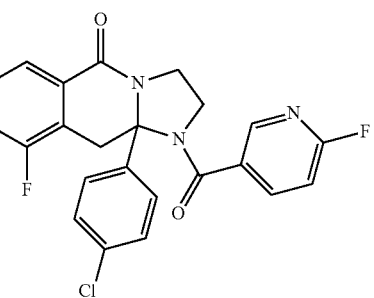
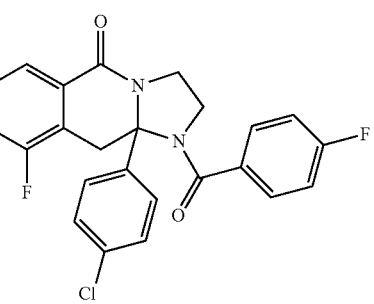
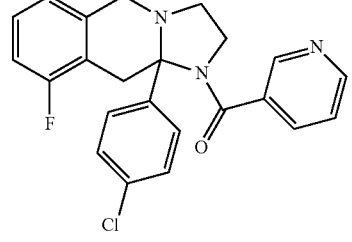

121
-continued
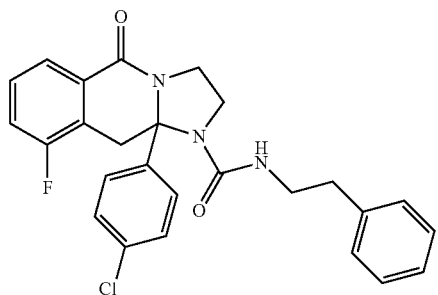
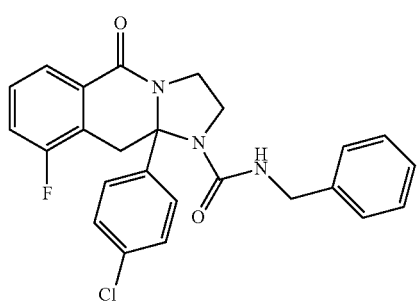
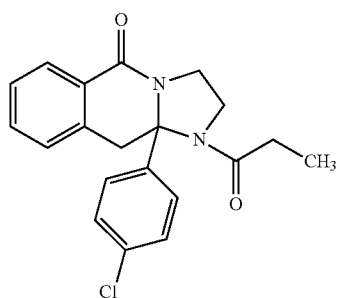
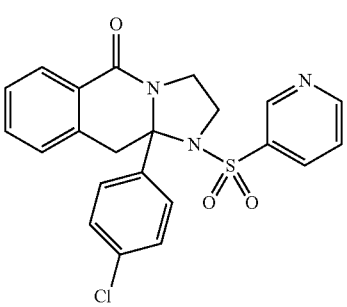
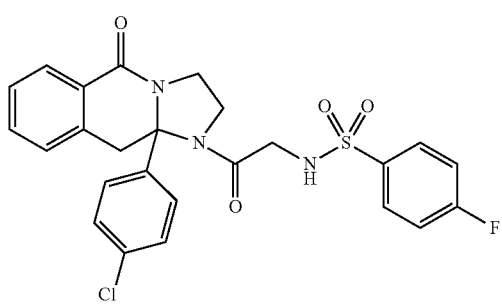
122
-continued
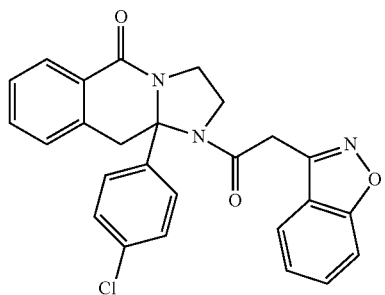
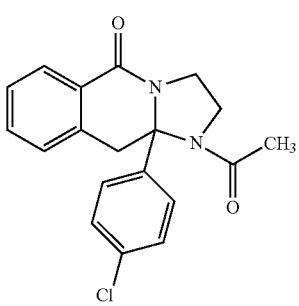
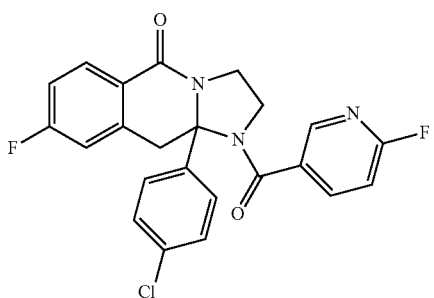
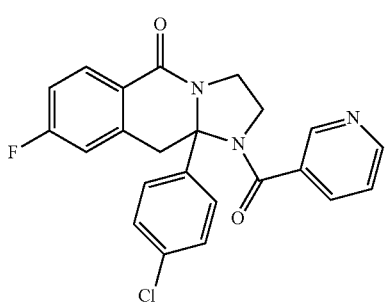
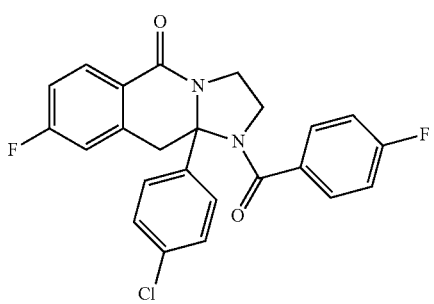

123
-continued
124
-continued
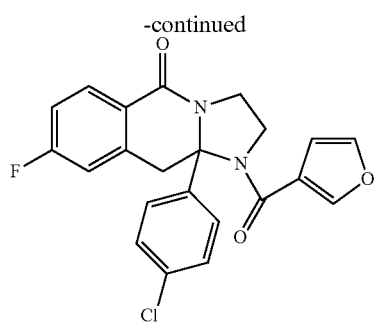
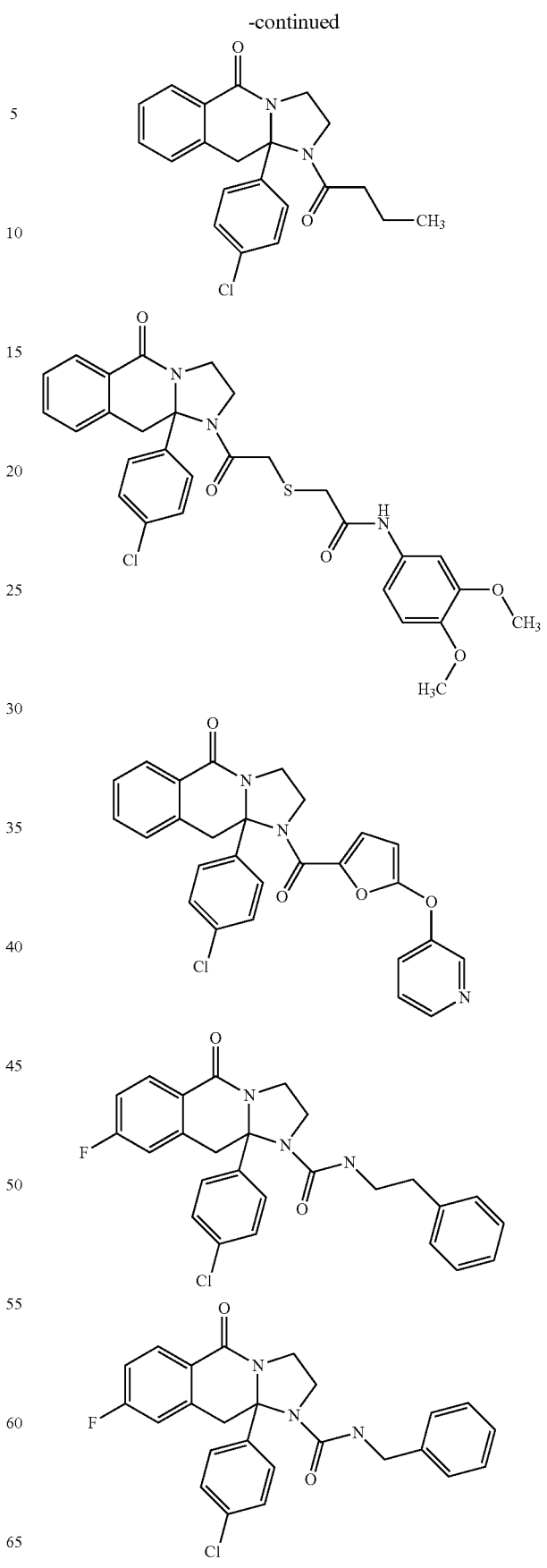

-continued
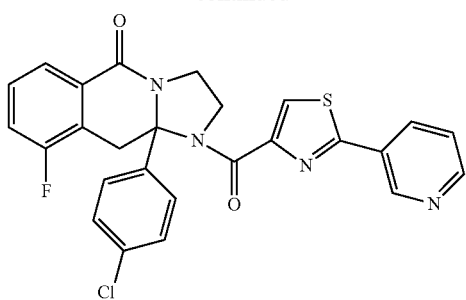
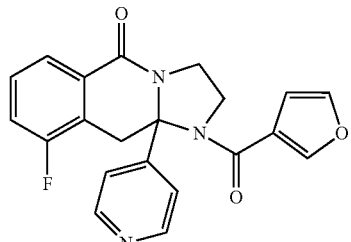
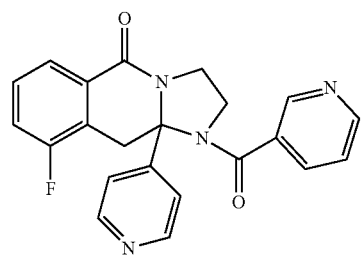
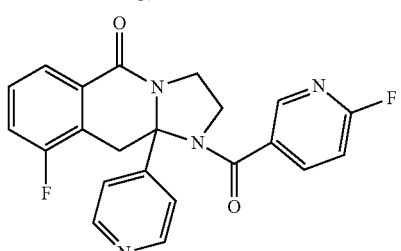
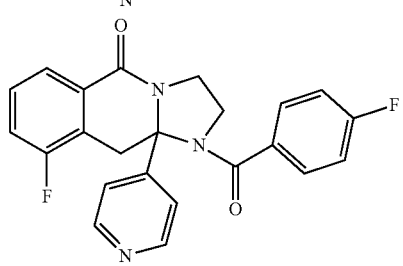
-continued
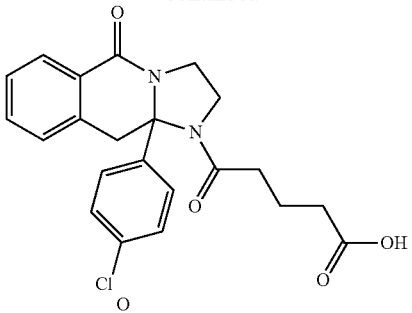
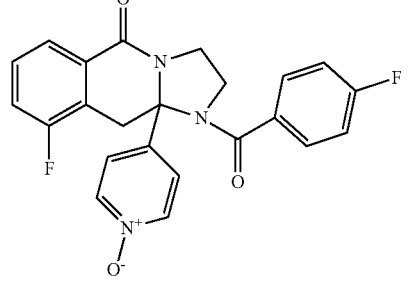
and
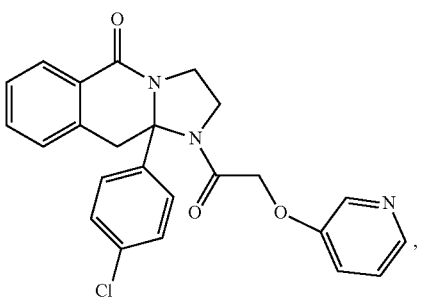
and salts thereof.
23. A compound according to claim 1, which contains a stereogenic center at the point of attachment of $R_1$ according to the following structure:
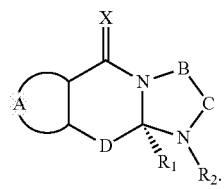
* * * * *

UNITED STATES PATENT AND TRADEMARK OFFICE
CERTIFICATE OF CORRECTION

PATENT NO. : 8,598,194 B2  
APPLICATION NO. : 12/443177  
DATED : December 3, 2013  
INVENTOR(S) : Mitchell et al.

Page 1 of 1

It is certified that error appears in the above-identified patent and that said Letters Patent is hereby corrected as shown below:

In the Claims

At column 110, lines 46-52, please change:

" $R_1$ is selected from H, O, $CH_2R_3$, $C(=Y)R_3$, $-C(=Y)OR_3$, $-C(=Y)N(R_4)R_3$, $-(CH_2)_nC_{4-7}$ cycloalkenyl, $-(CH_2)_n$ aryl, $-(CH_2)_n$ arylC$_{1-12}$ alkyl, $-(CH_2)_n$ arylC$_{2-12}$ alkenyl, $-(CH_2)_n$ arylC$_{2-12}$ alkynyl, and $-(CH_2)_n$ heterocyclyl; n is 0-6; and said alkyl, alkenyl, alkynyl, cycloalkyl, cycloalkenyl, aryl and heterocyclyl groups are optionally substituted; "

to

-- $R_1$ is selected from $C_{1-12}$ alkyl, $C_{2-12}$ alkenyl, $C_{2-12}$ alkynyl, $-(CH_2)_nC_{3-7}$ cycloalkyl, $-(CH_2)_nC_{4-7}$ cycloalkenyl, $-(CH_2)_n$ aryl, $-(CH_2)_n$ arylC$_{1-12}$ alkyl, $-(CH_2)_n$ arylC$_{2-12}$ alkenyl, $-(CH_2)_n$arylC$_{2-12}$ alkynyl, and $-(CH_2)_n$ heterocyclyl; n is 0-6; and said alkyl, alkenyl, alkynyl, cycloalkyl, cycloalkenyl, aryl and heterocyclyl groups are optionally substituted; --

Signed and Sealed this  
Twenty-eighth Day of October, 2014

Michelle K. Lee  
*Deputy Director of the United States Patent and Trademark Office*